US010391171B2

(12) United States Patent
Lai et al.

(10) Patent No.: US 10,391,171 B2
(45) Date of Patent: Aug. 27, 2019

(54) MULTI-SPECIFIC ANTIBODIES FOR CROSS-NEUTRALIZATION OF MULTIPLE FILOVIRUS GLYCOPROTEINS

(71) Applicant: Albert Einstein College of Medicine, Bronx, NY (US)

(72) Inventors: Jonathan R. Lai, Dobbs Ferry, NY (US); Julia Frei, Bronx, NY (US); Elisabeth Nyakatura, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/404,662

(22) Filed: Jan. 12, 2017

(65) Prior Publication Data

US 2017/0182163 A1    Jun. 29, 2017

Related U.S. Application Data

(63) Continuation-in-part of application No. PCT/US2015/057499, filed on Oct. 27, 2015.

(60) Provisional application No. 62/131,472, filed on Mar. 11, 2015, provisional application No. 62/069,516, filed on Oct. 28, 2014.

(51) Int. Cl.
*A61K 39/42* (2006.01)
*C07K 16/10* (2006.01)

(52) U.S. Cl.
CPC .............. *A61K 39/42* (2013.01); *C07K 16/10* (2013.01); *C07K 2317/24* (2013.01); *C07K 2317/31* (2013.01); *C07K 2317/622* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| 2004/0234519 A1 | 11/2004 | Tso et al. |
| 2007/0298042 A1 | 12/2007 | Hart et al. |
| 2012/0164153 A1 | 6/2012 | Dye et al. |
| 2013/0196903 A1 | 8/2013 | Pessi |
| 2014/0356354 A1 | 12/2014 | Lai et al. |

OTHER PUBLICATIONS

Rudikoff et al., PNAS USA, 1982, 79:1979-1983) (Year: 1982).*
MacCallunn et al., J. Mol. Biol., 1996, 262:732-745. (Year: 1996).*
De Pascalis et al., The Journal of Immunology, 2002, 169:3076-3084. (Year: 2002).*
Casset et al., BBRC, 2003, 307:198-205. (Year: 2003).*
Marvin and Zhu, Acta Pharmacologica Sinica, Jun. 2005, 26(6):649-658. (Year: 2005).*
Dong et al., mAbs, May/Jun. 2011, 3(3):273-288. (Year: 2011).*
Dong et al., The Journal of Biological Chemistry, 2011, 286(6):4703-4717. (Year: 2011).*
Lee et al., Nature, Jul. 2008, 454:177-183. (Year: 2008).*
PCT International Search Report and Written Opinion, dated Feb. 4, 2016 in connection with PCT International Application No. PCT/US2015/57499, 10 pages.
PCT International Search Report and Written Opinion, dated Jan. 11, 2016 in connection with PCT International Application No. PCT/US2015/043927, 9 pages.
Chen G et al., entitled "Synthetic Antibodies with a Human Framework That Protect Mice from Lethal Sudan Ebolavirus Challenge," ACS Chemical Biology, Aug. 20, 2014, vol. 9, pp. 2263-2273.
PCT International Preliminary Report on Patentability, dated Jan. 11, 2016 in connection with PCT International Application No. PCT/US2015/043927, 5 pages.

* cited by examiner

*Primary Examiner* — Stacy B Chen
(74) *Attorney, Agent, or Firm* — Foley Hoag LLP

(57) ABSTRACT

Methods for treating and for preventing Filovirus infections are disclosed, as well as compositions therefor.

15 Claims, 10 Drawing Sheets

Specification includes a Sequence Listing.

SEQUENCE LISTING

<160> NUMBER OF SEQ ID NOS: 18

<210> SEQ ID NO 1
<211> LENGTH: 723
<212> TYPE: PRT
<213> ORGANISM: Artificial Sequence
<220> FEATURE:
<223> OTHER INFORMATION: fusion sequence

<400> SEQUENCE: 1

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80
```

```
Leu Gln Met Asn Ser Leu Arg Ala Glu Asp Thr Ala Val Tyr Tyr Cys
                 85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
        130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
        210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Glu Val Gln Leu
            260                 265                 270

Val Glu Ser Gly Gly Gly Leu Val Gln Pro Gly Gly Ser Leu Arg Leu
        275                 280                 285

Ser Cys Ala Ala Ser Gly Phe Ala Phe Asn Tyr Tyr Asp Ile His Trp
        290                 295                 300

Val Arg Gln Ala Pro Gly Lys Gly Leu Glu Trp Val Ala Tyr Ile Asn
305                 310                 315                 320

Pro Gly Gly Gly Asn Thr Tyr Tyr Ala Asp Ser Val Lys Gly Arg Phe
                325                 330                 335

Thr Ile Ser Ala Asp Thr Ser Lys Asn Thr Ala Tyr Leu Gln Met Asn
            340                 345                 350

Ser Leu Arg Ala Glu Asp Thr Ala Val Tyr Tyr Cys Ala Arg Gln Leu
        355                 360                 365

Tyr Gly Asn Ser Phe Met Asp Tyr Trp Gly Gln Gly Thr Leu Val Thr
370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
                405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
        450                 455                 460

Thr Gln Thr Tyr Ile Cys Asn Val Asn His Lys Pro Ser Asn Thr Lys
465                 470                 475                 480

Val Asp Lys Lys Val Glu Pro Lys Ser Cys Asp Lys Thr His Thr Cys
                485                 490                 495
```

Asp Lys Thr His Thr Cys Pro Pro Cys Pro Ala Pro Glu Leu Leu Gly
             500                 505                 510
Arg Pro Ser Val Phe Leu Phe Pro Pro Lys Pro Lys Asp Thr Leu Met
        515                 520                 525
Ile Ser Arg Thr Pro Glu Val Thr Cys Val Val Val Asp Val Ser His
530                 535                 540
Glu Asp Pro Glu Val Lys Phe Asn Trp Tyr Val Asp Gly Val Glu Val
545                 550                 555                 560
His Asn Ala Lys Thr Lys Pro Arg Glu Glu Gln Tyr Asn Ser Thr Tyr
                565                 570                 575
Arg Val Val Ser Val Leu Thr Val Leu His Gln Asp Trp Leu Asn Gly
            580                 585                 590
Lys Glu Tyr Lys Cys Lys Val Ser Asn Lys Ala Leu Pro Ala Pro Ile
        595                 600                 605
Glu Lys Thr Ile Ser Lys Ala Lys Gly Gln Pro Arg Glu Pro Gln Val
    610                 615                 620
Tyr Thr Leu Pro Pro Ser Arg Glu Glu Met Thr Lys Asn Gln Val Ser
625                 630                 635                 640
Leu Thr Cys Leu Val Lys Gly Phe Tyr Pro Ser Asp Ile Ala Val Glu
                645                 650                 655
Trp Glu Ser Asn Gly Gln Pro Glu Asn Asn Tyr Lys Thr Thr Pro Pro
            660                 665                 670
Val Leu Asp Ser Asp Gly Ser Phe Phe Leu Tyr Ser Lys Leu Thr Val
        675                 680                 685
Asp Lys Ser Arg Trp Gln Gln Gly Asn Val Phe Ser Cys Ser Val Met
    690                 695                 700
His Glu Ala Leu His Asn His Tyr Thr Gln Lys Ser Leu Ser Leu Ser
705                 710                 715                 720
Pro Gly Lys

<210> SEQ ID NO 2
<211> LENGTH: 1161
<212> TYPE: DNA
<213> ORGANISM: Artificial Sequence
<220> FEATURE:
<223> OTHER INFORMATION: fusion sequence

<400> SEQUENCE: 2
gaagtgcagt tactggaaag cggcggcggc ctggttaaac tggcggtag tctgcgtctg      60 agttgcgccg ccagcggttt caccctgatc aactaccgca tgaactgggt gcgtcaggca     120
ccgggtaaag gcctggagtg ggtgagcagc attagcagca gcagcta tattcactac       180 gccgacagcg tgaaaggccg ctttaccatc agccgcgaca tgccgagaa cagtctgtat     240 ctgcagatga acagcctaag gcggaagat acagccgtgt actactgtgt gcgcgaaggc     300
cctcgcgcaa ccggctatag catggcagac gtgtttgata tctggggtca gggcaccatg     360
gttacagtta gcagtggtgg tggtggtagt ggtggcggtg tagcggtgg tggtggcagt     420 gaactggtga tgacccagag cccggatagc ttagccgtga gtctgggcga aggggcgacc     480
attaactgca aaagcagcca gagcgtgctg tacagcagca caacaagag ctacctggca     540 tggtatcagc aaaaaccggg tcagcctccg aaactgctga tctattgggc aagcacccgc     600
gaaagtggtg ttccggatcg cttcagcggt agtggcagcg taccgatt cacccctgacc     660 atcagcagtc tgcaggccga ggacgttgca gtgtattact gtcagcagta ctacagcgcc    720
ccgctgacct ttggcggcgg caccaaagtt gaaattaagg gcggcagtgc aggcagcgcc    780

```
ggtagtgccg gtagtggtgg tagcgaagtt cagctggttg aaagtggcgg cggtctggtg    840
cagcctggtg gtagtctgcg tctgagttgt gccgccagcg ctttgccttc aattactat    900 gacattcatt gggttcgcca ggccccgggt aaaggtctgg aatgggttgc atatatcaac    960
ccgggtggcg gtaacaccta ctatgccgac agcgttaagg gtcgcttcac catcagcgca   1020
gataccagca aaacaccgc ctacctgcag atgaatagcc tgcgtgcaga agataccgcc   1080
gtttactact gtgcccgcca gctgtacggc aatagcttca tggactattg gggccagggc   1140
accttagtta ccgtgagcag c                                            1161
```

<210> SEQ ID NO 3
<211> LENGTH: 493
<212> TYPE: PRT
<213> ORGANISM: Artificial Sequence
<220> FEATURE:
<223> OTHER INFORMATION: fusion sequence

<400> SEQUENCE: 3

```
Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Leu Ile Asn Tyr
             20                  25                  30

Arg Met Asn Trp Val Arg Gln Ala Pro Gly Lys Gly Leu Glu Trp Val
         35                  40                  45

Ser Ser Ile Ser Ser Ser Ser Tyr Ile His Tyr Ala Asp Ser Val
     50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                 85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Asp Ile Gln Met
            260                 265                 270

Thr Gln Ser Pro Ser Ser Leu Ser Ala Ser Val Gly Asp Arg Val Thr
        275                 280                 285
```

```
Ile Thr Cys Arg Ala Ser Gln Asp Val Thr Thr Ala Val Ala Trp Tyr
    290                 295                 300
Gln Gln Lys Pro Gly Lys Ala Pro Lys Leu Leu Ile Tyr Trp Ala Ser
305                 310                 315                 320
Arg Leu His Asn Gly Val Pro Ser Arg Phe Ser Gly Ser Gly Ser Gly
                325                 330                 335
Thr Asp Phe Thr Leu Thr Ile Ser Ser Leu Gln Pro Glu Asp Phe Ala
            340                 345                 350
Thr Tyr Tyr Cys Gln Gln His Tyr Ser Thr Pro Leu Thr Phe Gly Gln
            355                 360                 365
Gly Thr Lys Val Glu Ile Lys Arg Thr Val Ala Ala Pro Ser Val Phe
370                 375                 380
Ile Phe Pro Pro Ser Asp Glu Gln Leu Lys Ser Gly Thr Ala Ser Val
385                 390                 395                 400
Val Cys Leu Leu Asn Asn Phe Tyr Pro Arg Glu Ala Lys Val Gln Trp
                405                 410                 415
Lys Val Asp Asn Ala Leu Gln Ser Gly Asn Ser Gln Glu Ser Val Thr
                420                 425                 430
Glu Gln Asp Ser Lys Asp Ser Thr Tyr Ser Leu Ser Ser Thr Leu Thr
            435                 440                 445
Leu Ser Lys Ala Asp Tyr Glu Lys His Lys Val Tyr Ala Cys Glu Val
450                 455                 460
Thr His Gln Gly Leu Ser Ser Pro Val Thr Lys Ser Phe Asn Arg Gly
465                 470                 475                 480
Glu Cys Gly Gly Ser Asp Tyr Lys Asp Asp Asp Lys
                485                 490
```

<210> SEQ ID NO 4
<211> LENGTH: 1125
<212> TYPE: DNA
<213> ORGANISM: Artificial Sequence
<220> FEATURE:
<223> OTHER INFORMATION: fusion sequence

<400> SEQUENCE: 4

| | | | | | |
|---|---|---|---|---|---|
| gaagtgcagc | tgctggaaag | cggtggcggt | ctggttaaac | tggcggtag | tctgcgcctg | 60 |
| agttgcgccg | ccagcggttt | tacactgatc | aactatcgca | tgaactgggt | gcgtcaggca | 120 |
| ccgggtaagg | gtctggagtg | ggttagcagc | attagtagca | gcagcagtta | cattcactac | 180 |
| gccgatagcg | tgaaaggccg | cttcacaatt | agccgcgata | acgccgagaa | cagcctgtat | 240 |
| ctgcagatga | acagtttacg | cgccgaagat | accgccgtgt | attattgcgt | tcgcgaaggt | 300 |
| ccgcgtgcaa | ccggctacag | catggccgac | gttttcgata | tttggggtca | gggcaccatg | 360 |
| gtgacagtta | gtagcggtgg | tggtggtagt | ggtggtggcg | gcagcggtgg | tggtggtagt | 420 |
| gaactggtga | tgacccagag | cccggatagc | ctggcagtga | gcctgggtga | gcgtgccacc | 480 |
| atcaattgca | aaagcagcca | gagcgtgctg | tacagcagca | acaacaagag | ttacctggcc | 540 |
| tggtaccaac | agaaaccggg | ccagccgccg | aaactgctga | tttattgggc | cagtacccgc | 600 |
| gaaagcggcg | tgcctgatcg | ttttagtggc | agcggtagcg | gcaccgactt | taccctgacc | 660 |
| attagcagcc | tgcaggccga | ggatgtggca | gtgtattact | gccagcagta | ttacagcgcc | 720 |
| ccgttaacct | ttggcggcgg | taccaaagtg | gagatcaaag | tggcagtgc | aggcagcgcc | 780 |
| ggtagtgcag | gtagtggtgg | tagcgacatc | cagatgacac | agagtccgag | cagcctgagt | 840 |
| gccagcgttg | gtgaccgtgt | gaccattacc | tgccgtgcca | gccaggatgt | taccacagcc | 900 |

-continued

```
gttgcatggt atcagcagaa gccgggtaag gcccctaagt tactgatcta ctgggcaagc    960
cgcctgcata acgtgtgcc gagccgcttt agcggcagtg gtagcggtac cgatttcacc    1020
ctgaccatca gcagtctgca gccggaagat ttcgcaacct actactgtca gcagcattac    1080
agcaccccgc tgacctttgg ccagggcacc aaagtggaaa ttaaa                    1125
```

<210> SEQ ID NO 5
<211> LENGTH: 723
<212> TYPE: PRT
<213> ORGANISM: Artificial Sequence
<220> FEATURE:
<223> OTHER INFORMATION: fusion sequence

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Ile His Trp Val Arg Gln Ala Pro Gly Lys Gly Leu Glu Trp Val
        35                  40                  45

Ala Tyr Ile Asn Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Asn Ser Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
            325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys Gly Gly Ser Ala Gly Ser Ala Gly Ser
                450                 455                 460
Ala Gly Ser Gly Gly Ser Glu Val Gln Leu Leu Glu Ser Gly Gly Gly
465                 470                 475                 480
Leu Val Lys Pro Gly Gly Ser Leu Arg Leu Ser Cys Ala Ala Ser Gly
                485                 490                 495
Phe Thr Leu Ile Asn Tyr Arg Met Asn Trp Val Arg Gln Ala Pro Gly
                500                 505                 510
Lys Gly Leu Glu Trp Val Ser Ser Ile Ser Ser Ser Ser Ser Tyr Ile
                515                 520                 525
His Tyr Ala Asp Ser Val Lys Gly Arg Phe Thr Ile Ser Arg Asp Asn
                530                 535                 540
Ala Glu Asn Ser Leu Tyr Leu Gln Met Asn Ser Leu Arg Ala Glu Asp
545                 550                 555                 560
Thr Ala Val Tyr Tyr Cys Val Arg Glu Gly Pro Arg Ala Thr Gly Tyr
                565                 570                 575
Ser Met Ala Asp Val Phe Asp Ile Trp Gly Gln Gly Thr Met Val Thr
                580                 585                 590
Val Ser Ser Gly Gly Gly Gly Ser Gly Gly Gly Gly Ser Gly Gly Gly
                595                 600                 605
Gly Ser Glu Leu Val Met Thr Gln Ser Pro Asp Ser Leu Ala Val Ser
                610                 615                 620
Leu Gly Glu Arg Ala Thr Ile Asn Cys Lys Ser Ser Gln Ser Val Leu
625                 630                 635                 640
Tyr Ser Ser Asn Asn Lys Ser Tyr Leu Ala Trp Tyr Gln Gln Lys Pro
                645                 650                 655
Gly Gln Pro Pro Lys Leu Leu Ile Tyr Trp Ala Ser Thr Arg Glu Ser
                660                 665                 670
Gly Val Pro Asp Arg Phe Ser Gly Ser Gly Ser Gly Thr Asp Phe Thr
                675                 680                 685
Leu Thr Ile Ser Ser Leu Gln Ala Glu Asp Val Ala Val Tyr Tyr Cys
                690                 695                 700
Gln Gln Tyr Tyr Ser Ala Pro Leu Thr Phe Gly Gly Gly Thr Lys Val
705                 710                 715                 720
Glu Ile Lys

<210> SEQ ID NO 6
<211> LENGTH: 1614
```

```
<212> TYPE: DNA
<213> ORGANISM: Artificial Sequence
<220> FEATURE:
<223> OTHER INFORMATION: fusion sequence

<400> SEQUENCE: 6
gaggttcagc tggtggagtc tggcggtggc ctggtgcagc cagggggctc actccgtttg      60
tcctgtgcag cttctggctt cgcgtttaac tattatgata ttcattgggt gcgtcaggcc     120
ccgggtaagg gcctggaatg ggttgcatat attaacccgg cggtggcaa cacctattat     180
gctgatagcg tcaagggccg tttcactata agcgcagaca catccaaaaa cacagcctac     240
ctacaaatga acagcttaag agctgaggac actgccgtct attattgtgc tcgccagctg     300
tatggcaaca gctttatgga ctactggggt caaggaaccc tggtcaccgt ctcctcggct     360
agcaccaagg gtccgagcgt gtttcctctg caccagca gtaaaagcac cagtggtggt     420
acagcagccc tgggttgcct ggtgaaggat tactttccgg agccggtgac cgttagttgg     480
aatagcggcg ccctgaccag tggcgttcat acatttccgg ccgtgctgca gagtagtggc     540
ctgtacagcc tgagtagcgt tgttaccgtt ccgagcagca gcctgggcac ccagacctat     600
atttgcaatg ttaaccataa accgagcaac acaaaagttg ataaaaaagt tgaaccgaag     660
agctgtgaca aacccatac atgtgacaaa acacacacct gcccgccttg tccggcacct     720
gagctgctgg gtcgcccgag cgttttctg tttcctccga aaccgaaaga caccacccag     780
aagagtctga gcctgagtcc tggcaaaggt ggatccgccg gtagcgcagg tagtgcaggt     840
agtggcggca gcgaagttca gctgttagaa agtggcggtg gtctggttaa gccgggcggt     900
agtctgcgcc tgagctgtgc agcaagtggt ttcacccctga tcaattatcg tatgaactgg     960
gtgcgccaag ccccgggtaa aggtctggag tgggttagta gtatcagcag cagcagcagt    1020
tacatccact atgccgatag cgttaagggc cgctttacaa tcagccgcga taatgccgag    1080
aatagcttat acctgcaaat gaacagtcta agggcggaag ataccgccgt ttactactgc    1140
gttcgtgaag cccctcgcgc aacaggctat agcatggcag acgtgttcga catttggggt    1200
cagggcacca tggtgaccgt tagtagcggc ggtggtggta gtggtggtgg cggtagtggt    1260
ggcggtggca gcgaactggt gatgacccag agtccggata gcctggccgt gagcttaggc    1320
gagcgtgcaa ccattaattg taaaagcagt cagagtgttc tgtatagtag caataacaag    1380
agctatctgg cctggtatca gcagaagccg ggccagccgc cgaaactgct gatttactgg    1440
gcaagcaccc gcgaaagtgg cgtgcctgat cgctttagtg gtagcggcag cggcaccgat    1500
tttaccctga ccattagcag tctgcaggcc gaggacgttg ccgtttatta ctgccagcag    1560
tactatagcg caccgctgac atttggcggt ggcaccaagg tggaaattaa ataa           1614

<210> SEQ ID NO 7
<211> LENGTH: 485
<212> TYPE: PRT
<213> ORGANISM: Artificial Sequence
<220> FEATURE:
<223> OTHER INFORMATION: fusion sequence

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Thr Thr Ala
                20                  25                  30

Val Ala Trp Tyr Gln Gln Lys Pro Gly Lys Ala Pro Lys Leu Leu Ile
         35                  40                  45
```

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln His Tyr Ser Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Ser Gly Gly Ser Ala Gly Ser Ala
    210                 215                 220

Gly Ser Ala Gly Ser Gly Gly Ser Glu Val Gln Leu Leu Glu Ser Gly
225                 230                 235                 240

Gly Gly Leu Val Lys Pro Gly Gly Ser Leu Arg Leu Ser Cys Ala Ala
            245                 250                 255

Ser Gly Phe Thr Leu Ile Asn Tyr Arg Met Asn Trp Val Arg Gln Ala
            260                 265                 270

Pro Gly Lys Gly Leu Glu Trp Val Ser Ser Ile Ser Ser Ser Ser Ser
        275                 280                 285

Tyr Ile His Tyr Ala Asp Ser Val Lys Gly Arg Phe Thr Ile Ser Arg
    290                 295                 300

Asp Asn Ala Glu Asn Ser Leu Tyr Leu Gln Met Asn Ser Leu Arg Ala
305                 310                 315                 320

Glu Asp Thr Ala Val Tyr Tyr Cys Val Arg Glu Gly Pro Arg Ala Thr
            325                 330                 335

Gly Tyr Ser Met Ala Asp Val Phe Asp Ile Trp Gly Gln Gly Thr Met
            340                 345                 350

Val Thr Val Ser Ser Gly Gly Gly Gly Ser Gly Gly Gly Gly Ser Gly
            355                 360                 365

Gly Gly Gly Ser Glu Leu Val Met Thr Gln Ser Pro Asp Ser Leu Ala
370                 375                 380

Val Ser Leu Gly Glu Arg Ala Thr Ile Asn Cys Lys Ser Ser Gln Ser
385                 390                 395                 400

Val Leu Tyr Ser Ser Asn Asn Lys Ser Tyr Leu Ala Trp Tyr Gln Gln
                405                 410                 415

Lys Pro Gly Gln Pro Lys Leu Leu Ile Tyr Trp Ala Ser Thr Arg
            420                 425                 430

Glu Ser Gly Val Pro Asp Arg Phe Ser Gly Ser Gly Ser Gly Thr Asp
            435                 440                 445

Phe Thr Leu Thr Ile Ser Ser Leu Gln Ala Glu Asp Val Ala Val Tyr
    450                 455                 460

Tyr Cys Gln Gln Tyr Tyr Ser Ala Pro Leu Thr Phe Gly Gly Gly Thr
465                 470                 475                 480

Lys Val Glu Ile Lys
            485

<210> SEQ ID NO 8
<211> LENGTH: 1455
<212> TYPE: DNA
<213> ORGANISM: Artificial Sequence
<220> FEATURE:
<223> OTHER INFORMATION: fusion sequence
<220> FEATURE:
<221> NAME/KEY: misc_feature
<222> LOCATION: (1443)..(1443)
<223> OTHER INFORMATION: n is a, c, g, or t

<400> SEQUENCE: 8

| | | | | | |
|---|---|---|---|---|---|
| gatatccaga | tgacccagtc | cccgagctcc | ctgtccgcct | ctgtgggcga | tagggtcacc | 60 |
| atcacctgcc | gggcgagcca | ggatgtgacc | accgctgtag | cctggtatca | acagaaacca | 120 |
| ggaaaagctc | cgaagcttct | gatttactgg | gcgagccgtc | ttcataatgg | cgtgccgagc | 180 |
| cgctttagcg | gcagcggctc | cgggacggat | ttcactctga | ccatcagcag | tctgcagccg | 240 |
| gaagacttcg | caacttatta | ctgtcagcaa | cattatagca | ccccgctgac | gttcggacag | 300 |
| ggtaccaagg | tggagatcaa | acgtacggtg | gcagcaccga | gcgtgtttat | ctttccgccg | 360 |
| agcgacgaac | aactgaaaag | tggcacagcc | agcgtggtgt | gtttactgaa | caacttctat | 420 |
| cctcgcgagg | ccaaggtgca | gtggaaagtg | gacaatgcac | tgcagagtgg | caatagccag | 480 |
| gagagcgtga | ccgaacagga | tagcaaagat | agcacctata | gcctgagtag | caccctgacc | 540 |
| ctgagcaagg | ccgattatga | gaagcacaag | gtgtatgcat | gcgaggttac | ccatcagggc | 600 |
| ctgagcagcc | cggtgaccaa | aagctttaac | cgtggcgaat | gcgtggtag | tggtggatcc | 660 |
| gccggtagcg | caggtagtgc | aggtagtggc | ggcagcgaag | ttcagctgtt | agaaagtggc | 720 |
| ggtggtctgg | ttaagccggg | cggtagtctg | cgcctgagct | gtgcagcaag | tggtttcacc | 780 |
| ctgatcaatt | atcgtatgaa | ctgggtgcgc | caagcccggg | taaaggtct | ggagtgggtt | 840 |
| agtagtatca | gcagcagcag | cagttacatc | cactatgccg | atagcgttaa | gggccgcttt | 900 |
| acaatcagcc | gcgataatgc | cgagaatagc | ttatacctgc | aaatgaacag | tctaagggcg | 960 |
| gaagataccg | ccgtttacta | ctgcgttcgt | gaaggccctc | gcgcaacagg | ctatagcatg | 1020 |
| gcagacgtgt | tcgacatttg | gggtcagggc | accatggtga | ccgttagtag | cggcggtggt | 1080 |
| ggtagtggtg | gtggcggtag | tggtggcggt | ggcagcgaac | tggtgatgac | ccagagtccg | 1140 |
| gatagcctgg | ccgtgagctt | aggcgagcgt | gcaaccatta | attgtaaaag | cagtcagagt | 1200 |
| gttctgtata | gtagcaataa | caagagctat | ctggcctggt | atcagcagaa | gccgggccag | 1260 |
| ccgccgaaac | tgctgattta | ctgggcaagc | acccgcgaaa | gtggcgtgcc | tgatcgcttt | 1320 |
| agtggtagcg | gcagcggcac | cgatttacc | ctgaccatta | gcagtctgca | ggccgaggac | 1380 |
| gttgccgttt | attactgcca | gcagtactat | agcgcaccgc | tgacatttgg | cggtggcacc | 1440 |
| aangtggaaa | ttaaa | | | | | 1455 |

<210> SEQ ID NO 9
<211> LENGTH: 723
<212> TYPE: PRT
<213> ORGANISM: Artificial Sequence
<220> FEATURE:
<223> OTHER INFORMATION: fusion sequence

<400> SEQUENCE: 9

-continued

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Ser Glu Val Gln Leu
            260                 265                 270

Val Glu Ser Gly Gly Gly Leu Val Gln Pro Gly Gly Ser Leu Arg Leu
        275                 280                 285

Ser Cys Ala Ala Ser Gly Phe Ala Phe Asn Tyr Tyr Asp Met Phe Trp
    290                 295                 300

Val Arg Gln Ala Pro Gly Lys Gly Leu Glu Trp Val Ala Tyr Ile Lys
305                 310                 315                 320

Pro Gly Gly Gly Asn Thr Tyr Tyr Ala Asp Ser Val Lys Gly Arg Phe
                325                 330                 335

Thr Ile Ser Ala Asp Thr Ser Lys Asn Thr Ala Tyr Leu Gln Met Asn
            340                 345                 350

Ser Leu Arg Ala Glu Asp Thr Ala Val Tyr Tyr Cys Ala Arg Gln Leu
        355                 360                 365

Tyr Gly Asn Ser Phe Phe Asp Tyr Trp Gly Gln Gly Thr Leu Val Thr
    370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
                405                 410                 415
```

```
Lys Asp Tyr Phe Pro Glu Pro Val Thr Val Ser Trp Asn Ser Gly Ala
                420                 425                 430

Leu Thr Ser Gly Val His Thr Phe Pro Ala Val Leu Gln Ser Ser Gly
            435                 440                 445

Leu Tyr Ser Leu Ser Ser Val Val Thr Val Pro Ser Ser Ser Leu Gly
450                 455                 460

Thr Gln Thr Tyr Ile Cys Asn Val Asn His Lys Pro Ser Asn Thr Lys
465                 470                 475                 480

Val Asp Lys Lys Val Glu Pro Lys Ser Cys Asp Lys Thr His Thr Cys
                485                 490                 495

Asp Lys Thr His Thr Cys Pro Pro Cys Pro Ala Pro Glu Leu Leu Gly
            500                 505                 510

Arg Pro Ser Val Phe Leu Phe Pro Pro Lys Pro Lys Asp Thr Leu Met
            515                 520                 525

Ile Ser Arg Thr Pro Glu Val Thr Cys Val Val Val Asp Val Ser His
            530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
            595                 600                 605

Glu Lys Thr Ile Ser Lys Ala Lys Gly Gln Pro Arg Glu Pro Gln Val
            610                 615                 620

Tyr Thr Leu Pro Pro Ser Arg Glu Glu Met Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
            675                 680                 685

Asp Lys Ser Arg Trp Gln Gln Gly Asn Val Phe Ser Cys Ser Val Met
            690                 695                 700

His Glu Ala Leu His Asn His Tyr Thr Gln Lys Ser Leu Ser Leu Ser
705                 710                 715                 720

Pro Gly Lys

<210> SEQ ID NO 10
<211> LENGTH: 1161
<212> TYPE: DNA
<213> ORGANISM: Artificial Sequence
<220> FEATURE:
<223> OTHER INFORMATION: fusion sequence

<400> SEQUENCE: 10
gaagttcagt tactggaaag tggcggcggc ctggttaaac cgggtggtag cctgcgtctg      60
agttgcgcag caagcggctt caccctgatc aactatcgca tgaactgggt gcgccaagca     120
ccgggtaagg gtctggagtg ggtgagcagc atcagcagca gcagcagcta catccactac     180
gcagacagcg ttaaaggccg cttcaccatt agccgcgata cgccgaaaaa cagcctgtac     240
ctgcagatga acagtctaag ggcggaggat accgcagtgt actactgcgt tcgtgaaggc     300
```

```
ccgcgtgcaa ccggctatag catggccgac gttttttgata tttggggcca gggcaccatg    360
gtgaccgtga gtagtggtgg tggtggcagc ggtggtggcg gtagtggtgg tggtggcagt    420
gaactggtta tgacccagag tccggacagt ctggcagtga gcctgggcga gcgtgcaacc    480
atcaactgta agagcagtca gagcgtgctg tatagtagca acaataaaag ctatctggcc    540
tggtatcagc agaagccggg tcagccgcct aagctgctga tttattgggc cagcacccgc    600
gaaagcggtg ttccggatcg ctttagcggt agcggcagcg gtaccgattt cacccctgacc    660
atcagcagcc tgcaggccga agatgtggcc gtgtattatt gccagcagta ctacagcgcc    720
ccgctgacct ttggtggcgg taccaaggtg gaaattaaag gcggcagtgc cggtagtgcc    780
ggtagtgcag gtagcggcgg tagcgaggtt cagctggtgg aaagcggcgg tggtctggtt    840
cagcctggtg gtagcctgcg cctgagctgt gccgcaagcg gtttcgcatt taactactat    900
gacatgttct gggttcgcca ggcaccgggc aaaggtctgg aatgggtggc ctatatcaaa    960
ccgggcggcg gcaacaccta ctacgccgat agcgttaagg gtcgtttcac catcagcgcc    1020
gataccagca aaaacaccgc ctatctgcag atgaatagcc taaggcgga agacaccgca    1080
gtgtattact gcgcacgcca gctgtacggc aacagctttt tcgattactg gggccagggt    1140
accctggtta ccgtgagcag c                                             1161
```

<210> SEQ ID NO 11
<211> LENGTH: 493
<212> TYPE: PRT
<213> ORGANISM: Artificial Sequence
<220> FEATURE:
<223> OTHER INFORMATION: fusion sequence

<400> SEQUENCE: 11

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205
```

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Asp Ile Gln Met
                260                 265                 270

Thr Gln Ser Pro Ser Ser Leu Ser Ala Ser Val Gly Asp Arg Val Thr
            275                 280                 285

Ile Thr Cys Lys Ala Ser Gln Asp Val Thr Thr Ala Val Ala Trp Tyr
        290                 295                 300

Gln Gln Lys Pro Gly Lys Ala Pro Lys Leu Leu Ile Tyr Trp Ala Ser
305                 310                 315                 320

Thr Arg His Thr Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
                340                 345                 350

Thr Tyr Tyr Cys Gln Gln His Tyr Ser Thr Pro Leu Thr Phe Gly Gln
            355                 360                 365

Gly Thr Lys Val Glu Ile Lys Arg Thr Val Ala Ala Pro Ser Val Phe
    370                 375                 380

Ile Phe Pro Pro Ser Asp Glu Gln Leu Lys Ser Gly Thr Ala Ser Val
385                 390                 395                 400

Val Cys Leu Leu Asn Asn Phe Tyr Pro Arg Glu Ala Lys Val Gln Trp
                405                 410                 415

Lys Val Asp Asn Ala Leu Gln Ser Gly Asn Ser Gln Glu Ser Val Thr
                420                 425                 430

Glu Gln Asp Ser Lys Asp Ser Thr Tyr Ser Leu Ser Ser Thr Leu Thr
            435                 440                 445

Leu Ser Lys Ala Asp Tyr Glu Lys His Lys Val Tyr Ala Cys Glu Val
        450                 455                 460

Thr His Gln Gly Leu Ser Ser Pro Val Thr Lys Ser Phe Asn Arg Gly
465                 470                 475                 480

Glu Cys Gly Gly Ser Asp Tyr Lys Asp Asp Asp Lys
                485                 490

<210> SEQ ID NO 12
<211> LENGTH: 1125
<212> TYPE: DNA
<213> ORGANISM: Artificial Sequence
<220> FEATURE:
<223> OTHER INFORMATION: fusion sequence

<400> SEQUENCE: 12
gaagttcagt tactggaaag tggcggcggc ctggttaaac cgggtggtag cctgcgtctg      60
agttgcgcag caagcggctt caccctgatc aactatcgca tgaactgggt gcgccaagca     120
ccgggtaagg gtctggagtg ggtgagcagc atcagcagca gcagcagcta catccactac     180
gcagacagcg ttaaaggccg cttcaccatt agccgcgata cgccgaaaaa cagcctgtac     240
ctgcagatga acagtctaag gcggaggat accgcagtgt actactgcgt tcgtgaaggc     300
ccgcgtgcaa ccggctatag catggccgac gttttttgata tttggggcca gggcaccatg     360
gtgaccgtga gtagtggtgg tggtggcagc ggtggtggcg gtagtggtgg tggtggcagt     420
gaactggtta tgacccagag tccggacagt ctggcagtga gcctgggcga gcgtgcaacc     480

```
atcaactgta agagcagtca gagcgtgctg tatagtagca acaataaaag ctatctggcc    540
tggtatcagc agaagccggg tcagccgcct aagctgctga tttattgggc agcacccgc    600 gaaagcggtg ttccggatcg ctttagcggt agcggcagcg gtaccgattt caccctgacc    660
atcagcagcc tgcaggccga agatgtggcc gtgtattatt gccagcagta ctacagcgcc    720
ccgctgacct ttggtggcgg taccaaggtg gaaattaaag cggcagtgc cggtagtgcc    780 ggtagtgcag gtagcggcgg tagcgatatc cagatgaccc agagtccgag tagtctgagc    840
gccagcgttg gtgaccgcgt taccatcacc tgcaaggcca gcaggatgt taccaccgcc    900 gtggcctggt atcaacagaa accgggcaag gccccgaagc tgctgattta tgggccagt    960 acacgccata caggcgtgcc gagccgtttt agtggcagcg gtagcggtac cgacttcacc   1020
ctgaccatca gtagcctgca accggaggat ttcgccacct actactgcca gcagcactac   1080 agcacccgc tgacctttgg ccaaggtacc aaggtggaga ttaag                  1125
```

<210> SEQ ID NO 13
<211> LENGTH: 723
<212> TYPE: PRT
<213> ORGANISM: Artificial Sequence
<220> FEATURE:
<223> OTHER INFORMATION: fusion sequence

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Met Phe Trp Val Arg Gln Ala Pro Gly Lys Gly Leu Glu Trp Val
        35                  40                  45

Ala Tyr Ile Lys Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Asn Ser Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
```

```
                    245                 250                 255
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys Gly Gly Ser Ala Gly Ser Ala Gly Ser
                450                 455                 460

Ala Gly Ser Gly Gly Ser Glu Val Gln Leu Leu Glu Ser Gly Gly Gly
465                 470                 475                 480

Leu Val Lys Pro Gly Gly Ser Leu Arg Leu Ser Cys Ala Ala Ser Gly
                485                 490                 495

Phe Thr Leu Ile Asn Tyr Arg Met Asn Trp Val Arg Gln Ala Pro Gly
                500                 505                 510

Lys Gly Leu Glu Trp Val Ser Ser Ile Ser Ser Ser Ser Ser Tyr Ile
                515                 520                 525

His Tyr Ala Asp Ser Val Lys Gly Arg Phe Thr Ile Ser Arg Asp Asn
                530                 535                 540

Ala Glu Asn Ser Leu Tyr Leu Gln Met Asn Ser Leu Arg Ala Glu Asp
545                 550                 555                 560

Thr Ala Val Tyr Tyr Cys Val Arg Glu Gly Pro Arg Ala Thr Gly Tyr
                565                 570                 575

Ser Met Ala Asp Val Phe Asp Ile Trp Gly Gln Gly Thr Met Val Thr
                580                 585                 590

Val Ser Ser Gly Gly Gly Gly Ser Gly Gly Gly Ser Gly Gly Gly Gly
                595                 600                 605

Gly Ser Glu Leu Val Met Thr Gln Ser Pro Asp Ser Leu Ala Val Ser
                610                 615                 620

Leu Gly Glu Arg Ala Thr Ile Asn Cys Lys Ser Ser Gln Ser Val Leu
625                 630                 635                 640

Tyr Ser Ser Asn Asn Lys Ser Tyr Leu Ala Trp Tyr Gln Gln Lys Pro
                645                 650                 655

Gly Gln Pro Pro Lys Leu Leu Ile Tyr Trp Ala Ser Thr Arg Glu Ser
                660                 665                 670
```

Gly Val Pro Asp Arg Phe Ser Gly Ser Gly Ser Gly Thr Asp Phe Thr
            675                 680                 685

Leu Thr Ile Ser Ser Leu Gln Ala Glu Asp Val Ala Val Tyr Tyr Cys
        690                 695                 700

Gln Gln Tyr Tyr Ser Ala Pro Leu Thr Phe Gly Gly Gly Thr Lys Val
705                 710                 715                 720

Glu Ile Lys

<210> SEQ ID NO 14
<211> LENGTH: 2172
<212> TYPE: DNA
<213> ORGANISM: Artificial Sequence
<220> FEATURE:
<223> OTHER INFORMATION: fusion sequence

<400> SEQUENCE: 14

| | | | | | |
|---|---|---|---|---|---|
| gaagttcaac | tggttgagag | tggcggtggc | ttagttcaac | cgggcggtag | tttacgcctg | 60 |
| agttgtgcag | ccagcggttt | cgccttcaac | tattatgaca | tgttttgggt | gcgccaggca | 120 |
| ccgggtaaag | gcctggagtg | ggtggcctat | atcaaaccgg | gcggtggcaa | cacctattac | 180 |
| gccgatagcg | tgaaaggtcg | ctttaccatc | agcgcagata | ccagcaagaa | taccgcctac | 240 |
| ctgcagatga | atagcctgcg | tgccgaagac | accgccgttt | attattgcgc | cgccagctg | 300 |
| tacggcaata | gcttttttcga | ttactggggc | cagggcaccc | tggttaccgt | tagcagcgct | 360 |
| agcaccaagg | gtccgagcgt | gtttcctctg | gcacctagca | gtaaaagcac | cagtggtggt | 420 |
| acagcagccc | tgggttgcct | ggtgaaggat | tactttccgg | agccggtgac | cgttagttgg | 480 |
| aatagcggcg | ccctgaccag | tggcgttcat | acatttccgg | ccgtgctgca | gagtagtggc | 540 |
| ctgtacagcc | tgagtagcgt | tgttaccgtt | ccgagcagca | gcctgggcac | ccagacctat | 600 |
| atttgcaatg | ttaaccataa | accgagcaac | acaaaagttg | ataaaaaagt | tgaaccgaag | 660 |
| agctgtgaca | aaacccatac | atgtgacaaa | acacacacct | gcccgccttg | tccggcacct | 720 |
| gagctgctgg | gtcgcccgag | cgttttttctg | tttcctccga | aaccgaaaga | caccctgatg | 780 |
| atcagccgca | cacctgaggt | gacctgtgtt | gtggtggatg | tgagccacga | agatcctgaa | 840 |
| gttaagttta | actggtatgt | ggatggcgtg | gaggtgcata | atgccaagac | aaagccgcgt | 900 |
| gaagagcagt | acaacagcac | ctatcgtgtt | gttagtgtgc | tgaccgttct | gcaccaagat | 960 |
| tggctgaacg | gcaaggagta | taatgcaag | gttagcaata | aagccctgcc | ggccccgatc | 1020 |
| gagaagacca | tcagcaaagc | caaagtcag | ccgcgtgagc | ctcaggtgta | tacactgccg | 1080 |
| cctagccgtg | aggagatgac | caagaatcag | gttagcctga | cctgtctggt | gaaaggcttt | 1140 |
| tacccgagcg | atatcgccgt | tgagtgggaa | agcaatggtc | agcctgagaa | caactacaag | 1200 |
| accacccccgc | ctgtttttaga | cagtgatggt | agcttttttct | tatacagcaa | actgaccgtt | 1260 |
| gataagagcc | gctggcagca | gggcaatgtg | tttagctgca | gtgttatgca | tgaggccctg | 1320 |
| cataaccact | atacccagaa | gagtctgagc | ctgagtcctg | gcaaaggtgg | atccgccggt | 1380 |
| agcgcaggta | gtgcaggtag | tggcggcagc | gaagttcagc | tgttagaaag | tggcggtggt | 1440 |
| ctggttaagc | cgggcggtag | tctgcgcctg | agctgtgcag | caagtggttt | caccctgatc | 1500 |
| aattatcgta | tgaactgggt | gcgccaagcc | ccgggtaaag | gtctggagtg | ggttagtagt | 1560 |
| atcagcagca | gcagcagtta | catccactat | gccgatagcg | ttaagggccg | ctttacaatc | 1620 |
| agccgcgata | atgccgagaa | tagccttatac | ctgcaaatga | acagtctaag | ggcggaagat | 1680 |
| accgccgttt | actactgcgt | tcgtgaaggc | cctcgcgcaa | caggctatag | catggcagac | 1740 |

-continued

```
gtgttcgaca tttggggtca gggcaccatg gtgaccgtta gtagcggcgg tggtggtagt    1800
ggtggtggcg gtagtggtgg cggtggcagc gaactggtga tgacccagag tccggatagc    1860
ctggccgtga gcttaggcga gcgtgcaacc attaattgta aaagcagtca gagtgttctg    1920
tatagtagca ataacaagag ctatctggcc tggtatcagc agaagccggg ccagccgccg    1980
aaactgctga tttactgggc aagcacccgc gaaagtggcg tgcctgatcg ctttagtggt    2040
agcggcagcg gcaccgattt taccctgacc attagcagtc tgcaggccga ggacgttgcc    2100
gtttattact gccagcagta ctatagcgca ccgctgacat ttggcggtgg caccaaggtg    2160
gaaattaaat aa                                                        2172
```

<210> SEQ ID NO 15
<211> LENGTH: 485
<212> TYPE: PRT
<213> ORGANISM: Artificial Sequence
<220> FEATURE:
<223> OTHER INFORMATION: fusion sequence

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Gly Ser Ala Gly Ser Ala
    210                 215                 220

Gly Ser Ala Gly Ser Gly Gly Ser Glu Val Gln Leu Leu Glu Ser Gly
225                 230                 235                 240

Gly Gly Leu Val Lys Pro Gly Gly Ser Leu Arg Leu Ser Cys Ala Ala
                245                 250                 255

Ser Gly Phe Thr Leu Ile Asn Tyr Arg Met Asn Trp Val Arg Gln Ala
            260                 265                 270

Pro Gly Lys Gly Leu Glu Trp Val Ser Ser Ile Ser Ser Ser Ser Ser
```

```
                275                 280                 285
Tyr Ile His Tyr Ala Asp Ser Val Lys Gly Arg Phe Thr Ile Ser Arg
        290                 295                 300

Asp Asn Ala Glu Asn Ser Leu Tyr Leu Gln Met Asn Ser Leu Arg Ala
305                 310                 315                 320

Glu Asp Thr Ala Val Tyr Tyr Cys Val Arg Glu Gly Pro Arg Ala Thr
                325                 330                 335

Gly Tyr Ser Met Ala Asp Val Phe Asp Ile Trp Gly Gln Gly Thr Met
            340                 345                 350

Val Thr Val Ser Ser Gly Gly Gly Gly Ser Gly Gly Gly Gly Ser Gly
        355                 360                 365

Gly Gly Gly Ser Glu Leu Val Met Thr Gln Ser Pro Asp Ser Leu Ala
    370                 375                 380

Val Ser Leu Gly Glu Arg Ala Thr Ile Asn Cys Lys Ser Ser Gln Ser
385                 390                 395                 400

Val Leu Tyr Ser Ser Asn Asn Lys Ser Tyr Leu Ala Trp Tyr Gln Gln
                405                 410                 415

Lys Pro Gly Gln Pro Pro Lys Leu Leu Ile Tyr Trp Ala Ser Thr Arg
            420                 425                 430

Glu Ser Gly Val Pro Asp Arg Phe Ser Gly Ser Gly Ser Gly Thr Asp
        435                 440                 445

Phe Thr Leu Thr Ile Ser Ser Leu Gln Ala Glu Asp Val Ala Val Tyr
    450                 455                 460

Tyr Cys Gln Gln Tyr Tyr Ser Ala Pro Leu Thr Phe Gly Gly Gly Thr
465                 470                 475                 480

Lys Val Glu Ile Lys
                485

<210> SEQ ID NO 16
<211> LENGTH: 1458
<212> TYPE: DNA
<213> ORGANISM: Artificial Sequence
<220> FEATURE:
<223> OTHER INFORMATION: fusion sequence

<400> SEQUENCE: 16
gacattcaga tgacccaaag tccgagcagc ctgagtgcca gtgttggtga tcgcgtgaca      60
atcacatgca aggccagtca ggacgtgacc accgcagtgg cctggtatca gcagaaaccg     120
ggtaaggccc cgaagctgct gatctattgg gccagtaccc gccacaccgg tgttcctagt     180
cgcttcagtg gcagtggcag cggcacagat ttcaccctga ccatcagcag cctgcaaccg     240
gaagattttg ccacctacta ctgccagcag cactatagca cccgctgacc ctttggccag     300
ggcaccaagg ttgagattaa cgtacggtg gcagcaccga gcgtgtttat ctttccgccg     360
agcgacgaac aactgaaaag tggcacagcc agcgtggtgt gtttactgaa caacttctat     420
cctcgcgagg ccaaggtgca gtggaaagtg gacaatgcac tgcagagtgg caatagccag     480
gagagcgtga ccgaacagga tagcaaagat agcacctata gcctgagtag caccctgacc     540
ctgagcaagg ccgattatga gaagcacaag gtgtatgcat gcgaggttac ccatcagggc     600
ctgagcagcc cggtgaccaa agctttaac cgtggcgaat cgtggtag tgtggatcc     660 gccggtagcg caggtagtgc aggtagtggc ggcagcgaag ttcagctgtt agaaagtggc     720
ggtggtctgg ttaagccggg cggtagtctg cgcctgagct gtgcagcaag tggtttcacc     780
ctgatcaatt atcgtatgaa ctgggtgcgc caagccccgg gtaaaggtct ggagtgggtt     840
```

```
agtagtatca gcagcagcag cagttacatc cactatgccg atagcgttaa gggccgcttt    900
acaatcagcc gcgataatgc cgagaatagc ttatacctgc aaatgaacag tctaagggcg    960
gaagataccg ccgtttacta ctgcgttcgt gaaggccctc gcgcaacagg ctatagcatg   1020
gcagacgtgt tcgacatttg gggtcagggc accatggtga ccgttagtag cggcggtggt   1080
ggtagtggtg gtggcggtag tggtggcggt ggcagcgaac tggtgatgac ccagagtccg   1140
gatagcctgg ccgtgagctt aggcgagcgt gcaaccatta attgtaaaag cagtcagagt   1200
gttctgtata gtagcaataa caagagctat ctggcctggt atcagcagaa gccgggccag   1260
ccgccgaaac tgctgattta ctgggcaagc acccgcgaaa gtggcgtgcc tgatcgcttt   1320
agtggtagcg gcagcggcac cgattttacc ctgaccatta gcagtctgca ggccgaggac   1380
gttgccgttt attactgcca gcagtactat agcgcaccgc tgacatttgg cggtggcacc   1440
aaggtggaaa ttaaataa                                                 1458
```

<210> SEQ ID NO 17
<211> LENGTH: 15
<212> TYPE: PRT
<213> ORGANISM: Artificial Sequence
<220> FEATURE:
<223> OTHER INFORMATION: linker sequence

<400> SEQUENCE: 17

Gly Gly Ser Ala Gly Ser Ala Gly Ser Ala Gly Ser Gly Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: linker sequence

<400> SEQUENCE: 18

Gly Gly Gly Gly Ser Gly Gly Gly Gly Ser Gly Gly Gly Gly Ser
1               5                   10                  15

MULTI-SPECIFIC ANTIBODIES FOR CROSS-NEUTRALIZATION OF MULTIPLE FILOVIRUS GLYCOPROTEINS

CROSS-REFERENCE TO RELATED APPLICATIONS

This application is a continuation-in-part of PCT International Application No. PCT/US2015/57499, filed Oct. 27, 2015, which claims benefit of U.S. Provisional Application Nos. 62/131,472, filed Mar. 11, 2015 and 62/069,516, filed Oct. 28, 2014, the contents of each of which are hereby incorporated by reference.

STATEMENT OF GOVERNMENT SUPPORT

This invention was made with government support under grant numbers AI009762 and AI090249 and GM007482 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Ebola virus is an NIAID Category A biodefense pathogen that causes severe and rapidly progressing hemorrhagic fever with human case fatalities of 50-90%. There are currently no FDA-approved vaccines or therapies for Ebola virus infection. Among the five species of Ebola virus, the Zaire and Sudan variants (EBOV and SUDV, respectively) are the most pathogenic and both have resulted in recurring outbreaks. Together, EBOV and SUDV account for over 95% of EBOV-related deaths reported to date.

Herein are disclosed multi-specific antibodies for cross-neutralization of multiple Filovirus glycoproteins.

SUMMARY OF THE INVENTION

This invention provides a composition comprising (1) a first single chain variable fragment (scFv) comprising at least one CDR directed to a membrane glycoprotein pre-fusion core of a first species of filovirus, which first scFv is covalently joined to (2) a first polypeptide of an immunoglobulin G (IgG) comprising at least one CDR directed to a membrane glycoprotein pre-fusion core of a second species of filovirus, wherein the first species of filovirus and second species of filovirus are different species.

A composition is also provided comprising (i) a first single chain variable fragment (scFv) comprising at least one CDR directed to a membrane glycoprotein pre-fusion core of a first species of filovirus, which first scFv is covalently joined to (ii) a first polypeptide of an immunoglobulin G (IgG) comprising at least one CDR directed to a membrane glycoprotein pre-fusion core of a second species of filovirus, the IgG having covalently joined thereto, at a different location from the attachment of (i) thereto, (iii) a second single chain variable fragment (scFv) comprising at least one CDR directed to a membrane glycoprotein pre-fusion core of a third species of filovirus, wherein the first species of filovirus and second species of filovirus and third species of filovirus are all different species. In an embodiment, one species-specific scFv is fused to the light chain of an IgG, and different species-specific scFv is fused to the heavy chain of the IgG.

Also provided is an isolated nucleic acid encoding any of the compositions described herein.

Also provided is a method of treating a filovirus infection in a subject comprising administering an amount of a bispecific composition described herein to the subject effective to treat a filovirus infection in a subject.

Also provided is a method of preventing a filovirus infection in a subject comprising administering an amount of a bispecific composition described herein to the subject effective to inhibit a filovirus infection in a subject.

Also provided is a method of preventing a filovirus infection of a mammalian cell comprising contacting the filovirus with an amount of a bispecific composition described herein effective to inhibit a filovirus infection of a mammalian cell.

Also provided is a method of treating a filovirus infection in a subject comprising administering an amount of a trispecific composition described herein to the subject effective to treat a filovirus infection in a subject.

Also provided is a method of preventing a filovirus infection in a subject comprising administering an amount of a trispecific composition described herein to the subject effective to inhibit a filovirus infection in a subject.

Also provided is a method of preventing a filovirus infection of a mammalian cell comprising contacting the filovirus with an amount of a trispecific composition described herein effective to inhibit a filovirus infection of a mammalian cell.

Herein are disclosed cross-neutralizing, bispecific monoclonal antibody constructs against Ebola variants such as EBOV and SUDV. Recent structural studies indicate that the base of the envelope glycoprotein (GP) is susceptible to neutralization by antibodies in these two species. However, current EBOV and SUDV antibodies targeting this region are narrowly strain specific and therefore have limited therapeutic utility. Herein a fusion approach is disclosed whereby, for example, the IgG of one species-specific antibody (e.g., SUDV) is genetically fused to the scFv of another species-specific antibody (e.g., EBOV) to create a cross-species neutralizing antibody (or vice versa). This strategy can also be extended to generate trispecific antibody constructs. Antibody therapies against Ebolaviruses and other filoviruses have demonstrated post-exposure efficacy in nonhuman primates, but no cross-neutralizing antibodies exist. Therefore, the cross-neutralizing, bispecific antibodies disclosed herein fill a much needed gap in Ebola therapeutics.

BRIEF DESCRIPTION OF THE DRAWINGS

FIG. 1A-1B: Structure of the prefusion GP1-GP2 spike and GP conformational changes that lead to viral membrane fusion. (A) Structure of the GP1-GP2 spike ectodomain (PDB ID: 3CSY, (13)). The GP1 subunits are shown in surface-shaded view and GP2 as rods and loops. One GP1 subunit is colored to show the subdomains: b, base; h, head; gc, glycan cap. fp, fusion peptide; TM, transmembrane domain. C, GP C-terminus. (B) Membrane fusion-associated conformational rearrangements in GP2 inferred from its pre-fusion and putative post-fusion structures (PDB ID: 1EBO, ref 17)

FIG. 2. Survival of NHPs administered EBOV-specific serum IgGs upon viral challenge. Animals 7, 8, and 9 survived but the control animal (5) died 8-days post-exposure. (These data are from ref 21, Dye et al.).

Figure 3:
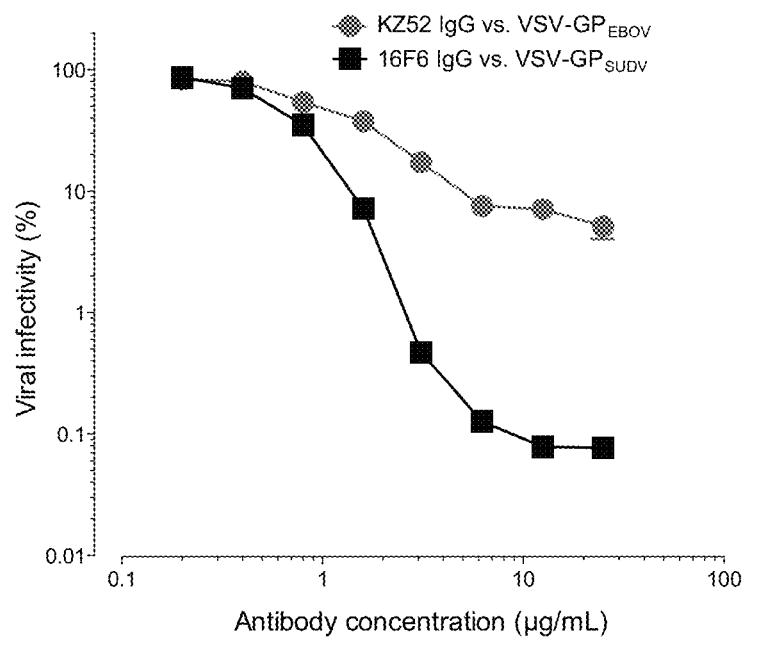

FIG. 3. Head-to-head comparison of KZ52 IgG vs. VSV-GP$_{EBOV}$ and 16F6 IgG vs. VSV-GP$_{SUDV}$.

Figure 4:
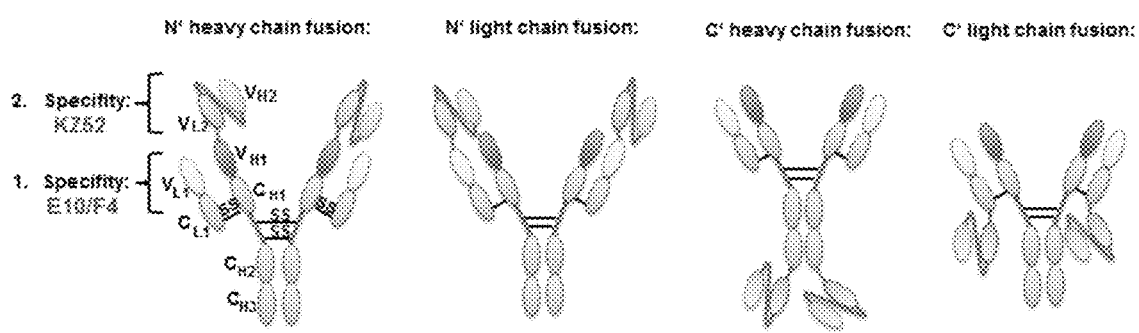

FIG. 4. Exemplary Bispecific (E10 & F4 IgG+KZ52 scFv) designs.

Figure 5:
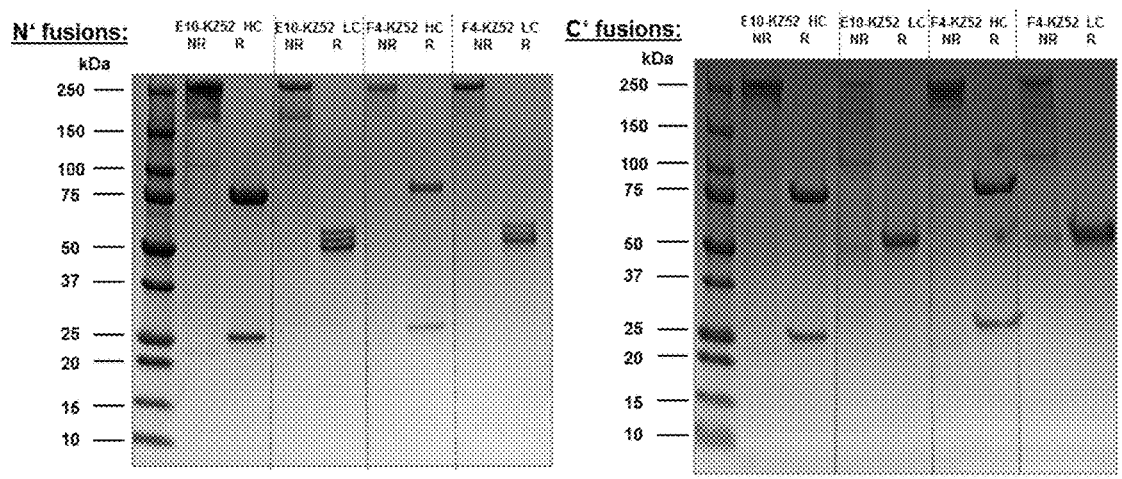

FIG. 5. Bispecifics (E10 & F4 IgG+KZ52 scFv) SDS PAGE.

Figure 6:
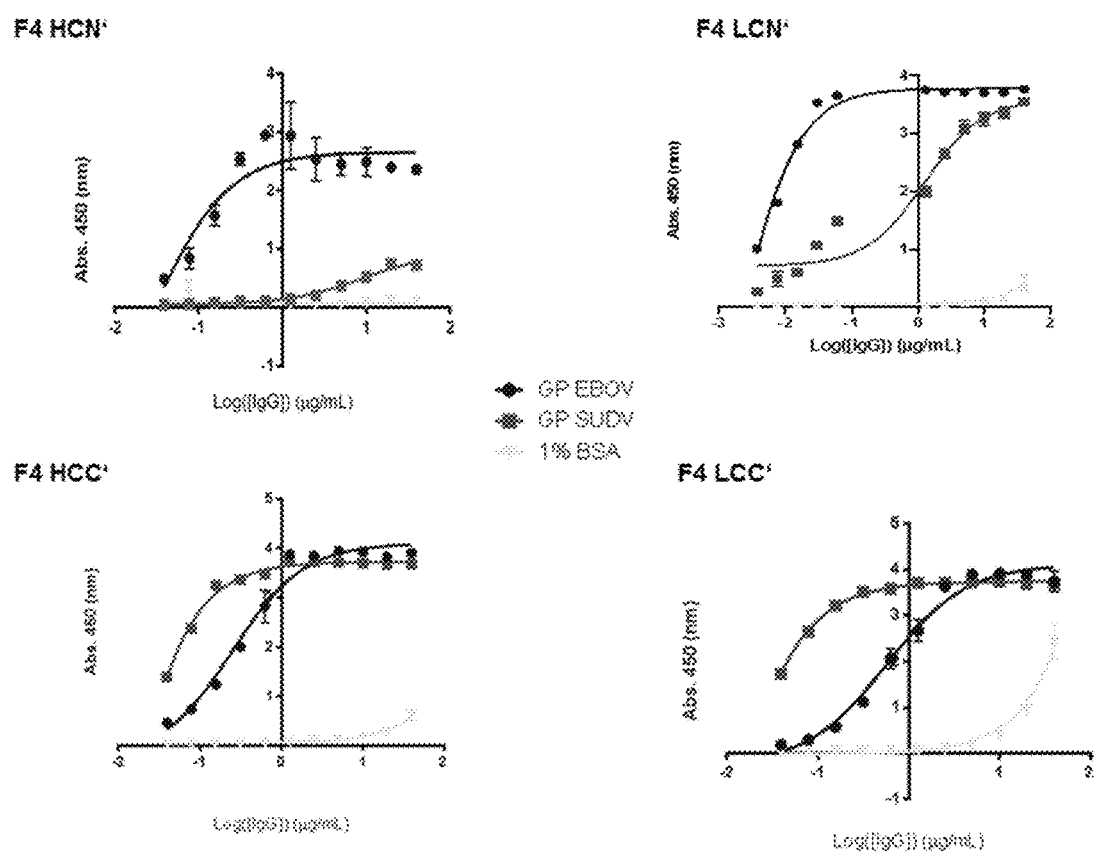

FIG. 6. Bispecifics (F4 IgG+KZ52 scFv) binding data.

Figure 7:
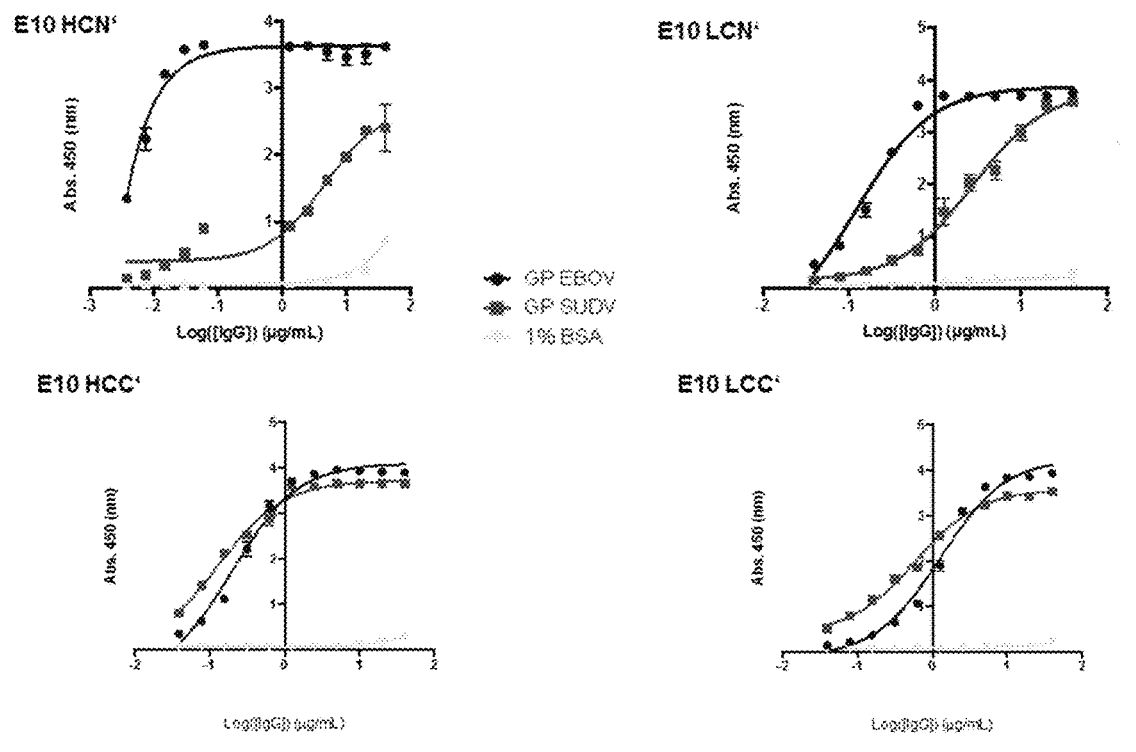

FIG. 7. Bispecifics (E10 IgG+KZ52 scFv) binding data.

Figure 8:
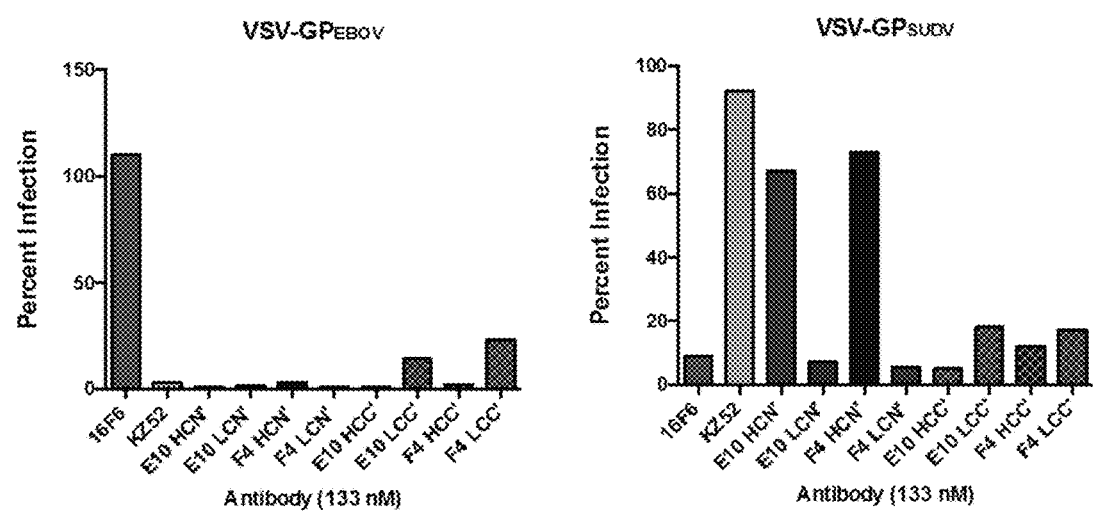

FIG. 8. Bispecific antibodies neutralization assay results.

Figures 9A, 9B:
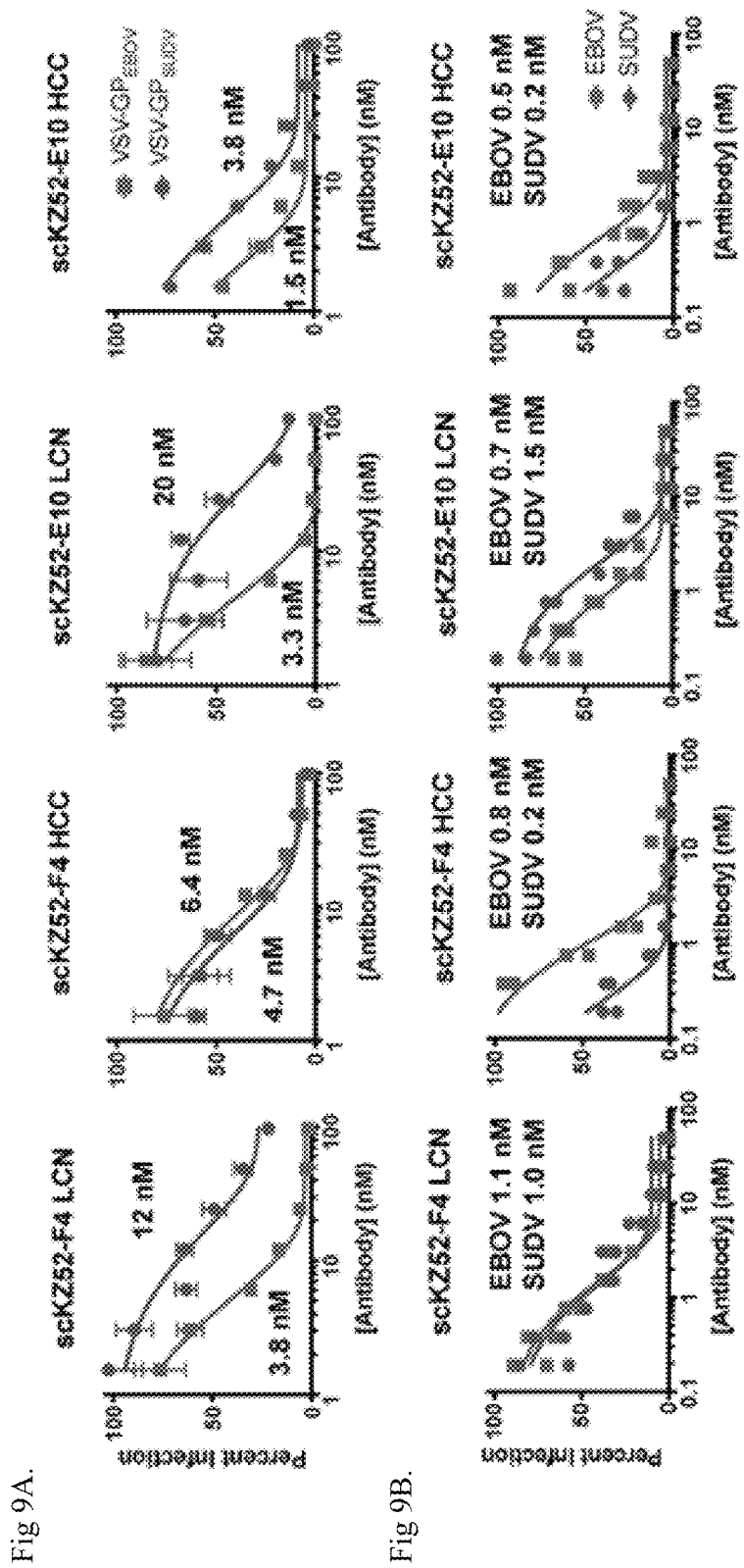

FIG. 9A-9B. Virus neutralization. (A) Dose-dependent neutralization of VSV-GPEBOV and VSV-GPSUDV by scKZ52-F4 LCN, scKZ52-F4 HCC, scKZ52-E10 LCN, and scKZ52-E10 HCC. Calculated IC50 values are listed next to each curve. (B) Neutralization of authentic viruses by PRNT assay, with IC50 values listed.

FIG. 10A-10D. Animal challenge experiments. Percent survival and median percent weight change for mouse-adapted EBOV (A) and SUDV (B) challenges with antibody treatment. Mice were treated with a single post-exposure dose (200 μg at 24 hours) for EBOV or two post-exposure doses (500 μg at days +1 and +4) for SUDV. Statistical p-values are listed against PBS and F4 controls for EBOV and against Z.6D8 control for SUDV (**, p<0.0001; , p<0.01; *, p<0.05; p-values greater that 0.05 are listed numerically; na, not applicable). (C and D) Rechallenge of surviving mice from initial challenge cohorts, with no further antibody treatment.

DETAILED DESCRIPTION OF THE INVENTION

Herein is described A composition is provided comprising (1) a first single chain variable fragment (scFv) comprising at least one CDR directed to a membrane glycoprotein pre-fusion core of a first species of filovirus, which first scFv is covalently joined to (2) a first polypeptide of an immunoglobulin G (IgG) comprising at least one CDR directed to a membrane glycoprotein pre-fusion core of a second species of filovirus, wherein the first species of filovirus and second species of filovirus are different species.

In an embodiment of the composition, the first scFv comprises three different heavy chain CDRs and three different light chain CDRs, each CDR directed to the membrane glycoprotein pre-fusion core of the first species of filovirus.

In an embodiment of the composition, the IgG comprises at least three different heavy chain CDRs and at least three different light chain CDRs, each CDR directed to the membrane glycoprotein pre-fusion core of the second species of filovirus.

In an embodiment of the compositions, the first scFv is covalently joined at its N terminal to a C terminal of a first polypeptide of the IgG. In an embodiment of the compositions, the first polypeptide of the IgG is a heavy chain. In an embodiment of the compositions, the first polypeptide of the IgG is a light chain.

In an embodiment of the compositions, the first scFv is covalently joined at its C terminal to an N terminal of a first polypeptide of the IgG. In an embodiment of the compositions, the first polypeptide of the IgG is a heavy chain. In an embodiment of the compositions, the first polypeptide of the IgG is a light chain.

In an embodiment of the compositions, the scFv is covalently joined to the first polypeptide via a polypeptide linker.

In an embodiment of the compositions, the polypeptide linker comprises the sequence GGSAGSAGSAGSGGS (SEQ ID NO:17).

In an embodiment of the compositions, a $V_H$ sequence of the first scFv has a sequence identical to $V_H$ sequence of a human or a humanized antibody directed to the membrane glycoprotein pre-fusion core of the first species of filovirus.

In an embodiment of the compositions, a $V_L$ sequence of the first scFv has a sequence identical to $V_L$ sequence of a human or a humanized antibody directed to the membrane glycoprotein pre-fusion core of the first species of filovirus.

In an embodiment of the compositions, the $V_H$ sequence of the scFv is joined to the $V_L$ sequence of the first scFv by a polypeptide linker. In an embodiment of the compositions, the polypeptide linker is majority glycine residues. In an embodiment of the compositions, the polypeptide linker is GGGGSGGGGSGGGGS (SEQ ID NO:18).

In an embodiment of the compositions, the composition comprises a second scFv, wherein the second scFv is covalently joined to a second polypeptide of the IgG. In an embodiment of such compositions, a $V_L$ sequence of the first scFv has a sequence identical to $V_L$ sequence of a human or a humanized antibody directed to the membrane glycoprotein pre-fusion core of the first species of filovirus. In an embodiment of the compositions, a $V_H$ sequence of the IgG has a sequence identical to $V_H$ sequence of a human or a humanized IgG antibody directed to the membrane glycoprotein pre-fusion core of the second species of filovirus. In an embodiment of the compositions, a $V_L$ sequence of the IgG has a sequence identical to $V_L$ sequence of a human or a humanized IgG antibody directed to the membrane glycoprotein pre-fusion core of the second species of filovirus.

In an embodiment of the compositions, the IgG is a neutralizing antibody for the second species of filovirus.

In an embodiment of the compositions, the first species of filovirus and the second species of filovirus are both *Ebolavirus* species. In an embodiment of the compositions, the Ebola virus species are *Zaire ebolavirus* and *Sudan ebolavirus*.

A composition is also provided comprising (i) a first single chain variable fragment (scFv) comprising at least one CDR directed to a membrane glycoprotein pre-fusion core of a first species of filovirus, which first scFv is covalently joined to (ii) a first polypeptide of an immunoglobulin G (IgG) comprising at least one CDR directed to a membrane glycoprotein pre-fusion core of a second species of filovirus, the IgG having covalently joined thereto, at a different location from the attachment of (i) thereto, (iii) a second single chain variable fragment (scFv) comprising at least one CDR directed to a membrane glycoprotein pre-fusion core of a third species of filovirus, wherein the first species of filovirus and second species of filovirus and third species of filovirus are all different species.

In an embodiment of the composition, the first scFv comprises three different heavy chain CDRs and three different light chain CDRs, each CDR directed to the membrane glycoprotein pre-fusion core of the first species of filovirus, and the second scFv comprises three different heavy chain CDRs and three different light chain CDRs, each CDR directed to the membrane glycoprotein pre-fusion core of the third species of filovirus. In an embodiment of the composition, the IgG comprises at least three different heavy chain CDRs and at least three different light chain CDRs, each CDR directed to the membrane glycoprotein pre-fusion core of the second species of filovirus.

In an embodiment of the compositions, the first scFv is covalently joined at its N terminal to a C terminal of a first polypeptide of the IgG, and the second scFv is covalently joined to a different location on the IgG. In an embodiment of the compositions, the first polypeptide of the IgG is a heavy chain. In an embodiment of the compositions, the first polypeptide of the IgG is a light chain.

In an embodiment of the compositions, the first scFv is covalently joined at its C terminal to an N terminal of a first polypeptide of the IgG, and the second scFv is covalently joined to a different location on the IgG. In an embodiment of the compositions, the first polypeptide of the IgG is a heavy chain. In an embodiment of the compositions, the first polypeptide of the IgG is a light chain.

In an embodiment of the compositions, the first and second scFvs are each covalently joined to the first polypeptide, each via a separate polypeptide linker. In an embodiment of the compositions, the first and second scFvs are each covalently joined to different polypeptides of the IgG, each via a separate polypeptide linker. In an embodiment of the compositions, the polypeptide linkers each comprise the sequence

GGSAGSAGSAGSGGS. (SEQ ID NO: 17)

In an embodiment of the compositions, a $V_H$ sequence of the first scFv has a sequence identical to $V_H$ sequence of a human or a humanized antibody directed to the membrane glycoprotein pre-fusion core of the first species of filovirus. In an embodiment of the compositions, a $V_H$ sequence of the second scFv has a sequence identical to $V_H$ sequence of a human or a humanized antibody directed to the membrane glycoprotein pre-fusion core of the third species of filovirus.

In an embodiment of the compositions, a $V_L$ sequence of the first scFv has a sequence identical to $V_L$ sequence of a human or a humanized antibody directed to the membrane glycoprotein pre-fusion core of the first species of filovirus. In an embodiment of the compositions, a $V_L$ sequence of the second scFv has a sequence identical to $V_L$ sequence of a human or a humanized antibody directed to the membrane glycoprotein pre-fusion core of the third species of filovirus.

In an embodiment of the compositions, the VH sequence of the first scFv is joined to the VL sequence of the scFv by a polypeptide linker. In an embodiment of the compositions, the VH sequence of the second scFv is joined to the VL sequence of the scFv by a polypeptide linker. In an embodiment of the compositions, the polypeptide linker is majority glycine residues. In an embodiment of the compositions, the polypeptide linker is

GGGGSGGGGSGGGGS. (SEQ ID NO: 18)

In an embodiment of the compositions, the IgG is a neutralizing antibody for the second species of filovirus.

In an embodiment of the compositions, the first species of filovirus and the second species of filovirus and third species of filovirus are all *Ebolavirus* species. In an embodiment of the compositions, the *Ebola* virus species include *Zaire ebolavirus* and *Sudan ebolavirus*. In an embodiment of the compositions, the at least one species of filovirus and is an *Ebolavirus* species and at least one species of filovirus is a *Marburg* virus.

Also provided is an isolated nucleic acid encoding any of the compositions described herein.

Also provided is a method of treating a filovirus infection in a subject comprising administering an amount of a bispecific composition described herein to the subject effective to treat a filovirus infection in a subject.

Also provided is a method of preventing a filovirus infection in a subject comprising administering an amount of a bispecific composition described herein to the subject effective to inhibit a filovirus infection in a subject.

Also provided is a method of preventing a filovirus infection of a mammalian cell comprising contacting the filovirus with an amount of a bispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human.

Also provided is a method of treating a filovirus infection in a subject comprising administering an amount of a trispecific composition described herein to the subject effective to treat a filovirus infection in a subject.

Also provided is a method of preventing a filovirus infection in a subject comprising administering an amount of a trispecific composition described herein to the subject effective to inhibit a filovirus infection in a subject.

Also provided is a method of preventing a filovirus infection of a mammalian cell comprising contacting the filovirus with an amount of a trispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human.

Also provided is a method of treating a filovirus infection in a subject comprising administering an amount of a bispecific composition described herein to the subject effective to treat a filovirus infection in a subject. Also provided is a method of preventing a filovirus infection in a subject comprising administering an amount of a bispecific composition described herein to the subject effective to inhibit a filovirus infection in a subject. Also provided is a method of preventing a filovirus infection of a mammalian cell comprising contacting the filovirus with an amount of a bispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human. Also provided is a method of treating a filovirus infection in a subject comprising administering an amount of a trispecific composition described herein to the subject effective to treat a filovirus infection in a subject. Also provided is a method of preventing a filovirus infection in a subject comprising administering an amount of a trispecific composition described herein to the subject effective to inhibit a filovirus infection in a subject. Also provided is a method of preventing a filovirus infection of a mammalian cell comprising contacting the filovirus with an amount of a trispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human. In an embodiment of all of the methods described herein, the subject is human.

Also provided is a portion of an recombinant dual-variable-domain antibody, the portion comprising:
(1) a heavy chain amino acid sequence comprising in N terminal to C terminal order (i) a first $V_H$ amino acid sequence comprising at least one CDR directed to a membrane glycoprotein pre-fusion core of a first species of filovirus, (ii) a 4, 5, 6, 7, or 8 amino acid first linker sequence, (iii) a second $V_H$ amino acid sequence comprising at least one CDR directed to a membrane glycoprotein pre-fusion core of a second species of filovirus, (iv) an immunoglobulin G $C_H1$ amino acid sequence, (v) an immunoglobulin G hinge amino acid sequence, (vi) an immunoglobulin G $C_H2$ amino acid sequence, (vii) an immunoglobulin G $C_H3$ amino acid sequence, which is bound via one or more inter-chain disulfide bond(s) to (2) a light chain amino acid sequence comprising in N terminal to C terminal order (i) a first $V_L$ amino acid sequence comprising at least one CDR directed to a membrane glycoprotein pre-fusion core of a first species of filovirus, (ii) a 4, 5, 6, 7, or 8 amino acid second linker sequence, (iii) a second $V_L$ amino acid sequence comprising at least one CDR directed to a membrane glycoprotein pre-fusion core of a second species of filovirus, (iv) an immunoglobulin G $C_L$ amino acid sequence, wherein the first species of filovirus and second species of filovirus are different species.

In an embodiment, (1) and (2) are bound via an inter-chain disulfide bond between the $C_H1$ amino acid sequence and the $C_L$ amino acid sequence. Also provided is a construct comprising two of the recombinant dual-variable-domain antibodies (or portions) as described together by one or more disulfide bonds between the heavy chain amino acid sequence of each. In an embodiment, the two recombinant dual-variable-domain antibodies are joined together by two disulfide bonds between the immunoglobulin G hinge amino acid sequences of each. In an embodiment, the 4, 5, 6, 7, or 8 amino acid first linker sequence is a 6 amino acid first linker sequence. In an embodiment, the 6 amino acid first linker sequence is ASTKGP (SEQ ID NO:41). In an embodiment, the 4, 5, 6, 7, or 8 amino acid second linker sequence is 5 amino acid second linker sequence. In an embodiment, the 5 amino acid second linker sequence is TVAAP (SEQ ID NO:42).

In an embodiment, the first $V_H$ amino acid sequence comprises three different heavy chain CDRs each of the three CDRs directed to the membrane glycoprotein pre-fusion core of the first species of filovirus. In an embodiment, the first $V_L$ amino acid sequence comprises three different light chain CDRs each of the three CDRs directed to the membrane glycoprotein pre-fusion core of the first species of filovirus. In an embodiment, the second $V_H$ amino acid sequence comprises three different heavy chain CDRs each of the three CDRs directed to the membrane glycoprotein pre-fusion core of the second species of filovirus. In an embodiment, the second $V_L$ amino acid sequence comprises three different light chain CDRs each of the three CDRs directed to the membrane glycoprotein pre-fusion core of the second species of filovirus.

In an embodiment, the first species of filovirus and the second species of filovirus are both *Ebolavirus* species. In an embodiment, the *Ebola* virus species are *Zaire ebolavirus* and *Sudan ebolavirus*.

Also provided is an isolated nucleic acid encoding a recombinant dual-variable-domain antibody or a construct as described herein. In an embodiment, the isolated nucleic acid is, or comprises, a cDNA.

Also provided is a method of treating a filovirus infection in a subject comprising administering an amount of the recombinant dual-variable-domain antibody or construct described herein to the subject effective to treat a filovirus infection in a subject. Also provided is a method of preventing a filovirus infection in a subject comprising administering an amount of the recombinant dual-variable-domain antibody or construct described herein to the subject effective to inhibit a filovirus infection in a subject. Also provided is a method of preventing a filovirus infection of a mammalian cell comprising contacting the filovirus with an amount of the recombinant dual-variable-domain antibody or construct described herein effective to inhibit a filovirus infection of a mammalian cell. In an embodiment, the cell is an antigen presenting cell. In an embodiment, the cell is a dendritic cell or a macrophage. In an embodiment, the cell is human.

In an embodiment of all of the methods described herein, the subject is human.

As used herein, "treating" a specified condition means ameliorating one or more symptoms of an extant condition, for example, a filovirus infection.

As used herein, "preventing" a specified condition means reducing the development of, or reducing the extent of, one or more symptoms of the condition, for example a filovirus infection, as compared to the development or extent the condition takes in the absence of preventative treatment. In an embodiment, "preventing" as used herein does not mean an absolute prevention, but a lessened extent of the condition brought about prophylactically.

Exemplary E10/F4-KZ52 scFv Bispecifics Sequences: the following exemplary amino acid sequences are provided, for the compositions of the invention as relating to the embodiments of antibodies E10 and F4, with non-limiting exemplary nucleotide sequences (in view of the degeneracy of the genetic code).

E10-KZ52 HC N' Fusion Sequence:

```
Amino Acid (SEQ ID NO: 1):
EVQLLESGGGLVKPGGSLRLSCAASGFTLINYRMNWVRQAPGKGLEWVSS

ISSSSSYIHYADSVKGRFTISRDNAENSLYLQMNSLRAEDTAVYYCVREG

PRATGYSMADVFDIWGQGTMVTVSSGGGGSGGGGSGGGGSELVMTQSPDS

LAVSLGERATINCKSSQSVLYSSNNKSYLAWYQQKPGQPPKLLIYWASTR

ESGVPDRFSGSGSGTDFTLTISSLQAEDVAVYYCQQYYSAPLTFGGGTKV

EIKGGSAGSAGSAGSGGSEVQLVESGGGLVQPGGSLRLSCAASGFAFNYY

DIHWVRQAPGKGLEWVAYINPGGGNTYYADSVKGRFTISADTSKNTAYLQ

MNSLRAEDTAVYYCARQLYGNSFMDYWGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCDKTH

TCPPCPAPELLGRPSVFLEPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYP

SDIAVEWESNGQPENNYKTTPPVLDSDGSFELYSKLTVDKSRWQQGNVFS

CSVMHEALHNHYTQKSLSLSPGK
```

Underlined region is glycine-rich linker polypeptide. Bold region is fusion linker polypeptide. Italicized region is CH1-CH3 for the HC and the CL region.

Nucleotide (SEQ ID NO: 2):
GAAGTGCAGTTACTGGAAAGCGGCGGCGGCCTGGTTAAACCTGGCGGTAGTCT

GCGTCTGAGTTGCGCCGCCAGCGGTTTCACCCTGATCAACTACCGCATGAACTG

GGTGCGTCAGGCACCGGGTAAAGGCCTGGAGTGGGTGAGCAGCATTAGCAGCA

GCAGCAGCTATATTCACTACGCCGACAGCGTGAAAGGCCGCTTTACCATCAGCC

GCGACAATGCCGAGAACAGTCTGTATCTGCAGATGAACAGCCTAAGGGCGGAA

GATACAGCCGTGTACTACTGTGTGCGCGAAGGCCCTCGCGCAACCGGCTATAGC

ATGGCAGACGTGTTTGATATCTGGGGTCAGGGCACCATGGTTACAGTTAGCAGT

GGTGGTGGTGGTAGTGGTGGCGGTGGTAGCGGTGGTGGTGGCAGTGAACTGGT

GATGACCCAGAGCCCGGATAGCTTAGCCGTGAGTCTGGGCGAAAGGGCGACCA

TTAACTGCAAAAGCAGCCAGAGCGTGCTGTACAGCAGCAACAACAAGAGCTAC

CTGGCATGGTATCAGCAAAAACCGGGTCAGCCTCCGAAACTGCTGATCTATTGG

GCAAGCACCCGCGAAAGTGGTGTTCCGGATCGCTTCAGCGGTAGTGGCAGCGG

TACCGATTTCACCCTGACCATCAGCAGTCTGCAGGCCGAGGACGTTGCAGTGTA

TTACTGTCAGCAGTACTACAGCGCCCCGCTGACCTTTGGCGGCGGCACCAAAGT

TGAAATTAAGGGCGGCAGTGCAGGCAGCGCCGGTAGTGCCGGTAGTGGTGGTA

GCGAAGTTCAGCTGGTTGAAAGTGGCGGCGGTCTGGTGCAGCCTGGTGGTAGTC

TGCGTCTGAGTTGTGCCGCCAGCGGCTTTGCCTTCAATTACTATGACATTCATTG

GGTTCGCCAGGCCCCGGGTAAAGGTCTGGAATGGGTTGCATATATCAACCCGG

GTGGCGGTAACACCTACTATGCCGACAGCGTTAAGGGTCGCTTCACCATCAGCG

CAGATACCAGCAAAAACACCGCCTACCTGCAGATGAATAGCCTGCGTGCAGAA

GATACCGCCGTTTACTACTGTGCCCGCCAGCTGTACGGCAATAGCTTCATGGAC

TATTGGGGCCAGGGCACCTTAGTTACCGTGAGCAGC

Combined (SEQ ID NO: 1 and 2):
gaagtgcagttactggaaagcggcggcggcctggttaaacctggcggtagtctgcgtctg
 E   V   Q   L   L   E   S   G   G   G   L   V   K   P   G   G   S   L   R   L agttgcgccgccagcggtttcaccctgatcaactaccgcatgaactgggtgcgtcaggca
 S   C   A   A   S   G   F   T   L   I   N   Y   R   M   N   W   V   R   Q   A ccgggtaaaggcctggagtgggtgagcagcattagcagcagcagcagctatattcactac
 P   G   K   G   L   E   W   V   S   S   I   S   S   S   S   S   Y   I   H   Y gccgacagcgtgaaaggccgctttaccatcagccgcgacaatgccgagaacagtctgtat
 A   D   S   V   K   G   R   F   T   I   S   R   D   N   A   E   N   S   L   Y ctgcagatgaacagcctaagggcggaagatacagccgtgtactactgtgtgcgcgaaggc
 L   Q   M   N   S   L   R   A   E   D   T   A   V   Y   Y   C   V   R   E   G cctcgcgcaaccggctatagcatggcagacgtgtttgatatctggggtcagggcaccatg
 P   R   A   T   G   Y   S   M   A   D   V   F   D   I   W   G   Q   G   T   M gttacagttagcagtggtggtggtggtagtggtggcggtggtagcggtggtggtggcagt
 V   T   V   S   S   G   G   G   G   S   G   G   G   G   S   G   G   G   G   S gaactggtgatgacccagagcccggatagcttagccgtgagtctgggcgaaagggcgacc
 E   L   V   M   T   Q   S   P   D   S   L   A   V   S   L   G   E   R   A   T attaactgcaaaagcagccagagcgtgctgtacagcagcaacaacaagagctacctggca
 I   N   C   K   S   S   Q   S   V   L   Y   S   S   N   N   K   S   Y   L   A tggtatcagcaaaaaccgggtcagcctccgaaactgctgatctattgggcaagcacccgc
 W   Y   Q   Q   K   P   G   Q   P   P   K   L   L   I   Y   W   A   S   T   R gaaagtggtgttccggatcgcttcagcggtagtggcagcggtaccgatttcaccctgacc
 E   S   G   V   P   D   R   F   S   G   S   G   S   G   T   D   F   T   L   T atcagcagtctgcaggccgaggacgttgcagtgtattactgtcagcagtactacagcgcc
 I   S   S   L   Q   A   E   D   V   A   V   Y   Y   C   Q   Q   Y   Y   S   A

```
ccgctgacctttggcggcggcaccaaagttgaaattaagggcggcagtgcaggcagcgcc
 P  L  T  F  G  G  G  T  K  V  E  I  K  G  G  S  A  G  S  A ggtagtgccggtagtggtggtagcgaagttcagctggttgaaagtggcggcggtctggtg
 G  S  A  G  S  S  E  V  E  V  Q  L  V  E  S  G  G  G  L  V cagcctggtggtagtctgcgtctgagttgtgccgccagcggctttgccttcaattactat
 Q  P  G  G  S  L  R  L  S  C  A  A  S  G  F  A  F  N  Y  Y gacattcattgggttcgccaggcccccgggtaaaggtctggaatgggttgcatatatcaac
 D  I  H  W  V  R  Q  A  P  G  K  G  L  E  W  V  A  Y  I  N ccgggtggcggtaacacctactatgccgacagcgttaagggtcgcttcaccatcagcgca
 P  G  G  N  T  Y  Y  A  D  S  V  K  G  R  F  T  I  S  A gataccagcaaaaacaccgcctacctgcagatgaatagcctgcgtgcagaagataccgcc
 D  T  S  K  N  T  A  Y  L  Q  M  N  S  L  R  A  E  D  T  A gtttactactgtgcccgccagctgtacggcaatagcttcatggactattggggccagggc
 V  Y  Y  C  A  R  Q  L  Y  G  N  S  F  M  D  Y  W  G  Q  G accttagttaccgtgagcagc
 T  L  V  T  V  S  S
```

E10-KZ52 LC N' Fusion Sequence:

Amino Acid (SEQ ID NO: 3):
EVQLLESGGGLVKPGGSLRLSCAASGFTLINYRMNWVRQAPGKGLEWVSS
ISSSSSYIHYADSVKGRFTISRDNAENSLYLQMNSLRAEDTAVYYCVREG
PRATGYSMADVFDIWGQGTMVTVSSGGGGSGGGGSGGGGSELVMTQSPDS
LAVSLGERATINCKSSQSVLYSSNNKSYLAWYQQKPGQPPKLLIYWASTR
ESGVPDRFSGSGSGTDFTLTISSLQAEDVAVYYCQQYYSAPLTFGGGTKV -continued

EIKGGSAGSAGSAGSGGSDIQMTQSPSSLSASVGDRVTITCRASQDVTTA

VAWYQQKPGKAPKLLIYWASRLHNGVPSRFSGSGSGTDFTLTISSLQPED

FATYYCQQHYSTPLTFGQGTKVEIK*RTVAAPSVFIFPPSDEQLKSGTASV*

*VCLLNNFYPREAKVQWKVDNALQSGNSQESVTEQDSKDSTYSLSSTLTLS*

*KADYEKHKVYACEVTHQGLSSPVTKSFNRGECGGSDYKDDDDK*

Underlined region is glycine-rich linker polypeptide. Bold region is fusion linker polypeptide. Italicized region is CH1-CH3 for the HC and the CL region.

Nucleotide (SEQ ID NO: 4):
GAAGTGCAGCTGCTGGAAAGCGGTGGCGGTCTGGTTAAACCTGGCGGTAGTCT

GCGCCTGAGTTGCGCCGCCAGCGGTTTTACACTGATCAACTATCGCATGAACTG

GGTGCGTCAGGCACCGGGTAAGGGTCTGGAGTGGGTTAGCAGCATTAGTAGCA

GCAGCAGTTACATTCACTACGCCGATAGCGTGAAAGGCCGCTTCACAATTAGCC

GCGATAACGCCGAGAACAGCCTGTATCTGCAGATGAACAGTTTACGCGCCGAA

GATACCGCCGTGTATTATTGCGTTCGCGAAGGTCCGCGTGCAACCGGCTACAGC

ATGGCCGACGTTTTCGATATTTGGGGTCAGGGCACCATGGTGACAGTTAGTAGC

GGTGGTGGTGGTAGTGGTGGTGGCGGCAGCGGTGGTGGTGGTAGTGAACTGGT

GATGACCCAGAGCCCGGATAGCCTGGCAGTGAGCCTGGGTGAGCGTGCCACCA

TCAATTGCAAAAGCAGCCAGAGCGTGCTGTACAGCAGCAACAACAAGAGTTAC

CTGGCCTGGTACCAACAGAAACCGGGCCAGCCGCCGAAACTGCTGATTTATTGG

GCCAGTACCCGCGAAAGCGGCGTGCCTGATCGTTTTAGTGGCAGCGGTAGCGG

CACCGACTTTACCCTGACCATTAGCAGCCTGCAGGCCGAGGATGTGGCAGTGTA

TTACTGCCAGCAGTATTACAGCGCCCCGTTAACCTTTGGCGGCGGTACCAAAGT

GGAGATCAAAGGTGGCAGTGCAGGCAGCGCCGGTAGTGCAGGTAGTGGTGGTA

GCGACATCCAGATGACACAGAGTCCGAGCAGCCTGAGTGCCAGCGTTGGTGAC

CGTGTGACCATTACCTGCCGTGCCAGCCAGGATGTTACCACAGCCGTTGCATGG

TATCAGCAGAAGCCGGGTAAGGCCCCTAAGTTACTGATCTACTGGGCAAGCCG

-continued

```
CCTGCATAACGGTGTGCCGAGCCGCTTTAGCGGCAGTGGTAGCGGTACCGATTT

CACCCTGACCATCAGCAGTCTGCAGCCGGAAGATTTCGCAACCTACTACTGTCA

GCAGCATTACAGCACCCCGCTGACCTTTGGCCAGGGCACCAAAGTGGAAATTA

AA

Combined (SEQ ID NO: 3 and 4):
gaagtgcagctgctggaaagcggtggcggtctggttaaacctggcggtagtctgcgcctg
 E  V  Q  L  L  E  S  G  G  G  L  V  K  P  G  G  S  L  R  L agttgcgccgccagcggttttacactgatcaactatcgcatgaactgggtgcgtcaggca
 S  C  A  A  S  G  F  T  L  I  N  Y  R  M  N  W  V  R  Q  A ccgggtaagggtctggagtgggttagcagcattagtagcagcagcagttacattcactac
 P  G  K  G  L  E  W  V  S  S  I  S  S  S  S  S  Y  I  H  Y gccgatagcgtgaaaggccgcttcacaattagccgcgataacgccgagaacagcctgtat
 A  D  S  V  K  G  R  F  T  I  S  R  D  N  A  E  N  S  L  Y ctgcagatgaacagtttacgcgccgaagataccgccgtgtattattgcgttcgcgaaggt
 L  Q  M  N  S  L  R  A  E  D  T  A  V  Y  Y  C  V  R  E  G ccgcgtgcaaccggctacagcatggccgacgttttcgatatttggggtcagggcaccatg
 P  R  A  T  G  Y  S  M  A  D  V  F  D  I  W  G  Q  G  T  M gtgacagttagtagcggtggtggtggtagtggtggtggcggcagcggtggtggtggtagt
 V  T  V  S  S  G  G  G  G  S  G  G  G  G  S  G  G  G  G  S gaactggtgatgacccagagcccggatagcctggcagtgagcctgggtgagcgtgccacc
 E  L  V  M  T  Q  S  P  D  S  L  A  V  S  L  G  E  R  A  T atcaattgcaaaagcagccagagcgtgctgtacagcagcaacaacaagagttacctggcc
 I  N  C  K  S  S  Q  S  V  L  Y  S  S  N  N  K  S  Y  L  A tggtaccaacagaaaccgggccagccgccgaaactgctgatttattgggccagtacccgc
 W  Y  Q  Q  K  P  G  Q  P  P  K  L  L  I  Y  W  A  S  T  R gaaagcggcgtgcctgatcgttttagtggcagcggtagcggcaccgactttaccctgacc
 E  S  G  V  P  D  R  F  S  G  S  G  S  G  T  D  F  T  L  T attagcagcctgcaggccgaggatgtggcagtgtattactgccagcagtattacagcgcc
 I  S  S  L  Q  A  E  D  V  A  V  Y  Y  C  Q  Q  Y  Y  S  A ccgttaacctttggcggcggtaccaaagtggagatcaaaggtggcagtgcaggcagcgcc
 P  L  T  F  G  G  G  T  K  V  E  I  K  G  G  S  A  G  S  A ggtagtgcaggtagtggtggtagcgacatccagatgacacagagtccgagcagcctgagt
 G  S  A  G  S  G  G  S  D  I  Q  M  T  Q  S  P  S  S  L  S gccagcgttggtgaccgtgtgaccattacctgccgtgccagccaggatgttaccacagcc
 A  S  V  G  D  R  V  T  I  T  C  R  A  S  Q  D  V  T  T  A gttgcatggtatcagcagaagccgggtaaggcccctaagttactgatctactgggcaagc
 V  A  W  Y  Q  Q  K  P  G  K  A  P  K  L  L  I  Y  W  A  S cgcctgcataacggtgtgccgagccgctttagcggcagtggtagcggtaccgatttcacc
 R  L  H  N  G  V  P  S  R  F  S  G  S  G  S  G  T  D  F  T ctgaccatcagcagtctgcagccggaagatttcgcaacctactactgtcagcagcattac
 L  T  I  S  S  L  Q  P  E  D  F  A  T  Y  Y  C  Q  Q  H  Y agcaccccgctgacctttggccagggcaccaaagtggaaattaaa
 S  T  P  L  T  F  G  Q  G  T  K  V  E  I  K
```

E10-KZ52 HC C' Fusion Sequence:

```
Amino Acid (SEQ ID NO: 5):
EVQLVESGGGLVQPGGSLRLSCAASGFAFNYYDIHWVRQAPGKGLEWVAY

INPGGGNTYYADSVKGRFTISADTSKNTAYLQMNSLRAEDTAVYYCARQL

YGNSFFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCDKTHTCPPCPAPELLGRPSVFL
```

-continued

```
FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSLS

LSPGKGGSAGSAGSAGSGGSEVQLLESGGGLVKPGGSLRLSCAASGFTLI

NYRMNWVRQAPGKGLEWVSSISSSSSYIHYADSVKGRFTISRDNAENSLY
```

-continued

LQMNSLRAEDTAVYYCVREGPRATGYSMADVFDIWGQGTMVTVSS<u>GGGGS</u>
<u>GGGGSGGGGS</u>ELVMTQSPDSLAVSLGERATINCKSSQSVLYSSNNKSYLA
WYQQKPGQPPKLLIYWASTRESGVPDRFSGSGSGTDFTLTISSLQAEDVA
VYYCQQYYSAPLTFGGGTKVEIK

Underlined region is linker polypeptide. Bold region is fusion linker polypeptide.

```
Nucleotide (SEQ ID NO: 6):
GAGGTTCAGCTGGTGGAGTCTGGCGGTGGCCTGGTGCAGCCAGGGGGCTCACT
CCGTTTGTCCTGTGCAGCTTCTGGCTTCGCGTTTAACTATTATGATATTCATTGG
GTGCGTCAGGCCCCGGGTAAGGGCCTGGAATGGGTTGCATATATTAACCCGGG
CGGTGGCAACACCTATTATGCTGATAGCGTCAAGGGCCGTTTCACTATAAGCGC
AGACACATCCAAAAACACAGCCTACCTACAAATGAACAGCTTAAGAGCTGAGG
ACACTGCCGTCTATTATTGTGCTCGCCAGCTGTATGGCAACAGCTTTATGGACT
ACTGGGGTCAAGGAACCCTGGTCACCGTCTCCTCGGCTAGCACCAAGGGTCCGA
GCGTGTTTCCTCTGGCACCTAGCAGTAAAAGCACCAGTGGTGGTACAGCAGCCC
TGGGTTGCCTGGTGAAGGATTACTTTCCGGAGCCGGTGACCGTTAGTTGGAATA
GCGGCGCCCTGACCAGTGGCGTTCATACATTTCCGGCCGTGCTGCAGAGTAGTG
GCCTGTACAGCCTGAGTAGCGTTGTTACCGTTCCGAGCAGCAGCCTGGGCACCC
AGACCTATATTTGCAATGTTAACCATAAACCGAGCAACACAAAAGTTGATAAA
AAAGTTGAACCGAAGAGCTGTGACAAAACCCATACATGTGACAAAACACACAC
CTGCCCGCCTTGTCCGGCACCTGAGCTGCTGGGTCGCCCGAGCGTTTTTCTGTTT
CCTCCGAAACCGAAAGACACC[...]ACCCAGAAGAGTCTGAGCCTGAGTCCTGGC
AAAGGTGGATCCGCCGGTAGCGCAGGTAGTGCAGGTAGTGGCGGCAGCGAAGT
TCAGCTGTTAGAAAGTGGCGGTGGTCTGGTTAAGCCGGGCGGTAGTCTGCGCCT
GAGCTGTGCAGCAAGTGGTTTCACCCTGATCAATTATCGTATGAACTGGGTGCG
CCAAGCCCCGGGTAAAGGTCTGGAGTGGGTTAGTAGTATCAGCAGCAGCAGCA
GTTACATCCACTATGCCGATAGCGTTAAGGGCCGCTTTACAATCAGCCGCGATA
ATGCCGAGAATAGCTTATACCTGCAAATGAACAGTCTAAGGGCGGAAGATACC
GCCGTTTACTACTGCGTTCGTGAAGGCCCTCGCGCAACAGGCTATAGCATGGCA
GACGTGTTCGACATTTGGGGTCAGGGCACCATGGTGACCGTTAGTAGCGGCGGT
GGTGGTAGTGGTGGTGGCGGTAGTGGTGGCGGTGGCAGCGAACTGGTGATGAC
CCAGAGTCCGGATAGCCTGGCCGTGAGCTTAGGCGAGCGTGCAACCATTAATTG
TAAAAGCAGTCAGAGTGTTCTGTATAGTAGCAATAACAAGAGCTATCTGGCCTG
GTATCAGCAGAAGCCGGGCCAGCCGCCGAAACTGCTGATTTACTGGGCAAGCA
CCCGCGAAAGTGGCGTGCCTGATCGCTTTAGTGGTAGCGGCAGCGGCACCGATT
TTACCCTGACCATTAGCAGTCTGCAGGCCGAGGACGTTGCCGTTTATTACTGCC
AGCAGTACTATAGCGCACCGCTGACATTTGGCGGTGGCACCAAGGTGGAAATT
AAATAA Combined (SEQ ID NO: 5 and 6):
gaggttcagctggtggagtctggcggtggcctggtgcagccaggggggctcactccgtttg
 E  V  Q  L  V  E  S  G  G  G  L  V  Q  P  G  G  S  L  R  L tcctgtgcagcttctggcttcgcgtttaactattatgatattcattgggtgcgtcaggcc
 S  C  A  A  S  G  F  A  F  N  Y  Y  D  I  H  W  V  R  Q  A ccgggtaagggcctggaatgggttgcatatattaacccgggcggtggcaacacctattat
 P  G  K  G  L  E  W  V  A  Y  I  N  P  G  G  N  T  Y  Y
```

```
gctgatagcgtcaagggccgtttcactataagcgcagacacatccaaaaacacagcctac
 A  D  S  V  K  G  R  F  T  I  S  A  D  T  S  K  N  T  A  Y ctacaaatgaacagcttaagagctgaggacactgccgtctattattgtgctcgccagctg
 L  Q  M  N  S  L  R  A  E  D  T  A  V  Y  Y  C  A  R  Q  L tatggcaacagctttatggactactggggtcaaggaaccctggtcaccgtctcctcggct
 Y  G  N  S  F  M  D  Y  W  G  Q  G  T  L  V  T  V  S  S  A agcaccaagggtccgagcgtgtttcctctggcacctagcagtaaaagcaccagtggtggt
 S  T  K  G  P  S  V  F  P  L  A  P  S  S  K  S  T  S  G  G acagcagccctgggttgcctggtgaaggattactttccggagccggtgaccgttagttgg
 T  A  A  L  G  C  L  V  K  D  Y  F  P  E  P  V  T  V  S  W aatagcggcgccctgaccagtggcgttcatacatttccggccgtgctgcagagtagtggc
 N  S  G  A  L  T  S  G  V  H  T  F  P  A  V  L  Q  S  S  G ctgtacagcctgagtagcgttgttaccgttccgagcagcagcctgggcacccagacctat
 L  Y  S  L  S  S  V  V  T  V  P  S  S  S  L  G  T  Q  T  Y atttgcaatgttaaccataaaccgagcaacacaaaagttgataaaaaagttgaaccgaag
 I  C  N  V  N  H  K  P  S  N  T  K  V  D  K  K  V  E  P  K agctgtgacaaaacccatacatgtgacaaaacacacacctgcccgccttgtccggcacct
 S  C  D  K  T  H  T  C  D  K  T  H  T  C  P  P  C  P  A  P gagctgctgggtcgcccgagcgttttctgtttcctccgaaaccgaaagacacc [...]
 E  L  L  G  R  P  S  V  F  L  F  P  P  K  P  K  D  T  [...]

acccagaagagtctgagcctgagtcctggcaaaggtggatccgccggtagcgcaggtagt
 T  Q  K  S  L  S  L  S  P  G  K  G  G  S  A  G  S  A  G  S gcaggtagtggcggcagcgaagttcagctgttagaaagtggcggtggtctggttaagccg
 A  G  S  G  G  S  E  V  Q  L  L  E  S  G  G  G  L  V  K  P ggcggtagtctgcgcctgagctgtgcagcaagtggtttcacctgatcaattatcgtatg
 G  G  S  L  R  L  S  C  A  A  S  G  F  T  L  I  N  Y  R  M aactgggtgcgccaagccccgggtaaaggtctggagtgggttagtagtatcagcagcagc
 N  W  V  R  Q  A  P  G  K  G  L  E  W  V  S  S  I  S  S  S agcagttacatccactatgccgatagcgttaagggccgctttacaatcagccgcgataat
 S  S  Y  I  H  Y  A  D  S  V  K  G  R  F  T  I  S  R  D  N gccgagaatagcttatacctgcaaatgaacagtctaagggcggaagataccgccgtttac
 A  E  N  S  L  Y  L  Q  M  N  S  L  R  A  E  D  T  A  V  Y tactgcgttcgtgaaggccctcgcgcaacaggctatagcatggcagacgtgttcgacatt
 Y  C  V  R  E  G  P  R  A  T  G  Y  S  M  A  D  V  F  D  I tggggtcagggcaccatggtgaccgttagtagcggcggtggtggtagtggtggtggcggt
 W  G  Q  G  T  M  V  T  V  S  S  G  G  G  G  S  G  G  G  G agtggtggcggtggcagcgaactggtgatgacccagagtccggatagcctggccgtgagc
 S  G  G  G  G  S  E  L  V  M  T  Q  S  P  D  S  L  A  V  S ttaggcgagcgtgcaaccattaattgtaaaagcagtcagagtgttctgtatagtagcaat
 L  G  E  R  A  T  I  N  C  K  S  S  Q  S  V  L  Y  S  S  N aacaagagctatctggcctggtatcagcagaagccgggccagccgccgaaactgctgatt
 N  K  S  Y  L  A  W  Y  Q  Q  K  P  G  Q  P  P  K  L  L  I tactgggcaagcacccgcgaaagtggcgtgcctgatcgctttagtggtagcggcagcggc
 Y  W  A  S  T  R  E  S  G  V  P  D  R  F  S  G  S  G  S  G accgattttacccctgaccattagcagtctgcaggccgaggacgttgccgtttattactgc
 T  D  F  T  L  T  I  S  S  L  Q  A  E  D  V  A  V  Y  Y  C cagcagtactatagcgcaccgctgacatttggcggtggcaccaaggtggaaattaaataa
 Q  Q  Y  Y  S  A  P  L  T  F  G  G  G  T  K  V  E  I  K  -
```

E10-KZ52 LC C' Fusion Sequence:

Amino Acid (SEQ ID NO: 7):
DIQMTQSPSSLSASVGDRVTITCKASQDVTTAVAWYQQKPGKAPKLLIYW
ASRLHNGVPSRFSGSGSGTDFTLTISSLQPEDFATYYCQQHYSTPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECGGSGGSAGSAGSAGSGGSEVQLLESGGGLVKPGGSL
RLSCAASGFTLINYRMNWVRQAPGKGLEWVSSISSSSSYIHYADSVKGRF
TISRDNAENSLYLQMNSLRAEDTAVYYCVREGPRATGYSMADVFDIWGQG
TMVTVSS<u>GGGGSGGGGSGGGGS</u>ELVMTQSPDSLAVSLGERATINCKSSQS
VLYSSNNKSYLAWYQQKPGQPPKLLIYWASTRESGVPDRFSGSGSGTDFT
LTISSLQAEDVAVYYCQQYYSAPLTFGGGTKVEIK Underlined region is linker polypeptide. Bold region is fusion linker polypeptide.

Nucleotide (SEQ ID NO: 8):
GATATCCAGATGACCCAGTCCCCGAGCTCCCTGTCCGCCTCTGTGGGCGATAGG
GTCACCATCACCTGCCGGGCGAGCCAGGATGTGACCACCGCTGTAGCCTGGTAT
CAACAGAAACCAGGAAAAGCTCCGAAGCTTCTGATTTACTGGGCGAGCCGTCTT
CATAATGGCGTGCCGAGCCGCTTTAGCGGCAGCGGCTCCGGGACGGATTTCACT
CTGACCATCAGCAGTCTGCAGCCGGAAGACTTCGCAACTTATTACTGTCAGCAA
CATTATAGCACCCCGCTGACGTTCGGACAGGGTACCAAGGTGGAGATCAAACG
TACGGTGGCAGCACCGAGCGTGTTTATCTTTCCGCCGAGCGACGAACAACTGAA
AAGTGGCACAGCCAGCGTGGTGTGTTTACTGAACAACTTCTATCCTCGCGAGGC
CAAGGTGCAGTGGAAAGTGGACAATGCACTGCAGAGTGGCAATAGCCAGGAGA
GCGTGACCGAACAGGATAGCAAAGATAGCACCTATAGCCTGAGTAGCACCCTG
ACCCTGAGCAAGGCCGATTATGAGAAGCACAAGGTGTATGCATGCGAGGTTAC
CCATCAGGGCCTGAGCAGCCCGGTGACCAAAAGCTTTAACCGTGGCGAATGCG
GTGGTAGTGGTGGATCCGCCGGTAGCGCAGGTAGTGCAGGTAGTGGCGGCAGC
GAAGTTCAGCTGTTAGAAAGTGGCGGTGGTCTGGTTAAGCCGGGCGGTAGTCTG
CGCCTGAGCTGTGCAGCAAGTGGTTTCACCCTGATCAATTATCGTATGAACTGG
GTGCGCCAAGCCCCGGGTAAAGGTCTGGAGTGGGTTAGTAGTATCAGCAGCAG
CAGCAGTTACATCCACTATGCCGATAGCGTTAAGGGCCGCTTTACAATCAGCCG
CGATAATGCCGAGAATAGCTTATACCTGCAAATGAACAGTCTAAGGGCGGAAG
ATACCGCCGTTTACTACTGCGTTCGTGAAGGCCCTCGCGCAACAGGCTATAGCA
TGGCAGACGTGTTCGACATTTGGGGTCAGGGCACCATGGTGACCGTTAGTAGCG
GCGGTGGTGGTAGTGGTGGTGGCGGTAGTGGTGGCGGTGGCAGCGAACTGGTG
ATGACCCAGAGTCCGGATAGCCTGGCCGTGAGCTTAGGCGAGCGTGCAACCAT
TAATTGTAAAAGCAGTCAGAGTGTTCTGTATAGTAGCAATAACAAGAGCTATCT
GGCCTGGTATCAGCAGAAGCCGGGCCAGCCGCCGAAACTGCTGATTTACTGGG
CAAGCACCCGCGAAAGTGGCGTGCCTGATCGCTTTAGTGGTAGCGGCAGCGGC
ACCGATTTTACCCTGACCATTAGCAGTCTGCAGGCCGAGGACGTTGCCGTTTAT
TACTGCCAGCAGTACTATAGCGCACCGCTGACATTTGGCGGTGGCACCAANGTG
GAAATTAAA Combined (SEQ ID NO: 7 and 8):
gatatccagatgacccagtccccgagctccctgtccgcctctgtgggcgatagggtcacc
 D  I  Q  M  T  Q  S  P  S  S  L  S  A  S  V  G  D  R  V  T atcacctgccgggcgagccaggatgtgaccaccgctgtagcctggtatcaacagaaacca
 I  T  C  R  A  S  Q  D  V  T  T  A  V  A  W  Y  Q  Q  K  P

```
ggaaaagctccgaagcttctgatttactgggcgagccgtcttcataatggcgtgccgagc
 G  K  A  P  K  L  L  I  Y  W  A  S  R  L  H  N  G  V  P  S cgctttagcggcagcggctccgggacggatttcactctgaccatcagcagtctgcagccg
 R  F  S  G  S  G  S  G  T  D  F  T  L  T  I  S  S  L  Q  P gaagacttcgcaacttattactgtcagcaacattatagcaccccgctgacgttcggacag
 E  D  F  A  T  Y  Y  C  Q  Q  H  Y  S  T  P  L  T  F  G  Q ggtaccaaggtggagatcaaacgtacggtggcagcaccgagcgtgtttatctttccgccg
 G  T  K  V  E  I  K  R  T  V  A  A  P  S  V  F  I  F  P  P agcgacgaacaactgaaaagtggcacagccagcgtggtgtgtttactgaacaacttctat
 S  D  E  Q  L  K  S  G  T  A  S  V  V  C  L  L  N  N  F  Y cctcgcgaggccaaggtgcagtggaaagtggacaatgcactgcagagtggcaatagccag
 P  R  E  A  K  V  Q  W  K  V  D  N  A  L  Q  S  G  N  S  Q gagagcgtgaccgaacaggatagcaaagatagcacctatagcctgagtagcaccctgacc
 E  S  V  T  E  Q  D  S  K  D  S  T  Y  S  L  S  S  T  L  T ctgagcaaggccgattatgagaagcacaaggtgtatgcatgcgaggttacccatcagggc
 L  S  K  A  D  Y  E  K  H  K  V  Y  A  C  E  V  T  H  Q  G ctgagcagcccggtgaccaaaagctttaaccgtggcgaatgcggtggtagtggtggatcc
 L  S  S  P  V  T  K  S  F  N  R  G  E  C  G  G  S  G  G  S gccggtagcgcaggtagtgcaggtagtggcggcagcgaagttcagctgttagaaagtggc
 A  G  S  A  G  S  A  G  S  G  G  S  E  V  Q  L  L  E  S  G ggtggtctggttaagccgggcggtagtctgcgcctgagctgtgcagcaagtggtttcacc
 G  G  L  V  K  P  G  G  S  L  R  L  S  C  A  A  S  G  F  T ctgatcaattatcgtatgaactgggtgcgccaagcccccgggaaaggtctggagtgggtt
 L  I  N  Y  R  M  N  W  V  R  Q  A  P  G  K  G  L  E  W  V agtagtatcagcagcagcagttacatccactatgccgatagcgttaagggccgcttt
 S  S  I  S  S  S  S  Y  I  H  Y  A  D  S  V  K  G  R  F acaatcagccgcgataatgccgagaatagcttatacctgcaaatgaacagtctaagggcg
 T  I  S  R  D  N  A  E  N  S  L  Y  L  Q  M  N  S  L  R  A gaagataccgccgtttactactgcgttcgtgaaggccctcgcgcaacaggctatagcatg
 E  D  T  A  V  Y  Y  C  V  R  E  G  P  R  A  T  G  Y  S  M gcagacgtgttcgacatttggggtcagggcaccatggtgaccgttagtagcggcggtggt
 A  D  V  F  D  I  W  G  Q  G  T  M  V  T  V  S  S  G  G  G ggtagtggtggtggcggtagtggtggcggtggcagcgaactggtgatgacccagagtccg
 G  S  G  G  G  G  S  G  G  G  G  S  E  L  V  M  T  Q  S  P gatagcctggccgtgagcttaggcgagcgtgcaaccattaattgtaaaagcagtcagagt
 D  S  L  A  V  S  L  G  E  R  A  T  I  N  C  K  S  S  Q  S gttctgtatagtagcaataacaagagctatctggcctggtatcagcagaagccgggccag
 V  L  Y  S  S  N  N  K  S  Y  L  A  W  Y  Q  Q  K  P  G  Q ccgccgaaactgctgatttactgggcaagcacccgcgaaagtggcgtgcctgatcgcttt
 P  P  K  L  L  I  Y  W  A  S  T  R  E  S  G  V  P  D  R  F agtggtagcggcagcggcaccgattttaccctgaccattagcagtctgcaggccgaggac
 S  G  S  G  S  G  T  D  F  T  L  T  I  S  S  L  Q  A  E  D gttgccgtttattactgccagcagtactatagcgcaccgctgacatttggcggtggcacc
 V  A  V  Y  Y  C  Q  Q  Y  Y  S  A  P  L  T  F  G  G  T aangtggaaattaaa
 X  V  E  I  K
```

F4-KZ52 HC N' Fusion Sequence:

Amino Acid (SEQ ID NO: 9):
EVQLLESGGGLVKPGGSLRLSCAASGFTLINYRMNWVRQAPGKGLEWVSS

ISSSSSYIHYADSVKGRFTISRDNAENSLYLQMNSLRAEDTAVYYCVREG

PRATGYSMADVFDIWGQGTMVTVSS<u>GGGGSGGGGSGGGGS</u>ELVMTQSPDS

LAVSLGERATINCKSSQSVLYSSNNKSYLAWYQQKPGQPPKLLIYWASTR

ESGVPDRFSGSGSGTDFTLTISSLQAEDVAVYYCQQYYSAPLTFGGGTKV

EIKGGSAGSAGSAGSGGSEVQLVESGGGLVQPGGSLRLSCAASGFAFNYY

DMFWVRQAPGKGLEWVAYIKPGGGNTYYADSVKGRFTISADTSKNTAYLQ

-continued

*MNSLRAEDTAVYYCARQLYGNSFFDYWGQGTLVTVSSASTKGPSVFPLAP*

*SSKSTSGGTAALGCLVKDYFPEPVTVSWNSGALTSGVHTFPAVLQSSGLY*

*SLSSVVTVPSSSLGTQTYICNVNHKPSNTKVDKKVEPKSCDKTHTCDKTH*

*TCPPCPAPELLGRPSVFLEPPKPKDTLMISRTPEVTCVVVDVSHEDPEVK*

*FNWYVDGVEVHNAKTKPREEQYNSTYRVVSVLTVLHQDWLNGKEYKCKVS*

-continued

*NKALPAPIEKTISKAKGQPREPQVYTLPPSREEMTKNQVSLTCLVKGFYP*

*SDIAVEWESNGQPENNYKTTPPVLDSDGSFELYSKLTVDKSRWQQGNVFS*

*CSVMHEALHNHYTQKSLSLSPGK*

Underlined region is glycine-rich linker polypeptide. Bold region is fusion linker polypeptide. Italicized region is CH1-CH3 for the HC and the CL region.

Nucleotide (SEQ ID NO: 10):
GAAGTTCAGTTACTGGAAAGTGGCGGCGGCCTGGTTAAACCGGGTGGTAGCCT

GCGTCTGAGTTGCGCAGCAAGCGGCTTCACCCTGATCAACTATCGCATGAACTG

GGTGCGCCAAGCACCGGGTAAGGGTCTGGAGTGGGTGAGCAGCATCAGCAGCA

GCAGCAGCTACATCCACTACGCAGACAGCGTTAAAGGCCGCTTCACCATTAGCC

GCGATAACGCCGAAAACAGCCTGTACCTGCAGATGAACAGTCTAAGGGCGGAG

GATACCGCAGTGTACTACTGCGTTCGTGAAGGCCCGCGTGCAACCGGCTATAGC

ATGGCCGACGTTTTTGATATTTGGGGCCAGGGCACCATGGTGACCGTGAGTAGT

GGTGGTGGTGGCAGCGGTGGTGGCGGTAGTGGTGGTGGTGGCAGTGAACTGGT

TATGACCCAGAGTCCGGACAGTCTGGCAGTGAGCCTGGGCGAGCGTGCAACCA

TCAACTGTAAGAGCAGTCAGAGCGTGCTGTATAGTAGCAACAATAAAAGCTAT

CTGGCCTGGTATCAGCAGAAGCCGGGTCAGCCGCCTAAGCTGCTGATTTATTGG

GCCAGCACCCGCGAAAGCGGTGTTCCGGATCGCTTTAGCGGTAGCGGCAGCGG

TACCGATTTCACCCTGACCATCAGCAGCCTGCAGGCCGAAGATGTGGCCGTGTA

TTATTGCCAGCAGTACTACAGCGCCCCGCTGACCTTTGGTGGCGGTACCAAGGT

GGAAATTAAAGGCGGCAGTGCCGGTAGTGCCGGTAGTGCAGGTAGCGGCGGTA

GCGAGGTTCAGCTGGTGGAAAGCGGCGGTGGTCTGGTTCAGCCTGGTGGTAGC

CTGCGCCTGAGCTGTGCCGCAAGCGGTTTCGCATTTAACTACTATGACATGTTCT

GGGTTCGCCAGGCACCGGGCAAAGGTCTGGAATGGGTGGCCTATATCAAACCG

GGCGGCGGCAACACCTACTACGCCGATAGCGTTAAGGGTCGTTTCACCATCAGC

GCCGATACCAGCAAAAACACCGCCTATCTGCAGATGAATAGCCTAAGGGCGGA

AGACACCGCAGTGTATTACTGCGCACGCCAGCTGTACGGCAACAGCTTTTTCGA

TTACTGGGGCCAGGGTACCCTGGTTACCGTGAGCAGC

Combined (SEQ ID NO: 9 and 10):
gaagttcagttactggaaagtggcggcggcctggttaaaccgggtggtagcctgcgtctg
 E  V  Q  L  L  E  S  G  G  G  L  V  K  P  G  G  S  L  R  L agttgcgcagcaagcggcttcaccctgatcaactatcgcatgaactgggtgcgccaagca
 S  C  A  A  S  G  F  T  L  I  N  Y  R  M  N  W  V  R  Q  A ccgggtaagggtctggagtgggtgagcagcatcagcagcagcagcagctacatccactac
 P  G  K  G  L  E  W  V  S  S  I  S  S  S  S  S  Y  I  H  Y gcagacagcgttaaaggccgcttcaccattagccgcgataacgccgaaaacagcctgtac
 A  D  S  V  K  G  R  F  T  I  S  R  D  N  A  E  N  S  L  Y ctgcagatgaacagtctaagggcggaggataccgcagtgtactactgcgttcgtgaaggc
 L  Q  M  N  S  L  R  A  E  D  T  A  V  Y  Y  C  V  R  E  G ccgcgtgcaaccggctatagcatggccgacgtttttgatatttggggccagggcaccatg
 P  R  A  T  G  Y  S  M  A  D  V  F  D  I  W  G  Q  G  T  M gtgaccgtgagtagtggtggtggtggcagcggtggtggcggtagtggtggtggtggcagt
 V  T  V  S  S  G  G  G  G  S  G  G  G  G  S  G  G  G  G  S

```
                            -continued
gaactggttatgacccagagtccggacagtctggcagtgagcctgggcgagcgtgcaacc
  E  L  V  M  T  Q  S  P  D  S  L  A  V  S  L  G  E  R  A  T atcaactgtaagagcagtcagagcgtgctgtatagtagcaacaataaaagctatctggcc
  I  N  C  K  S  S  Q  S  V  L  Y  S  S  N  N  K  S  Y  L  A tggtatcagcagaagccgggtcagccgcctaagctgctgatttattgggccagcacccgc
  W  Y  Q  Q  K  P  G  Q  P  P  K  L  L  I  Y  W  A  S  T  R gaaagcggtgttccggatcgctttagcggtagcggcagcggtaccgatttcaccctgacc
  E  S  G  V  P  D  R  F  S  G  S  G  S  G  T  D  F  T  L  T atcagcagcctgcaggccgaagatgtggccgtgtattattgccagcagtactacagcgcc
  I  S  S  L  Q  A  E  D  V  A  V  Y  Y  C  Q  Q  Y  Y  S  A ccgctgacctttggtggcggtaccaaggtggaaattaaaggcggcagtgccggtagtgcc
  P  L  T  F  G  G  G  T  K  V  E  I  K  G  G  S  A  G  S  A ggtagtgcaggtagcggcggtagcgaggttcagctggtggaaagcggcggtggtctggtt
  G  S  A  G  S  G  G  S  E  V  Q  L  V  E  S  G  G  G  L  V cagcctggtggtagcctgcgcctgagctgtgccgcaagcggtttcgcatttaactactat
  Q  P  G  G  S  L  R  L  S  C  A  A  S  G  F  A  F  N  Y  Y gacatgttctgggttcgccaggcaccgggcaaaggtctggaatgggtggcctatatcaaa
  D  M  F  W  V  R  Q  A  P  G  K  G  L  E  W  V  A  Y  I  K ccgggcggcggcaacacctactacgccgatagcgttaagggtcgtttcaccatcagcgcc
  P  G  G  G  N  T  Y  Y  A  D  S  V  K  G  R  F  T  I  S  A gataccagcaaaaacaccgcctatctgcagatgaatagcctaagggcggaagacaccgca
  D  T  S  K  N  T  A  Y  L  Q  M  N  S  L  R  A  E  D  T  A gtgtattactgcgcacgccagctgtacggcaacagcttttttcgattactggggccagggt
  V  Y  Y  C  A  R  Q  L  Y  G  N  S  F  F  D  Y  W  G  Q  G accctggttaccgtgagcagc
  T  L  V  T  V  S  S
```

F4-KZ52 LC N' Fusion Sequence:

Amino Acid (SEQ ID NO: 11):
EVQLLESGGGLVKPGGSLRLSCAASGFTLINYRMNWVRQAPGKGLEWVSS

ISSSSSYIHYADSVKGRFTISRDNAENSLYLQMNSLRAEDTAVYYCVREG

PRATGYSMADVFDIWGQGTMVTVSS<u>GGGGSGGGGSGGGGS</u>ELVMTQSPDS

LAVSLGERATINCKSSQSVLYSSNNKSYLAWYQQKPGQPPKLLIYWASTR

ESGVPDRFSGSGSGTDFTLTISSLQAEDVAVYYCQQYYSAPLTFGGGTKV

EIKGGSAGSAGSAGSGGSDIQMTQSPSSLSASVGDRVTITCKASQDVTTA

VAWYQQKPGKAPKLLIYWASTRHTGVPSRFSGSGSGTDFTLTISSLQPED

FATYYCQQHYSTPLTFGQGTKVEIK*RTVAAPSVFIFPPSDEQLKSGTASV*

*VCLLNNEYPREAKVQWKVDNALQSGNSQESVTEQDSKDSTYSLSSTLTLS*

*KADYEKHKVYACEVTHQGLSSPVTKSFNRGECGGSDYKDDDDK*

Underlined region is glycine-rich linker polypeptide. Bold region is fusion linker polypeptide. Italicized region is CH1-CH3 for the HC and the CL region.

Nucleotide (SEQ ID NO: 12):
GAAGTTCAGTTACTGGAAAGTGGCGGCGGCCTGGTTAAACCGGGTGGTAGCCT

GCGTCTGAGTTGCGCAGCAAGCGGCTTCACCCTGATCAACTATCGCATGAACTG

GGTGCGCCAAGCACCGGGTAAGGGTCTGGAGTGGGTGAGCAGCATCAGCAGCA

GCAGCAGCTACATCCACTACGCAGACAGCGTTAAAGGCCGCTTCACCATTAGCC

GCGATAACGCCGAAAACAGCCTGTACCTGCAGATGAACAGTCTAAGGGCGGAG

GATACCGCAGTGTACTACTGCGTTCGTGAAGGCCCGCGTGCAACCGGCTATAGC

ATGGCCGACGTTTTTGATATTTGGGGCCAGGGCACCATGGTGACCGTGAGTAGT

GGTGGTGGTGGCAGCGGTGGTGGCGGTAGTGGTGGTGGTGGCAGTGAACTGGT

TATGACCCAGAGTCCGGACAGTCTGGCAGTGAGCCTGGGCGAGCGTGCAACCA

TCAACTGTAAGAGCAGTCAGAGCGTGCTGTATAGTAGCAACAATAAAAGCTAT

CTGGCCTGGTATCAGCAGAAGCCGGGTCAGCCGCCTAAGCTGCTGATTTATTGG

-continued

```
GCCAGCACCCGCGAAAGCGGTGTTCCGGATCGCTTTAGCGGTAGCGGCAGCGG
TACCGATTTCACCCTGACCATCAGCAGCCTGCAGGCCGAAGATGTGGCCGTGTA
TTATTGCCAGCAGTACTACAGCGCCCCGCTGACCTTTGGTGGCGGTACCAAGGT
GGAAATTAAAGGCGGCAGTGCCGGTAGTGCCGGTAGTGCAGGTAGCGGCGGTA
GCGATATCCAGATGACCCAGAGTCCGAGTAGTCTGAGCGCCAGCGTTGGTGAC
CGCGTTACCATCACCTGCAAGGCCAGCCAGGATGTTACCACCGCCGTGGCCTGG
TATCAACAGAAACCGGGCAAGGCCCCGAAGCTGCTGATTTATTGGGCCAGTAC
ACGCCATACAGGCGTGCCGAGCCGTTTTAGTGGCAGCGGTAGCGGTACCGACTT
CACCCTGACCATCAGTAGCCTGCAACCGGAGGATTTCGCCACCTACTACTGCCA
GCAGCACTACAGCACCCCGCTGACCTTTGGCCAAGGTACCAAGGTGGAGATTA
AG
```

Combined (SEQ ID NO: 11 and 12):
```
gaagttcagttactggaaagtggcggcggcctggttaaaccgggtggtagcctgcgtctg
  E  V  Q  L  L  E  S  G  G  G  L  V  K  P  G  G  S  L  R  L agttgcgcagcaagcggcttcaccctgatcaactatcgcatgaactgggtgcgccaagca
  S  C  A  A  S  G  F  I  L  I  N  Y  R  M  N  W  V  R  Q  A ccgggtaagggtctggagtgggtgagcagcatcagcagcagcagcagctacatccactac
  P  G  K  G  L  E  W  V  S  S  I  S  S  S  S  S  Y  I  H  Y gcagacagcgttaaaggccgcttcaccattagccgcgataacgccgaaaacagcctgtac
  A  D  S  V  K  G  R  F  T  I  S  R  D  N  A  E  N  S  L  Y ctgcagatgaacagtctaagggcggaggataccgcagtgtactactgcgttcgtgaaggc
  L  Q  M  N  S  L  R  A  E  D  T  A  V  Y  Y  C  V  R  E  G ccgcgtgcaaccggctatagcatggccgacgttttgatatttggggccagggcaccatg
  P  R  A  T  G  Y  S  M  A  D  V  F  D  I  W  G  Q  G  T  M gtgaccgtgagtagtggtggtggtggcagcggtggtggcggtagtggtggtggtggcagt
  V  T  V  S  S  G  G  G  G  S  G  G  G  G  S  G  G  G  G  S gaactggttatgacccagagtccggacagtctggcagtgagcctgggcgagcgtgcaacc
  E  L  V  M  T  Q  S  P  D  S  L  A  V  S  L  G  E  R  A  T atcaactgtaagagcagtcagagcgtgctgtatagtagcaacaataaaagctatctggcc
  I  N  C  K  S  S  Q  S  V  L  Y  S  S  N  N  K  S  Y  L  A tggtatcagcagaagccgggtcagccgcctaagctgctgatttattgggccagcaccgc
  W  Y  Q  Q  K  P  G  Q  P  P  K  L  L  I  Y  W  A  S  T  R gaaagcggtgttccggatcgctttagcggtagcggcagcggtaccgatttcaccctgacc
  E  S  G  V  P  D  R  F  S  G  S  G  S  G  T  D  F  T  L  T atcagcagcctgcaggccgaagatgtggccgtgtattattgccagcagtactacagcgcc
  I  S  S  L  Q  A  E  D  V  A  V  Y  Y  C  Q  Q  Y  Y  S  A ccgctgacctttggtggcggtaccaaggtggaaattaaaggcggcagtgccggtagtgcc
  P  L  T  F  G  G  G  T  K  V  E  I  K  G  G  S  A  G  S  A ggtagtgcaggtagcggcggtagcgatatccagatgacccagagtccgagtagtctgagc
  G  S  A  G  S  G  G  S  D  I  Q  M  T  Q  S  P  S  S  L  S gccagcgttggtgaccgcgttaccatcacctgcaaggccagccaggatgttaccaccgcc
  A  S  V  G  D  R  V  T  I  T  C  K  A  S  Q  D  V  T  T  A gtggcctggtatcaacagaaaccgggcaaggccccgaagctgctgatttattgggccagt
  V  A  W  Y  Q  Q  K  P  G  K  A  P  K  L  L  I  Y  W  A  S acacgccatacaggcgtgccgagccgttttagtggcagcggtagcggtaccgacttcacc
  T  R  H  T  G  V  P  S  R  F  S  G  S  G  S  G  T  D  F  T ctgaccatcagtagcctgcaaccggaggatttcgccacctactactgccagcagcactac
  L  T  I  S  S  L  Q  P  E  D  F  A  T  Y  Y  C  Q  Q  H  Y agcacccccgctgacctttggccaaggtaccaaggtggagattaag
  S  T  P  L  T  F  G  Q  G  T  K  V  E  I  K
```

F4-KZ52 HC C' Fusion Sequence:

Amino Acid (SEQ ID NO: 13):
EVQLVESGGGLVQPGGSLRLSCAASGFAFNYYDMFWVRQAPGKGLEWVAY
IKPGGGNTYYADSVKGRFTISADTSKNTAYLQMNSLRAEDTAVYYCARQL
YGNSFFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCDKTHTCPPCPAPELLGRPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLS
LSPGKGGSAGSAGSAGSGGSEVQLLESGGGLVKPGGSLRLSCAASGFTLI
NYRMNWVRQAPGKGLEWVSSISSSSSYIHYADSVKGRFTISRDNAENSLY
LQMNSLRAEDTAVYYCVREGPRATGYSMADVFDIWGQGTMVTVSS<u>GGGGS
GGGGSGGGGS</u>ELVMTQSPDSLAVSLGERATINCKSSQSVLYSSNNKSYLA
WYQQKPGQPPKLLIYWASTRESGVPDRFSGSGSGTDFTLTISSLQAEDVA
VYYCQQYYSAPLTFGGGTKVEIK Underlined region is glycine-rich linker polypeptide. Bold region is fusion linker polypeptide.

Nucleotide (SEQ ID NO: 14):
GAAGTTCAACTGGTTGAGAGTGGCGGTGGCTTAGTTCAACCGGGCGGTAGTTTA
CGCCTGAGTTGTGCAGCCAGCGGTTTCGCCTTCAACTATTATGACATGTTTTGGG
TGCGCCAGGCACCGGGTAAAGGCCTGGAGTGGGTGGCCTATATCAAACCGGGC
GGTGGCAACACCTATTACGCCGATAGCGTGAAAGGTCGCTTTACCATCAGCGCA
GATACCAGCAAGAATACCGCCTACCTGCAGATGAATAGCCTGCGTGCCGAAGA
CACCGCCGTTTATTATTGCGCCCGCCAGCTGTACGGCAATAGCTTTTTCGATTAC
TGGGGCCAGGGCACCCTGGTTACCGTTAGCAGCGCTAGCACCAAGGGTCCGAG
CGTGTTTCCTCTGGCACCTAGCAGTAAAAGCACCAGTGGTGGTACAGCAGCCCT
GGGTTGCCTGGTGAAGGATTACTTTCCGGAGCCGGTGACCGTTAGTTGGAATAG
CGGCGCCCTGACCAGTGGCGTTCATACATTTCCGGCCGTGCTGCAGAGTAGTGG
CCTGTACAGCCTGAGTAGCGTTGTTACCGTTCCGAGCAGCAGCCTGGGCACCCA
GACCTATATTTGCAATGTTAACCATAAACCGAGCAACACAAAAGTTGATAAAA
AAGTTGAACCGAAGAGCTGTGACAAAACCCATACATGTGACAAAACACACACC
TGCCCGCCTTGTCCGGCACCTGAGCTGCTGGGTCGCCCGAGCGTTTTTCTGTTTC
CTCCGAAACCGAAAGACACCCTGATGATCAGCCGCACACCTGAGGTGACCTGT
GTTGTGGTGGATGTGAGCCACGAAGATCCTGAAGTTAAGTTTAACTGGTATGTG
GATGGCGTGGAGGTGCATAATGCCAAGACAAAGCCGCGTGAAGAGCAGTACAA
CAGCACCTATCGTGTTGTTAGTGTGCTGACCGTTCTGCACCAAGATTGGCTGAA
CGGCAAGGAGTATAAATGCAAGGTTAGCAATAAAGCCCTGCCGGCCCCGATCG
AGAAGACCATCAGCAAAGCCAAAGGTCAGCCGCGTGAGCCTCAGGTGTATACA
CTGCCGCCTAGCCGTGAGGAGATGACCAAGAATCAGGTTAGCCTGACCTGTCTG
GTGAAAGGCTTTTACCCGAGCGATATCGCCGTTGAGTGGGAAAGCAATGGTCA
GCCTGAGAACAACTACAAGACCACCCCGCCTGTTTTAGACAGTGATGGTAGCTT
TTTCTTATACAGCAAACTGACCGTTGATAAGAGCCGCTGGCAGCAGGGCAATGT
GTTTAGCTGCAGTGTTATGCATGAGGCCCTGCATAACCACTATACCCAGAAGAG
TCTGAGCCTGAGTCCTGGCAAAGGTGGATCCGCCGGTAGCGCAGGTAGTGCAG
GTAGTGGCGGCAGCGAAGTTCAGCTGTTAGAAAGTGGCGGTGGTCTGGTTAAG
CCGGGCGGTAGTCTGCGCCTGAGCTGTGCAGCAAGTGGTTTCACCCTGATCAAT
TATCGTATGAACTGGGTGCGCCAAGCCCCGGGTAAAGGTCTGGAGTGGGTTAGT
AGTATCAGCAGCAGCAGCAGTTACATCCACTATGCCGATAGCGTTAAGGGCCG -continued

```
CTTTACAATCAGCCGCGATAATGCCGAGAATAGCTTATACCTGCAAATGAACAG

TCTAAGGGCGGAAGATACCGCCGTTTACTACTGCGTTCGTGAAGGCCCTCGCGC

AACAGGCTATAGCATGGCAGACGTGTTCGACATTTGGGGTCAGGGCACCATGG

TGACCGTTAGTAGCGGCGGTGGTGGTAGTGGTGGTGGCGGTAGTGGTGGCGGT

GGCAGCGAACTGGTGATGACCCAGAGTCCGGATAGCCTGGCCGTGAGCTTAGG

CGAGCGTGCAACCATTAATTGTAAAAGCAGTCAGAGTGTTCTGTATAGTAGCAA

TAACAAGAGCTATCTGGCCTGGTATCAGCAGAAGCCGGGCCAGCCGCCGAAAC

TGCTGATTTACTGGGCAAGCACCCGCGAAAGTGGCGTGCCTGATCGCTTTAGTG

GTAGCGGCAGCGGCACCGATTTTACCCTGACCATTAGCAGTCTGCAGGCCGAGG

ACGTTGCCGTTTATTACTGCCAGCAGTACTATAGCGCACCGCTGACATTTGGCG

GTGGCACCAAGGTGGAAATTAAATAA
```

Combined (SEQ ID NO: 13 and 14):

```
gaagttcaactggttgagagtggcggtggcttagttcaaccgggcggtagtttacgcctg
 E  V  Q  L  V  E  S  G  G  G  L  V  Q  P  G  G  S  L  R  L agttgtgcagccagcggtttcgccttcaactattatgacatgttttgggtgcgccaggca
 S  C  A  A  S  G  F  A  F  N  Y  Y  D  M  F  W  V  R  Q  A ccgggtaaaggcctggagtgggtggcctatatcaaaccgggcggtggcaacacctattac
 P  G  K  G  L  E  W  V  A  Y  I  K  P  G  G  G  N  T  Y  Y gccgatagcgtgaaaggtcgctttaccatcagcgcagataccagcaagaataccgcctac
 A  D  S  V  K  G  R  F  T  I  S  A  D  T  S  K  N  T  A  Y ctgcagatgaatagcctgcgtgccgaagacaccgccgtttattattgcgcccgccagctg
 L  Q  M  N  S  L  R  A  E  D  T  A  V  Y  Y  C  A  R  Q  L tacggcaatagcttttttcgattactggggccagggcaccctggttaccgttagcagcgct
 Y  G  N  S  F  F  D  Y  W  G  Q  G  T  L  V  T  V  S  S  A agcaccaagggtccgagcgtgtttcctctggcacctagcagtaaaagcaccagtggtggt
 S  T  K  G  P  S  V  F  P  L  A  P  S  S  K  S  T  S  G  G acagcagccctgggttgcctggtgaaggattactttccggagccggtgaccgttagttgg
 T  A  A  L  G  C  L  V  K  D  Y  F  P  E  P  V  T  V  S  W aatagcggcgccctgaccagtggcgttcatacatttccggccgtgctgcagagtagtggc
 N  S  G  A  L  T  S  G  V  H  T  F  P  A  V  L  Q  S  S  G ctgtacagcctgagtagcgttgttaccgttccgagcagcagcctgggcacccagacctat
 L  Y  S  L  S  S  V  V  T  V  P  S  S  S  L  G  T  Q  T  Y atttgcaatgttaaccataaaccgagcaacacaaaagttgataaaaaagttgaaccgaag
 I  C  N  V  N  H  K  P  S  N  T  K  V  D  K  K  V  E  P  K agctgtgacaaaacccatacatgtgacaaaacacacacctgcccgccttgtccggcacct
 S  C  D  K  T  H  T  C  D  K  T  H  T  C  P  P  C  P  A  P gagctgctgggtcgcccgagcgttttttctgtttcctccgaaaccgaaagacacccctgatg
 E  L  L  G  R  P  S  V  F  L  F  P  P  K  P  K  D  T  L  M atcagccgcacacctgaggtgacctgtgttgtggtggatgtgagccacgaagatcctgaa
 I  S  R  I  P  E  V  T  C  V  V  V  D  V  S  H  E  D  P  E gttaagtttaactggtatgtggatggcgtggaggtgcataatgccaagacaaagccgcgt
 V  K  F  N  W  Y  V  D  G  V  E  V  H  N  A  K  T  K  P  R gaagagcagtacaacagcacctatcgtgttgttagtgtgctgaccgttctgcaccaagat
 E  E  Q  Y  N  S  T  Y  R  V  V  S  V  L  T  V  L  H  Q  D tggctgaacggcaaggagtataaatgcaaggttagcaataaagccctgccggcccccgatc
 W  L  N  G  K  E  Y  K  C  K  V  S  N  K  A  L  P  A  P  I gagaagaccatcagcaaagccaaaggtcagccgcgtgagcctcaggtgtatacactgccg
 E  K  T  I  S  K  A  K  G  Q  P  R  E  P  Q  V  Y  T  L  P cctagccgtgaggagatgaccaagaatcaggttagcctgacctgtctggtgaaaggcttt
 P  S  R  E  E  M  T  K  N  Q  V  S  L  T  C  L  V  K  G  F
```

```
                                    tacccgagcgatatcgccgttgagtgggaaagcaatggtcagcctgagaacaactacaag
                                     Y   P   S   D   I   A   V   E   W   E   S   N   G   Q   P   E   N   N   Y   K accaccccgcctgttttagacagtgatggtagcttttcttatacagcaaactgaccgtt
                                     T   T   P   P   V   L   D   S   D   G   S   F   F   L   Y   S   K   L   T   V gataagagccgctggcagcagggcaatgtgtttagctgcagtgttatgcatgaggccctg
                                     D   K   S   R   W   Q   Q   G   N   V   F   S   C   S   V   M   H   E   A   L cataaccactatacccagaagagtctgagcctgagtcctggcaaaggtggatccgccggt
                                     H   N   H   Y   T   Q   K   S   L   S   L   S   P   G   K   G   G   S   A   G agcgcaggtagtgcaggtagtggcggcagcgaagttcagctgttagaaagtggcggtggt
                                     S   A   G   S   A   G   S   G   G   S   E   V   Q   L   L   E   S   G   G   G ctggttaagccgggcggtagtctgcgcctgagctgtgcagcaagtggttttcaccctgatc
                                     L   V   K   P   G   G   S   L   R   L   S   C   A   A   S   G   F   T   L   I aattatcgtatgaactgggtgcgccaagcccccggtaaaggtctggagtgggttagtagt
                                     N   Y   R   M   N   W   V   R   Q   A   P   G   K   G   L   E   W   V   S   S atcagcagcagcagcagttacatccactatgccgatagcgttaagggccgctttacaatc
                                     I   S   S   S   S   S   Y   I   H   Y   A   D   S   V   K   G   R   F   T   I agccgcgataatgccgagaatagcttatacctgcaaatgaacagtctaagggcggaagat
                                     S   R   D   N   A   E   N   S   L   Y   L   Q   M   N   S   L   R   A   E   D accgccgtttactactgcgttcgtgaaggccctcgcgcaacaggctatagcatggcagac
                                     T   A   V   Y   Y   C   V   R   E   G   P   R   A   T   G   Y   S   M   A   D gtgttcgacatttggggtcagggcaccatggtgaccgttagtagcggcggtggtggtagt
                                     V   F   D   I   W   G   Q   G   T   M   V   T   V   S   S   G   G   G   G   S ggtggtggcggtagtggtggcggtggcagcgaactggtgatgacccagagtccggatagc
                                     G   G   G   G   S   G   G   G   G   S   E   L   V   M   T   Q   S   P   D   S ctggccgtgagcttaggcgagcgtgcaaccattaattgtaaaagcagtcagagtgttctg
                                     L   A   V   S   L   G   E   R   A   T   I   N   C   K   S   S   Q   S   V   L tatagtagcaataacaagagctatctggcctggtatcagcagaagccgggccagccgccg
                                     Y   S   S   N   N   K   S   Y   L   A   W   Y   Q   Q   K   P   G   Q   P   P aaactgctgatttactgggcaagcacccgcgaaagtggcgtgcctgatcgctttagtggt
                                     K   L   L   I   Y   W   A   S   T   R   E   S   G   V   P   D   R   F   S   G agcggcagcggcaccgattttacccctgaccattagcagtctgcaggccgaggacgttgcc
                                     S   G   S   G   T   D   F   T   L   T   I   S   S   L   Q   A   E   D   V   A gtttattactgccagcagtactatagcgcaccgctgacatttggcggtggcaccaaggtg
                                     V   Y   Y   C   Q   Q   Y   Y   S   A   P   L   T   F   G   G   G   T   K   V gaaattaaataa
                                     E   I   K   -
```

F4-KZ52 LC C' Fusion Sequence:

Amino Acid (SEQ ID NO: 15):
DIQMTQSPSSLSASVGDRVTITCKASQDVTTAVAWYQQKPGKAPKLLIYW

ASTRHTGVPSRFSGSGSGTDFTLTISSLQPEDFATYYCQQHYSTPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGSGGSAGSAGSAGSGGSEVQLLESGGGLVKPGGSL

RLSCAASGFTLINYRMNWVRQAPGKGLEWVSSISSSSSYIHYADSVKGRF

TISRDNAENSLYLQMNSLRAEDTAVYYCVREGPRATGYSMADVFDIWGQG

TMVTVSS<u>GGGGSGGGGSGGGGS</u>ELVMTQSPDSLAVSLGERATINCKSSQS

VLYSSNNKSYLAWYQQKPGQPPKLLIYWASTRESGVPDRFSGSGSGTDFT

LTISSLQAEDVAVYYCQQYYSAPLTFGGGTKVEIK

Underlined region is glycine-rich linker polypeptide. Bold region is fusion linker polypeptide.

Nucleotide (SEQ ID NO: 16):
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTA

TCAGCAGAAACCGGGTAAGGCCCCGAAGCTGCTGATCTATTGGGCCAGTACCC

GCCACACCGGTGTTCCTAGTCGCTTCAGTGGCAGTGGCAGCGGCACAGATTTCA

-continued

```
CCCTGACCATCAGCAGCCTGCAACCGGAAGATTTGCCACCTACTACTGCCAGC

AGCACTATAGCACCCCGCTGACCTTTGGCCAGGGCACCAAGGTTGAGATTAAAC

GTACGGTGGCAGCACCGAGCGTGTTTATCTTTCCGCCGAGCGACGAACAACTGA

AAAGTGGCACAGCCAGCGTGGTGTGTTTACTGAACAACTTCTATCCTCGCGAGG

CCAAGGTGCAGTGGAAAGTGGACAATGCACTGCAGAGTGGCAATAGCCAGGAG

AGCGTGACCGAACAGGATAGCAAAGATAGCACCTATAGCCTGAGTAGCACCCT

GACCCTGAGCAAGGCCGATTATGAGAAGCACAAGGTGTATGCATGCGAGGTTA

CCCATCAGGGCCTGAGCAGCCCGGTGACCAAAAGCTTTAACCGTGGCGAATGC

GGTGGTAGTGGTGGATCCGCCGGTAGCGCAGGTAGTGCAGGTAGTGGCGGCAG

CGAAGTTCAGCTGTTAGAAAGTGGCGGTGGTCTGGTTAAGCCGGGCGGTAGTCT

GCGCCTGAGCTGTGCAGCAAGTGGTTTCACCCTGATCAATTATCGTATGAACTG

GGTGCGCCAAGCCCCGGGTAAAGGTCTGGAGTGGGTTAGTAGTATCAGCAGCA

GCAGCAGTTACATCCACTATGCCGATAGCGTTAAGGGCCGCTTTACAATCAGCC

GCGATAATGCCGAGAATAGCTTATACCTGCAAATGAACAGTCTAAGGGCGGAA

GATACCGCCGTTTACTACTGCGTTCGTGAAGGCCCTCGCGCAACAGGCTATAGC

ATGGCAGACGTGTTCGACATTTGGGGTCAGGGCACCATGGTGACCGTTAGTAGC

GGCGGTGGTGGTAGTGGTGGTGGCGGTAGTGGTGGCGGTGGCAGCGAACTGGT

GATGACCCAGAGTCCGGATAGCCTGGCCGTGAGCTTAGGCGAGCGTGCAACCA

TTAATTGTAAAGCAGTCAGAGTGTTCTGTATAGTAGCAATAACAAGAGCTATC

TGGCCTGGTATCAGCAGAAGCCGGGCCAGCCGCCGAAACTGCTGATTTACTGG

GCAAGCACCCGCGAAAGTGGCGTGCCTGATCGCTTTAGTGGTAGCGGCAGCGG

CACCGATTTTACCCTGACCATTAGCAGTCTGCAGGCCGAGGACGTTGCCGTTTA

TTACTGCCAGCAGTACTATAGCGCACCGCTGACATTTGGCGGTGGCACCAAGGT

GGAAATTAAATAA
```

Combined (SEQ ID NO: 15 and 16):

```
gacattcagatgacccaaagtccgagcagcctgagtgccagtgttggtgatcgcgtgaca
 D   I   Q   M   T   Q   S   P   S   S   L   S   A   S   V   G   D   R   V   T atcacatgcaaggccagtcaggacgtgaccaccgcagtggcctggtatcagcagaaaccg
 I   T   C   K   A   S   Q   D   V   T   T   A   V   A   W   Y   Q   Q   K   P ggtaaggccccgaagctgctgatctattgggccagtacccgccacaccggtgttcctagt
 G   K   A   P   K   L   L   I   Y   W   A   S   I   R   H   T   G   V   P   S cgcttcagtggcagtggcagcggcacagatttcaccctgaccatcagcagcctgcaaccg
 R   F   S   G   S   G   S   G   T   D   F   T   L   T   I   S   S   L   Q   P gaagattttgccacctactactgccagcagcactatagcaccccgctgacctttggccag
 E   D   F   A   T   Y   Y   C   Q   Q   H   Y   S   T   P   L   T   F   G   Q ggcaccaaggttgagattaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S
```

-continued

```
gccggtagcgcaggtagtgcaggtagtggcggcagcgaagttcagctgttagaaagtggc
 A  G  S  A  G  S  A  G  S  G  G  S  E  V  Q  L  L  E  S  G ggtggtctggttaagccgggcggtagtctgcgcctgagctgtgcagcaagtggtttcacc
 G  G  L  V  K  P  G  G  S  L  R  L  S  C  A  A  S  G  F  T ctgatcaattatcgtatgaactgggtgcgccaagcccgggtaaaggtctggagtgggtt
 L  I  N  Y  R  M  N  W  V  R  Q  A  P  G  K  G  L  E  W  V agtagtatcagcagcagcagcagttacatccactatgccgatagcgttaagggccgcttt
 S  S  I  S  S  S  S  S  Y  I  H  Y  A  D  S  V  K  G  R  F acaatcagccgcgataatgccgagaatagcttatacctgcaaatgaacagtctaagggcg
 T  I  S  R  D  N  A  E  N  S  L  Y  L  Q  M  N  S  L  R  A gaagataccgccgtttactactgcgttcgtgaaggccctcgcgcaacaggctatagcatg
 E  D  T  A  V  Y  Y  C  V  R  E  G  P  R  A  T  G  Y  S  M gcagacgtgttcgacatttggggtcagggcaccatggtgaccgttagtagcggcggtggt
 A  D  V  F  D  I  W  G  Q  G  T  M  V  T  V  S  S  G  G  G ggtagtggtggtggcggtagtggtggcggtggcagcgaactggtgatgacccagagtccg
 G  S  G  G  G  S  G  G  G  S  E  L  V  M  T  Q  S  P gatagcctggccgtgagcttaggcgagcgtgcaaccattaattgtaaaagcagtcagagt
 D  S  L  A  V  S  L  G  E  R  A  T  I  N  C  K  S  S  Q  S gttctgtatagtagcaataacaagagctatctggcctggtatcagcagaagccgggccag
 V  L  Y  S  S  N  N  K  S  Y  L  A  W  Y  Q  Q  K  P  G  Q ccgccgaaactgctgatttactgggcaagcacccgcgaaagtggcgtgcctgatcgcttt
 P  P  K  L  L  I  Y  W  A  S  T  R  E  S  G  V  P  D  R  F agtggtagcggcagcggcaccgattttacccctgaccattagcagtctgcaggccgaggac
 S  G  S  G  S  G  T  D  F  T  L  T  I  S  S  L  Q  A  E  D gttgccgtttattactgccagcagtactatagcgcaccgctgacatttggcggtggcacc
 V  A  V  Y  Y  C  Q  Q  Y  Y  S  A  P  L  T  F  G  G  T aaggtggaaattaaataa
 K  V  E  I  K  -
```

F4-2G4 LC N' Fusion Sequence:

Amino acid (SEQ ID NO: 17):
EVQLQESGGGLMQPGGSMKLSCVASGFTFSNYWMNWVRQSPEKGLEWVAE

IRLKSNNYATHYAESVKGRFTISRDDSKRSVYLQMNTLRAEDTGIYYCTR

GNGNYRAMDYWGQGTSVTVSS<u>GGGGSGGGGSGGGGS</u>DIQMTQSPASLSVS

VGETVSITCRASENIYSSLAWYQQKQGKSPQLLVYSATILADGVPSRFSG

SGSGTQYSLKINSLQSEDFGTYYCQHFWGTPYTFGGGTKLEIKGGSAGSA

GSAGSGGSDIQMTQSPSSLSASVGDRVTITCKASQDVTTAVAWYQQKPGK

APKLLIYWASTRHTGVPSRFSGSGSGTDFTLTISSLQPEDFATYYCQQHY

STPLTFGQGTKVEIK

Underlined regions glycine-rich linker polypeptide. Bold region is fusion linker polypeptide.

Nucleotide (SEQ ID NO: 18):
GAAGTTCAGCTGCAGGAAAGCGGCGGTGGTCTGATGCAGCCTGGTGGCAGCATG

AAACTGAGCTGTGTGGCCAGCGGTTTTCACCTTCAGCAACTATTGGATGAACTGGGTGCGTC

AGAGTCCGGAAAAAGGCCTGGAATGGGTTGCCGAGATCCGCCTGAAGAGTAACAACTATGC

CACCCATTACGCCGAGAGCGTGAAAGGTCGCTTTACCATCAGCCGTGATGACAGCAAACGC

AGCGTGTATCTGCAGATGAACACATTACGTGCTGAAGACACCGGTATCTACTATTGCACCC

GCGGCAACGGCAACTATCGCGCCATGGATTATTGGGGCCAGGGTACCAGCGTGACCGTTAG

TAGCGGCGGCGGTGGTAGTGGTGGTGGTGGTAGTGGCGGTGGCGGTAGCGACATTCAAATG

ACCCAGAGTCCTGCAAGCCTGAGCGTGAGCGTGGGTGAGACCGTGAGCATCACATGCCGCG

CCAGCGAGAACATTTATAGCAGCCTGGCCTGGTACCAGCAAAAACAGGGTAAAAGCCCGCA

GCTGCTGGTGTATAGCGCCACCATTCTGGCAGATGGTGTGCCGAGCCGTTTTAGTGGCAGT

GGCAGTGGTACCCAGTACAGCCTGAAAATCAACAGCCTGCAGAGCGAAGACTTCGGCACCT

-continued

```
ACTACTGTCAGCACTTTTGGGGCACCCCGTATACCTTTGGCGGCGGTACCAAGCTGGAAAT

CAAAGGTGGATCCGCAGGTAGCGCAGGCAGTGCAGGCAGCGGTGGTAGCGATATCCAGATG

ACCCAAAGCCCGAGCAGCTTAAGTGCCAGCGTGGGCGATCGCGTGACCATCACCTGCAAAG

CCAGTCAGGACGTTACCACAGCCGTGGCCTGGTATCAGCAGAAACCGGGTAAAGCCCCTAA

GCTGCTGATCTATTGGGCCAGCACCCGCCACACAGGTGTTCCGAGTCGTTTCAGCGGCAGC

GGTAGCGGTACCGATTTTACCCTGACCATCAGCAGCCTGCAGCCGGAAGACTTCGCAACAT

ACTACTGCCAGCAGCACTATTCTACCCCGCTGACATTCGGCCAGGGCACAAAAGTGGAGAT

TAAA
```

Combined (SEQ ID NO: 17 and 18):

```
gaagttcagctgcaggaaagcggcggtggtctgatgcagcctggtggcagcatgaaactg
 E  V  Q  L  Q  E  S  G  G  G  L  M  Q  P  G  G  S  M  K  L agctgtgtggccagcggttttcaccttcagcaactattggatgaactgggtgcgtcagagt
 S  C  V  A  S  G  F  T  F  S  N  Y  W  M  N  W  V  R  Q  S ccggaaaaaggcctggaatgggttgccgagatccgcctgaagagtaacaactatgccacc
 P  E  K  G  L  E  W  V  A  E  I  R  L  K  S  N  N  Y  A  T cattacgccgagagcgtgaaaggtcgctttaccatcagccgtgatgacagcaaacgcagc
 H  Y  A  E  S  V  K  G  R  F  T  I  S  R  D  D  S  K  R  S gtgtatctgcagatgaacacattacgtgctgaagacaccggtatctactattgcacccgc
 V  Y  L  Q  M  N  T  L  R  A  E  D  T  G  I  Y  Y  C  T  R ggcaacggcaactatcgcgccatggattattggggccagggtaccagcgtgaccgttagt
 G  N  G  N  Y  R  A  M  D  Y  W  G  Q  G  T  S  V  T  V  S agcggcggcggtggtagtggtggtggtggtagtggcggtggcggtagcgacattcaaatg
 S  G  G  G  G  S  G  G  G  G  S  G  G  G  G  S  D  I  Q  M acccagagtcctgcaagcctgagcgtgagcgtgggtgagaccgtgagcatcacatgccgc
 T  Q  S  P  A  S  L  S  V  S  V  G  E  T  V  S  I  T  C  R gccagcgagaacatttatagcagcctggcctggtaccagcaaaaacagggtaaaagcccg
 A  S  E  N  I  Y  S  S  L  A  W  Y  Q  Q  K  Q  G  K  S  P cagctgctggtgtatagcgccaccattctggcagatggtgtgccgagccgttttagtggc
 Q  L  L  V  Y  S  A  T  I  L  A  D  G  V  P  S  R  F  S  G agtggcagtggtacccagtacagcctgaaaatcaacagcctgcagagcgaagacttcggc
 S  G  S  G  T  Q  Y  S  L  K  I  N  S  L  Q  S  E  D  F  G acctactactgtcagcacttttggggcacccgtataccttt ggcggcggtaccaagctg
 T  Y  Y  C  Q  H  F  W  G  T  P  Y  T  F  G  G  G  T  K  L gaaatcaaaggtggatccgcaggtagcgcaggcagtgcaggcagcggtggtagcgatatc
 E  I  K  G  G  S  A  G  S  A  G  S  A  G  S  G  G  S  D  I cagatgacccaaagcccgagcagcttaagtgccagcgtgggcgatcgcgtgaccatcacc
 Q  M  T  Q  S  P  S  S  L  S  A  S  V  G  D  R  V  T  I  T tgcaaagccagtcaggacgttaccacagccgtggcctggtatcagcagaaaccgggtaaa
 C  K  A  S  Q  D  V  T  T  A  V  A  W  Y  Q  Q  K  P  G  K gcccctaagctgctgatctattgggccagcacccgccacacaggtgttccgagtcgtttc
 A  P  K  L  L  I  Y  W  A  S  T  R  H  T  G  V  P  S  R  F agcggcagcggtagcggtaccgattttaccctgaccatcagcagcctgcagccggaagac
 S  G  S  G  S  G  T  D  F  T  L  T  I  S  S  L  Q  P  E  D ttcgcaacatactactgccagcagcactattctacccc gctgacattcggccagggcaca
 F  A  T  Y  Y  C  Q  Q  H  Y  S  T  P  L  T  F  G  Q  G  T aaagtggagattaaa
 K  V  E  I  K
```

E10-2G4 LC N' Fusion Sequence - Amino Acid (SEQ ID NO: 19):
EVQLQESGGGLMQPGGSMKLSCVASGFTFSNYWMNWVRQSPEKGLEWVAEIRLK

SNNYATHYAESVKGRFTISRDDSKRSVYLQMNTLRAEDTGIYYCTRGNGNYRAMDYWGQGT

SVTVSS<u>GGGGSGGGGSGGGGS</u>DIQMTQSPASLSVSVGETVSITCRASENIYSSLAWYQQKQ

-continued

GKSPQLLVYSATILADGVPSRFSGSGSGTQYSLKINSLQSEDFGTYYCQHFWGTPYTFGGG

TKLEIKGGSAGSAGSAGSGGSDIQMTQSPSSLSASVGDRVTITCRASQDVTTAVAWYQQKP

GKAPKLLIYWASRLHNGVPSRFSGSGSGTDFTLTISSLQPEDFATYYCQQHYSTPLTFGQG

TKVEIK

Underlined region is glycine-rich linker polypeptide. Bold region is fusion linker polypeptide.

```
Nucleotide (SEQ ID NO: 20):
GAAGTTCAGCTGCAGGAAAGCGGCGGTGGTCTGATGCAGCCTGGTGGCAGCATG

AAACTGAGCTGTGTGGCCAGCGGTTTCACCTTCAGCAACTATTGGATGAACTGGGTGCGTC

AGAGTCCGGAAAAAGGCCTGGAATGGGTTGCCGAGATCCGCCTGAAGAGTAACAACTATGC

CACCCATTACGCCGAGAGCGTGAAAGGTCGCTTTACCATCAGCCGTGATGACAGCAAACGC

AGCGTGTATCTGCAGATGAACACATTACGTGCTGAAGACACCGGTATCTACTATTGCACCC

GCGGCAACGGCAACTATCGCGCCATGGATTATTGGGGCCAGGGTACCAGCGTGACCGTTAG

TAGCGGCGGCGGTGGTAGTGGTGGTGGTGGTAGTGGCGGTGGCGGTAGCGACATTCAAATG

ACCCAGAGTCCTGCAAGCCTGAGCGTGAGCGTGGGTGAGACCGTGAGCATCACATGCCGCG

CCAGCGAGAACATTTATAGCAGCCTGGCCTGGTACCAGCAAAAACAGGGTAAAAGCCCGCA

GCTGCTGGTGTATAGCGCCACCATTCTGGCAGATGGTGTGCCGAGCCGTTTTAGTGGCAGT

GGCAGTGGTACCCAGTACAGCCTGAAAATCAACAGCCTGCAGAGCGAAGACTTCGGCACCT

ACTACTGTCAGCACTTTTGGGGCACCCCGTATACCTTTGGCGGCGGTACCAAGCTGGAAAT

CAAAGGTGGATCCGCCGGTAGCGCAGGTAGTGCCGGTAGCGGTGGCAGCGATATCCAAATG

ACCCAGAGCCCGAGTAGCCTGAGTGCAAGTGTGGGCGATCGCGTTACCATCACCTGTCGCG

CAAGCCAGGACGTGACAACCGCCGTGGCCTGGTATCAGCAGAAACCTGGTAAAGCCCCGAA

GCTGCTGATTTACTGGGCCAGCCGCCTGCACAATGGTGTTCCGAGTCGCTTTAGCGGCAGT

GGCAGCGGCACAGACTTTACACTGACCATTAGCAGCCTGCAGCCGGAGGATTTTGCCACCT

ATTATTGCCAGCAGCATTACAGTACACCGCTGACCTTCGGCCAGGGTACCAAAGTGGAAAT

CAAA
```

Combined (SEQ ID NO: 19 and 20):

```
gaagttcagctgcaggaaagcggcggtggtctgatgcagcctggtggcagcatgaaactg
 E   V   Q   L   Q   E   S   G   G   G   L   M   Q   P   G   G   S   M   K   L agctgtgtggccagcggtttcaccttcagcaactattggatgaactgggtgcgtcagagt
 S   C   V   A   S   G   F   T   F   S   N   Y   W   M   N   W   V   R   Q   S ccggaaaaaggcctggaatgggttgccgagatccgcctgaagagtaacaactatgccacc
 P   E   K   G   L   E   W   V   A   E   I   R   L   K   S   N   N   Y   A   T cattacgccgagagcgtgaaaggtcgctttaccatcagccgtgatgacagcaaacgcagc
 H   Y   A   E   S   V   K   G   R   F   T   I   S   R   D   D   S   K   R   S gtgtatctgcagatgaacacattacgtgctgaagacaccggtatctactattgcacccgc
 V   Y   L   Q   M   N   T   L   R   A   E   D   T   G   I   Y   Y   C   T   R ggcaacggcaactatcgcgccatggattattggggccagggtaccagcgtgaccgttagt
 G   N   G   N   Y   R   A   M   D   Y   W   G   Q   G   T   S   V   T   V   S agcggcggcggtggtagtggtggtggtggtagtggcggtggcggtagcgacattcaaatg
 S   G   G   G   G   S   G   G   G   G   S   G   G   G   S   D   I   Q   M acccagagtcctgcaagcctgagcgtgagcgtgggtgagaccgtgagcatcacatgccgc
 T   Q   S   P   A   S   L   S   V   S   V   G   E   T   V   S   I   T   C   R gccagcgagaacatttatagcagcctggcctggtaccagcaaaaacagggtaaaagcccg
 A   S   E   N   I   Y   S   S   L   A   W   Y   Q   Q   K   Q   G   K   S   P
```

-continued

```
cagctgctggtgtatagcgccaccattctggcagatggtgtgccgagccgttttagtggc
Q   L   L   V   Y   S   A   T   I   L   A   D   G   V   P   S   R   F   S   G agtggcagtggtacccagtacagcctgaaaatcaacagcctgcagagcgaagacttcggc
S   G   S   G   T   Q   Y   S   L   K   I   N   S   L   Q   S   E   D   F   G acctactactgtcagcactttggggcacccgtatacctttggcggcggtaccaagctg
T   Y   Y   C   Q   H   F   W   G   T   P   Y   T   F   G   G   G   T   K   L gaaatcaaaggtggatccgccggtagcgcaggtagtgccggtagcggtggcagcgatatc
E   I   K   G   S   A   A   G   S   A   G   S   A   G   S   G   G   S   D   I caaatgacccagagcccgagtagcctgagtgcaagtgtgggcgatcgcgttaccatcacc
Q   M   T   Q   S   P   S   S   L   S   A   S   V   G   D   R   V   T   I   T tgtcgcgcaagccaggacgtgacaaccgccgtggcctggtatcagcagaaacctggtaaa
C   R   A   S   Q   D   V   T   T   A   V   A   W   Y   Q   Q   K   P   G   K gccccgaagctgctgatttactgggccagccgcctgcacaatggtgttccgagtcgcttt
A   P   K   L   L   I   Y   W   A   S   R   H   N   G   V   P   S   R   F agcggcagtggcagcggcacagactttacactgaccattagcagcctgcagccggaggat
S   G   S   G   S   G   T   D   F   T   L   T   I   S   S   L   Q   P   E   D tttgccacctattattgccagcagcattacagtacaccgctgaccttcggccagggtacc
F   A   T   Y   Y   C   Q   Q   H   Y   S   T   P   L   T   F   G   Q   G   T aaagtggaaatcaaa
K   V   E   I   K F4-4G7 LC N' Fusion Sequence - Amino Acid (SEQ ID NO: 21):
EVQLQESGPELEMPGASVKISCKASGSSFTGFSMNWVKQSNGKSLEWIGNIDTY

YGGTTYNQKFKGKATLTVDKSSSTAYMQLKSLTSEDSAVYYCARSAYYGSTFAYWGQGTLV

TVSAGGGGSGGGGSGGGGSDIQMTQSPASLSASVGETVTITCRASENIYSYLAWYQQKQGK

SPQLLVYNAKTLIEGVPSRFSGSGSGTQFSLKINSLQPEDFGSYFCQHHFGTPFTFGSGTE

LEIKGGSAGSAGSAGSGGSDIQMTQSPSSLSASVGDRVTITCRASQDVTTAVAWYQQKPGK

APKLLIYWASRLHNGVPSRFSGSGSGTDFTLTISSLQPEDFATYYCQQHYSTPLTFGQGTK

VEIK
```

Underlined region glycine-rich linker polypeptide. Bold region is fusion linker polypeptide.

```
Nucleotide (SEQ ID NO: 22):
GAGGTGCAGCTGCAAGAAAGTGGTCCGGAACTGGAAATGCCGGGTGCCAGCGTG

AAAATCAGCTGCAAAGCCAGCGGCAGTAGCTTTACCGGCTTTAGCATGAACTGGGTGAAAC

AGAGCAACGGCAAGAGCCTGGAGTGGATCGGCAATATTGACACCTACTACGGCGGCACCAC

CTATAACCAGAAGTTCAAAGGCAAAGCCACACTGACCGTGGACAAGAGTAGCAGTACAGCC

TACATGCAGCTGAAAAGCCTGACCAGCGAGGATAGCGCAGTGTATTACTGCGCACGCAGCG

CCTATTACGGCAGCACATTTGCCTACTGGGGTCAGGGTACCCTGGTGACAGTTAGCGCAGG

CGGTGGTGGCAGTGGTGGTGGTGGTAGCGGTGGTGGTGGCAGCGACATTCAAATGACACAG

AGCCCGGCCAGTCTGAGTGCAAGCGTTGGCGAAACCGTGACCATTACCTGCCGTGCCAGCG

AGAACATCTATAGCTACCTGGCCTGGTACCAGCAGAAGCAGGGTAAAAGCCCTCAGCTGCT

GGTGTACAATGCCAAAACCCTGATCGAAGGCGTTCCGAGTCGCTTTAGTGGCAGCGGCAGT

GGCACCCAGTTCAGCCTGAAAATCAACAGCCTGCAACCGGAAGACTTTGGCAGCTACTTCT

GCCAGCACCATTTTGGCACACCGTTCACCTTCGGTAGTGGCACCGAACTGGAGATTAAAGG

TGGATCCGCAGGTAGCGCAGGCAGTGCAGGCAGCGGTGGTAGCGATATCCAGATGACCCAA

AGCCCGAGCAGCTTAAGTGCCAGCGTGGGCGATCGCGTGACCATCACCTGCAAAGCCAGTC
```

```
-continued
AGGACGTTACCACAGCCGTGGCCTGGTATCAGCAGAAACCGGGTAAAGCCCCTAAGCTGCT

GATCTATTGGGCCAGCACCCGCCACACAGGTGTTCCGAGTCGTTTCAGCGGCAGCGGTAGC

GGTACCGATTTTACCCTGACCATCAGCAGCCTGCAGCCGGAAGACTTCGCAACATACTACT

GCCAGCAGCACTATTCTACCCCGCTGACATTCGGCCAGGGCACAAAAGTGGAGATTAAA
```

Combined (SEQ ID NO: 21 and 22):
```
gaggtgcagctgcaagaaagtggtccggaactggaaatgccgggtgccagcgtgaaaatc
 E   V   Q   L   Q   E   S   G   P   E   L   E   M   P   G   A   S   V   K   I agctgcaaagccagcggcagtagctttaccggctttagcatgaactgggtgaaacagagc
 S   C   K   A   S   G   S   S   F   T   G   F   S   M   N   W   V   K   Q   S aacggcaagagcctggagtggatcggcaatattgacacctactacggcggcaccacctat
 N   G   K   S   L   E   W   I   G   N   I   D   T   Y   Y   G   G   T   T   Y aaccagaagttcaaaggcaaagccacactgaccgtggacaagagtagcagtacagcctac
 N   Q   K   F   K   G   K   A   T   L   T   V   D   K   S   S   S   T   A   Y atgcagctgaaaagcctgaccagcgaggatagcgcagtgtattactgcgcacgcagcgcc
 M   Q   L   K   S   L   T   S   E   D   S   A   V   Y   Y   C   A   R   S   A tattacggcagcacatttgcctactggggtcagggtaccctggtgacagttagcgcaggc
 Y   Y   G   S   T   F   A   Y   W   G   Q   G   T   L   V   T   V   S   A   G ggtggtggcagtggtggtggtggtagcggtggtggtggcagcgacattcaaatgacacag
 G   G   G   S   G   G   G   G   S   G   G   G   G   S   D   I   Q   M   T   Q agcccggccagtctgagtgcaagcgttggcgaaaccgtgaccattacctgccgtgccagc
 S   P   A   S   L   S   A   S   V   G   E   T   V   T   I   T   C   R   A   S gagaacatctatagctacctggcctggtaccagcagaagcagggtaaaagccctcagctg
 E   N   I   Y   S   Y   L   A   W   Y   Q   Q   K   Q   G   K   S   P   Q   L ctggtgtacaatgccaaaaccctgatcgaaggcgttccgagtcgctttagtggcagcggc
 L   V   Y   N   A   K   T   L   I   E   G   V   P   S   R   F   S   G   S   G agtggcacccagttcagcctgaaaatcaacagcctgcaaccggaagactttggcagctac
 S   G   T   Q   F   S   L   K   I   N   S   L   Q   P   E   D   F   G   S   Y ttctgccagcaccattttggcacaccgttcaccttcggtagtggcaccgaactggagatt
 F   C   Q   H   H   F   G   T   P   F   T   F   G   S   G   T   E   L   E   I aaaggtggatccgcaggtagcgcaggcagtgcaggcagcggtggtagcgatatccagatg
 K   G   G   S   A   G   S   A   G   S   A   G   S   G   G   S   D   I   Q   M acccaaagcccgagcagcttaagtgccagcgtgggcgatcgcgtgaccatcacctgcaaa
 T   Q   S   P   S   S   L   S   A   S   V   G   D   R   V   T   I   T   C   K gccagtcaggacgttaccacagccgtggcctggtatcagcagaaaccgggtaaagcccct
 A   S   Q   D   V   T   T   A   V   A   W   Y   Q   Q   K   P   G   K   A   P aagctgctgatctattgggccagcacccgccacacaggtgttccgagtcgtttcagcggc
 K   L   L   I   Y   W   A   S   T   R   H   T   G   V   P   S   R   F   S   G agcggtagcggtaccgattttacccttgaccatcagcagcctgcagccggaagacttcgca
 S   G   S   G   T   D   F   T   L   T   I   S   S   L   Q   P   E   D   F   A acatactactgccagcagcactattctaccccgctgacattcggccagggcacaaaagtg
 T   Y   Y   C   Q   Q   H   Y   S   T   P   L   T   F   G   Q   G   T   K   V gagattaaa
 E   I   K
```

E10-4G7 LC N' Fusion Sequence - Amino Acid (SEQ ID NO: 23):
EVQLQESGPELEMPGASVKISCKASGSSFTGFSMNWVKQSNGKSLEWIGNIDTY

YGGTTYNQKFKGKATLTVDKSSSTAYMQLKSLTSEDSAVYYCARSAYYGSTFAYWGQGTLV

TVSA<u>GGGGSGGGGSGGGGS</u>DIQMTQSPASLSASVGETVTITCRASENIYSYLAWYQQKQGK

SPQLLVYNAKTLIEGVPSRFSGSGSGTQFSLKINSLQPEDFGSYFCQHHFGTPFTFGSGTE

LEIKGGSAGSAGSAGSGGSDIQMTQSPSSLSASVGDRVTITCRASQDVTTAVAWYQQKPGK

APKLLIYWASRLHNGVPSRFSGSGSGTDFTLTISSLQPEDFATYYCQQHYSTPLTFGQGTK

VEIK

Underlined region is glycine-rich linker polypeptide. Bold is fusion linker polypeptide.

```
Nucleotide (SEQ ID NO: 24):
GAGGTGCAGCTGCAAGAAAGTGGTCCGGAACTGGAAATGCCGGGTGCCAGCGTG

AAAATCAGCTGCAAAGCCAGCGGCAGTAGCTTTACCGGCTTTAGCATGAACTGGGTGAAAC

AGAGCAACGGCAAGAGCCTGGAGTGGATCGGCAATATTGACACCTACTACGGCGGCACCAC

CTATAACCAGAAGTTCAAAGGCAAAGCCACACTGACCGTGGACAAGAGTAGCAGTACAGCC

TACATGCAGCTGAAAAGCCTGACCAGCGAGGATAGCGCAGTGTATTACTGCGCACGCAGCG

CCTATTACGGCAGCACATTTGCCTACTGGGGTCAGGGTACCCTGGTGACAGTTAGCGCAGG

CGGTGGTGGCAGTGGTGGTGGTGGTAGCGGTGGTGGTGGCAGCGACATTCAAATGACACAG

AGCCCGGCCAGTCTGAGTGCAAGCGTTGGCGAAACCGTGACCATTACCTGCCGTGCCAGCG

AGAACATCTATAGCTACCTGGCCTGGTACCAGCAGAAGCAGGGTAAAAGCCCTCAGCTGCT

GGTGTACAATGCCAAAACCCTGATCGAAGGCGTTCCGAGTCGCTTTAGTGGCAGCGGCAGT

GGCACCCAGTTCAGCCTGAAAATCAACAGCCTGCAACCGGAAGACTTTGGCAGCTACTTCT

GCCAGCACCATTTTGGCACACCGTTCACCTTCGGTAGTGGCACCGAACTGGAGATTAAGG

TGGATCCGCCGGTAGCGCAGGTAGTGCCGGTAGCGGTGGCAGCGATATCCAAATGACCCAG

AGCCCGAGTAGCCTGAGTGCAAGTGTGGGCGATCGCGTTACCATCACCTGTCGCGCAAGCC

AGGACGTGACAACCGCCGTGGCCTGGTATCAGCAGAAACCTGGTAAAGCCCCGAAGCTGCT

GATTTACTGGGCCAGCCGCCTGCACAATGGTGTTCCGAGTCGCTTTAGCGGCAGTGGCAGC

GGCACAGACTTTACACTGACCATTAGCAGCCTGCAGCCGGAGGATTTTGCCACCTATTATT

GCCAGCAGCATTACAGTACACCGCTGACCTTCGGCCAGGGTACCAAAGTGGAAATCAAA

Combined (SEQ ID NO: 23 and 24):
gaggtgcagctgcaagaaagtggtccggaactggaaatgccgggtgccagcgtgaaaatc
 E   V   Q   L   Q   E   S   G   P   E   L   E   M   P   G   A   S   V   K   I agctgcaaagccagcggcagtagctttaccggctttagcatgaactgggtgaaacagagc
 S   C   K   A   S   G   S   S   F   T   G   F   S   M   N   W   V   K   Q   S aacggcaagagcctggagtggatcggcaatattgacacctactacggcggcaccacctat
 N   G   K   S   L   E   W   I   G   N   I   D   T   Y   Y   G   G   T   T   Y aaccagaagttcaaaggcaaagccacactgaccgtggacaagagtagcagtacagcctac
 N   Q   K   F   K   G   K   A   T   L   T   V   D   K   S   S   S   T   A   Y atgcagctgaaaagcctgaccagcgaggatagcgcagtgtattactgcgcacgcagcgcc
 M   Q   L   K   S   L   T   S   E   D   S   A   V   Y   Y   C   A   R   S   A tattacggcagcacatttgcctactggggtcagggtaccctggtgacagttagcgcaggc
 Y   Y   G   S   T   F   A   Y   W   G   Q   G   T   L   V   T   V   S   A   G ggtggtggcagtggtggtggtggtagcggtggtggtggcagcgacattcaaatgacacag
 G   G   G   S   G   G   G   G   S   G   G   G   G   S   D   I   Q   M   T   Q agcccggccagtctgagtgcaagcgttggcgaaaccgtgaccattacctgccgtgccagc
 S   P   A   S   L   S   A   S   V   G   E   T   V   T   I   T   C   R   A   S gagaacatctatagctacctggcctggtaccagcagaagcagggtaaaagccctcagctg
 E   N   I   Y   S   Y   L   A   W   Y   Q   Q   K   Q   G   K   S   P   Q   L ctggtgtacaatgccaaaaccctgatcgaaggcgttccgagtcgctttagtggcagcggc
 L   V   Y   N   A   K   T   L   I   E   G   V   P   S   R   F   S   G   S   G agtggcacccagttcagcctgaaaatcaacagcctgcaaccggaagactttggcagctac
 S   G   T   Q   F   S   L   K   I   N   S   L   Q   P   E   D   F   G   S   Y ttctgccagcaccattttggcacaccgttcaccttcggtagtggcaccgaactggagatt
 F   C   Q   H   H   F   G   T   P   F   T   F   G   S   G   T   E   L   E   I aaaggtggatccgccggtagcgcaggtagtgccggtagcggtggcagcgatatccaaatg
 K   G   G   S   A   G   S   A   G   S   A   G   S   G   G   S   D   I   Q   M
```

```
acccagagcccgagtagcctgagtgcaagtgtgggcgatcgcgttaccatcacctgtcgc
 T  Q  S  P  S  S  L  S  A  S  V  G  D  R  V  T  I  T  C  R gcaagccaggacgtgacaaccgccgtggcctggtatcagcagaaacctggtaaagccccg
 A  S  Q  D  V  T  T  A  V  A  W  Y  Q  Q  K  P  G  K  A  P aagctgctgatttactgggccagccgcctgcacaatggtgttccgagtcgctttagcggc
 K  L  L  I  Y  W  A  S  R  L  H  N  G  V  P  S  R  F  S  G agtggcagcggcacagactttacactgaccattagcagcctgcagccggaggattttgcc
 S  G  S  G  T  D  F  T  L  T  I  S  S  L  Q  P  E  D  F  A acctattattgccagcagcattacagtacaccgctgaccttcggccagggtaccaaagtg
 T  Y  Y  C  Q  Q  H  Y  S  T  P  L  T  F  G  Q  G  T  K  V gaaatcaaa
 E  I  K F4-2G4 HC C' Fusion Sequence - Amino Acid (SEQ ID NO: 25):
EVQLVESGGGLVQPGGSLRLSCAASGFAFNYYDMFWVRQAPGKGLEWVAYIKPG

GGNTYYADSVKGRFTISADTSKNTAYLQMNSLRAEDTAVYYCARQLYGNSFFDYWGQGTLV

TVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCDKTHTCPPC

PAPELLGRPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGKGGSAGSAGSAGSGGSEVQLQESGGGL

MQPGGSMKLSCVASGFTFSNYWMNWVRQSPEKGLEWVAEIRLKSNNYATHYAESVKGRFTI

SRDDSKRSVYLQMNTLRAEDTGIYYCTRGNGNYRAMDYWGQGTSVTVSS<u>GGGGSGGGGSGG</u>

<u>GGS</u>DIQMTQSPASLSVSVGETVSITCRASENIYSSLAWYQQKQGKSPQLLVYSATILADGV

PSRFSGSGSGTQYSLKINSLQSEDFGTYYCQHFWGTPYTFGGGTKLEIK
```

Underlined region glycine-rich linker peptide. Bold region is fusion linker polypeptide.

```
Nucleotide (SEQ ID NO: 26):
GAAGTTCAACTGGTTGAGAGTGGCGGTGGCTTAGTTCAACCGGGCGGTAGTTTA

CGCCTGAGTTGTGCAGCCAGCGGTTTCGCCTTCAACTATTATGACATGTTTTGGGTGCGCC

AGGCACCGGGTAAAGGCCTGGAGTGGGTGGCCTATATCAAACCGGGCGGTGGCAACACCTA

TTACGCCGATAGCGTGAAAGGTCGCTTTACCATCAGCGCAGATACCAGCAAGAATACCGCC

TACCTGCAGATGAATAGCCTGCGTGCCGAAGACACCGCCGTTTATTATTGCGCCCGCCAGC

TGTACGGCAATAGCTTTTTCGATTACTGGGGCCAGGGCACCCTGGTTACCGTTAGCAGCGC

TAGCACCAAGGGTCCGAGCGTGTTTCCTCTGGCACCTAGCAGTAAAAGCACCAGTGGTGGT

ACAGCAGCCCTGGGTTGCCTGGTGAAGGATTACTTTCCGGAGCCGGTGACCGTTAGTTGGA

ATAGCGGCGCCCTGACCAGTGGCGTTCATACATTTCCGGCCGTGCTGCAGAGTAGTGGCCT

GTACAGCCTGAGTAGCGTTGTTACCGTTCCGAGCAGCAGCCTGGGCACCCAGACCTATATT

TGCAATGTTAACCATAAACCGAGCAACACAAAAGTTGATAAAAAAGTTGAACCGAAGAGCT

GTGACAAACCCATACATGTGACAAAACACACACCTGCCCGCCTTGTCCGGCACCTGAGCT

GCTGGGTCGCCCGAGCGTTTTTCTGTTTCCTCCGAAACCGAAAGACACCCTGATGATCAGC

CGCACACCTGAGGTGACCTGTGTTGTGGTGGATGTGAGCCACGAAGATCCTGAAGTTAAGT

TTAACTGGTATGTGGATGGCGTGGAGGTGCATAATGCCAAGACAAAGCCGCGTGAAGAGCA
```

-continued
```
GTACAACAGCACCTATCGTGTTGTTAGTGTGCTGACCGTTCTGCACCAAGATTGGCTGAAC

GGCAAGGAGTATAAATGCAAGGTTAGCAATAAAGCCCTGCCGGCCCCGATCGAGAAGACCA

TCAGCAAAGCCAAAGGTCAGCCGCGTGAGCCTCAGGTGTATACACTGCCGCCTAGCCGTGA

GGAGATGACCAAGAATCAGGTTAGCCTGACCTGTCTGGTGAAAGGCTTTTACCCGAGCGAT

ATCGCCGTTGAGTGGGAAAGCAATGGTCAGCCTGAGAACAACTACAAGACCACCCCGCCTG

TTTTAGACAGTGATGGTAGCTTTTTCTTATACAGCAAACTGACCGTTGATAAGAGCCGCTG

GCAGCAGGGCAATGTGTTTAGCTGCAGTGTTATGCATGAGGCCCTGCATAACCACTATACC

CAGAAGAGTCTGAGCCTGAGTCCTGGCAAAGGTGGATCCGCAGGCAGTGCAGGTAGTGCCG

GCAGCGGTGGTAGTGAGGTTCAGCTGCAGGAAAGCGGCGGCGGCTTAATGCAGCCTGGCGG

TAGCATGAAGCTGAGCTGCGTGGCCAGCGGCTTCACCTTTAGCAATTACTGGATGAACTGG

GTGCGCCAGAGCCCGGAAAAAGGCCTGGAATGGGTGGCAGAGATCCGTCTGAAGAGCAACA

ACTACGCCACCCACTATGCCGAAAGCGTGAAGGGTCGCTTTACCATCAGCCGCGATGACAG

CAAACGCAGCGTGTATCTGCAGATGAACACCCTGCGTGCAGAGGACACCGGCATCTATTAT

TGCACCCGCGGCAACGGTAATTATCGCGCCATGGACTACTGGGGTCAGGGTACCAGCGTGA

CCGTTAGCAGTGGCGGTGGTGGTAGCGGTGGTGGTGGTAGCGGTGGTGGTGGCAGCGATAT

TCAAATGACCCAGAGCCCTGCCAGCCTGAGCGTGAGTGTTGGCGAAACCGTGAGCATCACC

TGCCGCGCCAGCGAGAACATCTATAGTAGCCTGGCCTGGTACCAGCAGAAACAGGGCAAAA

GCCCGCAGCTGCTGGTGTATAGCGCAACCATTCTGGCAGATGGCGTTCCGAGCCGTTTTAG

CGGTAGCGGCAGCGGCACACAGTACAGCCTGAAGATCAACAGCCTGCAGAGCGAGGACTTT

GGCACCTATTACTGCCAGCACTTTTGGGGTACCCCGTATACCTTCGGCGGCGGCACCAAAC

TGGAAATTAAATAA
```

Combined (SEQ ID NO: 25 and 26):
```
gaagttcaactggttgagagtggcggtggcttagttcaaccgggcggtagtttacgcctg
 E   V   Q   L   V   E   S   G   G   G   L   V   Q   P   G   G   S   L   R   L agttgtgcagccagcggtttcgccttcaactattatgacatgttttgggtgcgccaggca
 S   C   A   A   S   G   F   A   F   N   Y   Y   D   M   F   W   V   R   Q   A ccgggtaaaggcctggagtgggtggcctatatcaaaccgggcggtggcaacacctattac
 P   G   K   G   L   E   W   V   A   Y   I   K   P   G   G   G   N   T   Y   Y gccgatagcgtgaaaggtcgctttaccatcagcgcagataccagcaagaataccgcctac
 A   D   S   V   K   G   R   F   T   I   S   A   D   T   S   K   N   T   A   Y ctgcagatgaatagcctgcgtgccgaagacaccgccgtttattattgcgcccgccagctg
 L   Q   M   N   S   L   R   A   E   D   T   A   V   Y   Y   C   A   R   Q   L tacggcaatagcttttttcgattactggggccagggcaccctggttaccgttagcagcgct
 Y   G   N   S   F   F   D   Y   W   G   Q   G   T   L   V   T   V   S   S   A agcaccaagggtccgagcgtgtttcctctggcacctagcagtaaaagcaccagtggtggt
 S   T   K   G   P   S   V   F   P   L   A   P   S   S   K   S   T   S   G   G acagcagccctgggttgcctggtgaaggattactttccggagccggtgaccgttagttgg
 T   A   A   L   G   C   L   V   K   D   Y   F   P   E   P   V   T   V   S   W aatagcggcgccctgaccagtggcgttcatacatttccggccgtgctgcagagtagtggc
 N   S   G   A   L   T   S   G   V   H   T   F   P   A   V   L   Q   S   S   G ctgtacagcctgagtagcgttgttaccgttccgagcagcagcctgggcacccagacctat
 L   Y   S   L   S   S   V   V   T   V   P   S   S   S   L   G   T   Q   T   Y atttgcaatgttaaccataaaccgagcaacacaaaagttgataaaaaagttgaaccgaag
 I   C   N   V   N   H   K   P   S   N   T   K   V   D   K   K   V   E   P   K agctgtgacaaaacccatacatgtgacaaaacacacacctgcccgccttgtccggcacct
 S   C   D   K   T   H   T   C   D   K   T   H   T   C   P   P   C   P   A   P gagctgctgggtcgcccgagcgttttttctgtttcctccgaaaccgaaagacaccctgatg
 E   L   L   G   R   P   S   V   F   L   F   P   P   K   P   K   D   T   L   M
```

```
atcagccgcacacctgaggtgacctgtgttgtggtggatgtgagccacgaagatcctgaa
 I   S   R   T   P   E   V   T   C   V   V   V   D   V   S   H   E   D   P   E gttaagtttaactggtatgtggatggcgtggaggtgcataatgccaagacaaagccgcgt
 V   K   F   N   W   Y   V   D   G   V   E   V   H   N   A   K   T   K   P   R gaagagcagtacaacagcacctatcgtgttgttagtgtgctgaccgttctgcaccaagat
 E   E   Q   Y   N   S   T   Y   R   V   V   S   V   L   T   V   L   H   Q   D tggctgaacggcaaggagtatAaatgcaaggttagcaataaagccctgccggcccccgatc
 W   L   N   G   K   E   Y   K   C   K   V   S   N   K   A   L   P   A   P   I gagaagaccatcagcaaagccaaaggtcagccgcgtgagcctcaggtgtatacactgccg
 E   K   T   I   S   K   A   K   G   Q   P   R   E   P   Q   V   Y   T   L   P cctagccgtgaggagatgaccaagaatcaggttagcctgacctgtctggtgaaaggcttt
 P   S   R   E   E   M   T   K   N   Q   V   S   L   T   C   L   V   K   G   F tacccgagcgatatcgccgttgagtgggaaagcaatggtcagcctgagaacaactacaag
 Y   P   S   D   I   A   V   E   W   E   S   N   G   Q   P   E   N   N   Y   K accaccccgcctgttttagacagtgatggtagcttttttcttatacagcaaactgaccgtt
 T   T   P   P   V   L   D   S   D   G   S   F   F   L   Y   S   K   L   T   V gataagagccgctggcagcagggcaatgtgtttagctgcagtgttatgcatgaggccctg
 D   K   S   R   W   Q   Q   G   N   V   F   S   C   S   V   M   H   E   A   L cataaccactatacccagaagagtctgagcctgagtcctggcaaggtggatccgcaggc
 H   N   H   Y   T   Q   K   S   L   S   L   S   P   G   K   G   S   A   A   G agtgcaggtagtgccggcagcggtggtagtgaggttcagctgcaggaaagcggcggcggc
 S   A   G   S   A   G   S   G   G   S   E   V   Q   L   Q   E   S   G   G   G ttaatgcagcctggcggtagcatgaagctgagctgcgtggccagcggcttcacctttagc
 L   M   Q   P   G   G   S   M   K   L   S   C   V   A   S   G   F   T   F   S aattactggatgaactgggtgcgccagagcccggaaaaaggcctggaatgggtggcagag
 N   Y   W   M   N   W   V   R   Q   S   P   E   K   G   L   E   W   V   A   E atccgtctgaagagcaacaactacgccacccactatgccgaaagcgtgaagggtcgcttt
 I   R   L   K   S   N   N   Y   A   T   H   Y   A   E   S   V   K   G   R   F accatcagccgcgatgacagcaaacgcagcgtgtatctgcagatgaacaccctgcgtgca
 T   I   S   R   D   D   S   K   R   S   V   Y   L   Q   M   N   T   L   R   A gaggacaccggcatctattattgcacccgcggcaacggtaattatcgcgccatggactac
 E   D   T   G   I   Y   Y   C   T   R   G   N   G   N   Y   R   A   M   D   Y tggggtcagggtaccagcgtgaccgttagcagtggcggtggtggtagcggtggtggtggt
 W   G   Q   G   T   S   V   T   V   S   S   G   G   G   G   S   G   G   G   G agcggtggtggtggcagcgatattcaaatgacccagagccctgccagcctgagcgtgagt
 S   G   G   G   G   S   D   I   Q   M   T   S   P   A   S   L   S   V   S gttggcgaaaccgtgagcatcacctgccgcgccagcgagaacatctatagtagcctggcc
 V   G   E   T   V   S   I   T   C   R   A   S   E   N   I   Y   S   S   L   A tggtaccagcagaaacagggcaaaagcccgcagctgctggtgtatagcgcaaccattctg
 W   Y   Q   Q   K   Q   G   K   S   P   Q   L   L   V   Y   S   A   T   I   L gcagatggcgttccgagccgttttagcggtagcggcagcggcacacagtacagcctgaag
 A   D   G   V   P   S   R   F   S   G   S   G   S   G   T   Q   Y   S   L   K atcaacagcctgcagagcgaggactttggcacctattactgccagcacttttggggtacc
 I   N   S   L   Q   S   E   D   F   G   T   Y   Y   C   Q   H   F   W   G   T ccgtataccttcggcggcggcaccaaactggaaattaaataa
 P   Y   T   F   G   G   G   T   K   L   E   I   K   -

F4-2G4 LC C' Fusion Sequence - Amino Acid (SEQ ID NO: 27):
DIQMTQSPSSLSASVGDRVTITCKASQDVTTAVAWYQQKPGKAPKLLIYWASTR

HTGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGGGLMQPGGSMKLSCVASGFTFSNYWMNWVRQSPEKGLEWVAEIRLKSNNYATHYAESV
```

-continued

```
KGRFTISRDDSKRSVYLQMNTLRAEDTGIYYCTRGNGNYRAMDYWGQGTSVTVSSGGGGSG

GGGSGGGGSDIQMTQSPASLSVSVGETVSITCRASENIYSSLAWYQQKQGKSPQLLVYSAT

ILADGVPSRFSGSGSGTQYSLKINSLQSEDFGTYYCQHFWGTPYTFGGGTKLEIK
```

Underlined region is glycine-rich linker polypeptide. Bold region is fusion linker polypeptide.

```
Nucleotide (SEQ ID NO: 28):
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTATCAGCAGA

AACCGGGTAAGGCCCCGAAGCTGCTGATCTATTGGGCCAGTACCCGCCACACCGGTGTTCC

TAGTCGCTTCAGTGGCAGTGGCAGCGGCACAGATTTCACCCTGACCATCAGCAGCCTGCAA

CCGGAAGATTTTGCCACCTACTACTGCCAGCAGCACTATAGCACCCCGCTGACCTTTGGCC

AGGGCACCAAGGTTGAGATTAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCAG

GCAGTGCAGGTAGTGCCGGCAGCGGTGGTAGTGAGGTTCAGCTGCAGGAAAGCGGCGGCGG

CTTAATGCAGCCTGGCGGTAGCATGAAGCTGAGCTGCGTGGCCAGCGGCTTCACCTTTAGC

AATTACTGGATGAACTGGGTGCGCCAGAGCCCGGAAAAAGGCCTGGAATGGGTGGCAGAGA

TCCGTCTGAAGAGCAACAACTACGCCACCCACTATGCCGAAAGCGTGAAGGGTCGCTTTAC

CATCAGCCGCGATGACAGCAAACGCAGCGTGTATCTGCAGATGAACACCCTGCGTGCAGAG

GACACCGGCATCTATTATTGCACCCGCGGCAACGGTAATTATCGCGCCATGGACTACTGGG

GTCAGGGTACCAGCGTGACCGTTAGCAGTGGCGGTGGTGGTAGCGGTGGTGGTGGTAGCGG

TGGTGGTGGCAGCGATATTCAAATGACCCAGAGCCCTGCCAGCCTGAGCGTGAGTGTTGGC

GAAACCGTGAGCATCACCTGCCGCGCCAGCGAGAACATCTATAGTAGCCTGGCCTGGTACC

AGCAGAAACAGGGCAAAAGCCCGCAGCTGCTGGTGTATAGCGCAACCATTCTGGCAGATGG

CGTTCCGAGCCGTTTTAGCGGTAGCGGCAGCGGCACACAGTACAGCCTGAAGATCAACAGC

CTGCAGAGCGAGGACTTTGGCACCTATTACTGCCAGCACTTTTGGGGTACCCCGTATACCT

TCGGCGGCGGCACCAAACTGGAAATTAAATAA

Combined (SEQ ID NO: 27 and 28):
gacattcagatgacccaaagtccgagcagcctgagtgccagtgttggtgatcgcgtgaca
 D   I   Q   M   T   Q   S   P   S   S   L   S   A   S   V   G   D   R   V   T atcacatgcaaggccagtcaggacgtgaccaccgcagtggcctggtatcagcagaaaccg
 I   T   C   K   A   S   Q   D   V   T   T   A   V   A   W   Y   Q   Q   K   P ggtaaggccccgaagctgctgatctattgggccagtacccgccacaccggtgttcctagt
 G   K   A   P   K   L   L   I   Y   W   A   S   T   R   H   T   G   V   P   S cgcttcagtggcagtggcagcggcacagatttcaccctgaccatcagcagcctgcaaccg
 R   F   S   G   S   G   S   G   T   D   F   T   L   T   I   S   S   L   Q   P gaagattttgccacctactactgccagcagcactatagcaccccgctgacctttggccag
 E   D   F   A   T   Y   Y   C   Q   Q   H   Y   S   T   P   L   T   F   G   Q ggcaccaaggttgagattaaacgtacggtggcagcaccgagcgtgtttatctttccgccg
 G   T   K   V   E   I   K   R   T   V   A   A   P   S   V   F   I   F   P   P
```

```
agcgacgaacaactgaaaagtggcacagccagcgtggtgtgtttactgaacaacttctat
 S  D  E  Q  L  K  S  G  T  A  S  V  V  C  L  L  N  N  F  Y cctcgcgaggccaaggtgcagtggaaagtggacaatgcactgcagagtggcaatagccag
 P  R  E  A  K  V  Q  W  K  V  D  N  A  L  Q  S  G  N  S  Q gagagcgtgaccgaacaggatagcaaagatagcacctatagcctgagtagcaccctgacc
 E  S  V  T  E  Q  D  S  K  D  S  T  Y  S  L  S  S  T  L  T ctgagcaaggccgattatgagaagcacaaggtgtatgcatgcgaggttacccatcagggc
 L  S  K  A  D  Y  E  K  H  K  V  Y  A  C  E  V  T  H  Q  G ctgagcagcccggtgaccaaaagctttaaccgtggcgaatgcggtggtagtggtggatcc
 L  S  S  P  V  T  K  S  F  N  R  G  E  C  G  G  S  G  G  S gcaggcagtgcaggtagtgccggcagcggtggtagtgaggttcagctgcaggaaagcggc
 A  G  S  A  G  S  A  G  S  G  G  S  E  V  Q  L  Q  E  S  G ggcggcttaatgcagcctggcggtagcatgaagctgagctgcgtggccagcggcttcacc
 G  G  L  M  Q  P  G  G  S  M  K  L  S  C  V  A  S  G  F  T tttagcaattactggatgaactgggtgcgccagagcccggaaaaaggcctggaatgggtg
 F  S  N  Y  W  M  N  W  V  R  Q  S  P  E  K  G  L  E  W  V gcagagatccgtctgaagagcaacaactacgccacccactatgccgaaagcgtgaagggt
 A  E  I  R  L  K  S  N  N  Y  A  T  H  Y  A  E  S  V  K  G cgctttaccatcagccgcgatgacagcaaacgcagcgtgtatctgcagatgaacaccctg
 R  F  T  I  S  R  D  D  S  K  R  S  V  Y  L  Q  M  N  T  L cgtgcagaggacaccggcatctattattgcacccgcggcaacggtaattatcgcgccatg
 R  A  E  D  T  G  I  Y  Y  C  T  R  G  N  G  N  Y  R  A  M gactactggggtcagggtaccagcgtgaccgttagcagtggcggtggtggtagcggtggt
 D  Y  W  G  Q  G  T  S  V  T  V  S  S  G  G  G  G  S  G  G ggtggtagcggtggtggtggcagcgatattcaaatgacccagagccctgccagcctgagc
 G  G  S  G  G  G  G  S  D  I  Q  M  T  Q  S  P  A  S  L  S ggagtgttggcgaaaccgtgagcatcacctgccgcgccagcgagaacatctatagtagc
 V  S  V  G  E  T  V  S  I  T  C  R  A  S  E  N  I  Y  S  S ctggcctggtaccagcagaaacagggcaaaagcccgcagctgctggtgtatagcgcaacc
 L  A  W  Y  Q  Q  K  Q  G  K  S  P  Q  L  L  V  Y  S  A  T attctggcagatggcgttccgagccgttttagcggtagcggcagcggcacacagtacagc
 I  L  A  D  G  V  P  S  R  F  S  G  S  G  S  G  T  Q  Y  S ctgaagatcaacagcctgcagagcgaggactttggcacctattactgccagcacttttgg
 L  K  I  N  S  L  Q  S  E  D  F  G  T  Y  Y  C  Q  H  F  W gtaccccgtataccttcggcggcggcaccaaactggaaattaaataa
 G  T  P  Y  T  F  G  G  G  T  K  L  E  I  K  -

E10-2G4 LC C' Fusion Sequence - Amino Acid (SEQ ID NO: 29):
DIQMTQSPSSLSASVGDRVTITCKASQDVTTAVAWYQQKPGKAPKLLIYWASRL

HNGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGGGLMQPGGSMKLSCVASGFTFSNYWMNWVRQSPEKGLEWVAEIRLKSNNYATHYAESV

KGRFTISRDDSKRSVYLQMNTLRAEDTGIYYCTRGNGNYRAMDYWGQGTSVTVSSGGGGSG

GGSGGGGSDIQMTQSPASLSVSVGETVSITCRASENIYSSLAWYQQKGKSPQLLVYSAT

ILADGVPSRFSGSGSGTQYSLKINSLQSEDFGTYYCQHFWGTPYTFGGGTKLEIK
```

Underlined region is glycine-rich linker polypeptide. Bold region is fusion linker polypeptide.

```
Nucleotide (SEQ ID NO: 30):
GATATCCAGATGACCCAGTCCCCGAGCTCCCTGTCCGCCTCTGTGGGCGATAGG

GTCACCATCACCTGCCGGGCGAGCCAGGATGTGACCACCGCTGTAGCCTGGTATCAACAGA

AACCAGGAAAAGCTCCGAAGCTTCTGATTTACTGGGCGAGCCGTCTTCATAATGGCGTGCC

GAGCCGCTTTAGCGGCAGCGGCTCCGGGACGGATTTCACTCTGACCATCAGCAGTCTGCAG

CCGGAAGACTTCGCAACTTATTACTGTCAGCAACATTATAGCACCCCGCTGACGTTCGGAC

AGGGTACCAAGGTGGAGATCAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCAG

GCAGTGCAGGTAGTGCCGGCAGCGGTGGTAGTGAGGTTCAGCTGCAGGAAAGCGGCGGCGG

CTTAATGCAGCCTGGCGGTAGCATGAAGCTGAGCTGCGTGGCCAGCGGCTTCACCTTTAGC

AATTACTGGATGAACTGGGTGCGCCAGAGCCCGGAAAAAGGCCTGGAATGGGTGGCAGAGA

TCCGTCTGAAGAGCAACAACTACGCCACCCACTATGCCGAAAGCGTGAAGGGTCGCTTTAC

CATCAGCCGCGATGACAGCAAACGCAGCGTGTATCTGCAGATGAACACCCTGCGTGCAGAG

GACACCGGCATCTATTATTGCACCCGCGGCAACGGTAATTATCGCGCCATGGACTACTGGG

GTCAGGGTACCAGCGTGACCGTTAGCAGTGGCGGTGGTGGTAGCGGTGGTGGTGGTAGCGG

TGGTGGTGGCAGCGATATTCAAATGACCCAGAGCCCTGCCAGCCTGAGCGTGAGTGTTGGC

GAAACCGTGAGCATCACCTGCCGCGCCAGCGAGAACATCTATAGTAGCCTGGCCTGGTACC

AGCAGAAACAGGGCAAAAGCCCGCAGCTGCTGGTGTATAGCGCAACCATTCTGGCAGATGG

CGTTCCGAGCCGTTTTAGCGGTAGCGGCAGCGGCACACAGTACAGCCTGAAGATCAACAGC

CTGCAGAGCGAGGACTTTGGCACCTATTACTGCCAGCACTTTTGGGGTACCCCGTATACCT

TCGGCGGCGGCACCAAACTGGAAATTAAATAA

Combined (SEQ ID NO: 29 and 30):
gatatccagatgacccagtccccgagctccctgtccgcctctgtgggcgatagggtcacc
 D   I   Q   M   T   Q   S   P   S   S   L   S   A   S   V   G   D   R   V   T atcacctgccgggcgagccaggatgtgaccaccgctgtagcctggtatcaacagaaacca
 I   T   C   R   A   S   Q   D   V   T   T   A   V   A   W   Y   Q   Q   K   P ggaaaagctccgaagcttctgatttactgggcgagccgtcttcataatggcgtgccgagc
 G   K   A   P   K   L   L   I   Y   W   A   S   R   L   H   N   G   V   P   S cgctttagcggcagcggctccgggacggatttcactctgaccatcagcagtctgcagccg
 R   F   S   G   S   G   S   G   T   D   F   T   L   T   I   S   S   L   Q   P gaagacttcgcaacttattactgtcagcaacattatagcaccccgctgacgttcggacag
 E   D   F   A   T   Y   Y   C   Q   Q   H   Y   S   T   P   L   T   F   G   Q ggtaccaaggtggagatcaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T
```

```
ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S gcaggcagtgcaggtagtgccggcagcggtggtagtgaggttcagctgcaggaaagcggc
 A   G   S   A   G   S   A   G   S   G   G   S   E   V   Q   L   Q   E   S   G ggcggcttaatgcagcctggcggtagcatgaagctgagctgcgtggccagcggcttcacc
 G   G   L   M   Q   P   G   G   S   M   K   L   S   C   V   A   S   G   F   T tttagcaattactggatgaactgggtgcgccagagcccggaaaaaggcctggaatgggtg
 F   S   N   Y   W   M   N   W   V   R   Q   S   P   E   K   G   L   E   W   V gcagagatccgtctgaagagcaacaactacgccacccactatgccgaaagcgtgaagggt
 A   E   I   R   L   K   S   N   N   Y   A   T   H   Y   A   E   S   V   K   G cgctttaccatcagccgcgatgacagcaaacgcagcgtgtatctgcagatgaacaccctg
 R   F   T   I   S   R   D   D   S   K   R   S   V   Y   L   Q   M   N   T   L cgtgcagaggacaccggcatctattattgcacccgcggcaacggtaattatcgcgccatg
 R   A   E   D   T   G   I   Y   Y   C   T   R   G   N   G   N   Y   R   A   M gactactggggtcagggtaccagcgtgaccgttagcagtggcggtggtggtagcggtggt
 D   Y   W   G   Q   G   T   S   V   T   V   S   S   G   G   G   G   S   G   G ggtggtagcggtggtggtggcagcgatattcaaatgacccagagccctgccagcctgagc
 G   G   S   G   G   G   G   S   D   I   Q   M   T   Q   S   P   A   S   L   S gtgagtgttggcgaaaccgtgagcatcacctgccgcgccagcgagaacatctatagtagc
 V   S   V   G   E   T   V   S   I   T   C   R   A   S   E   N   I   Y   S   S ctggcctggtaccagcagaaacagggcaaaagcccgcagctgctggtgtatagcgcaacc
 L   A   W   Y   Q   Q   K   Q   G   K   S   P   Q   L   L   V   Y   S   A   T attctggcagatggcgttccgagccgttttagcggtagcggcagcggcacacagtacagc
 I   L   A   D   G   V   P   S   R   F   S   G   S   G   S   G   T   Q   Y   S ctgaagatcaacagcctgcagagcgaggactttggcacctattactgccagcacttttgg
 L   K   I   N   S   L   Q   S   E   D   F   G   T   Y   Y   C   Q   H   F   W ggtaccccgtataccttcggcggcggcaccaaactggaaattaaataa
 G   T   P   Y   T   F   G   G   G   T   K   L   E   I   K   -
```

F4-4G7 HC C' Fusion Sequence - Amino Acid (SEQ ID NO: 31):
EVQLVESGGGLVQPGGSLRLSCAASGFAFNYYDMFWVRQAPGKGLEWVAYIKPG

GGNTYYADSVKGRFTISADTSKNTAYLQMNSLRAEDTAVYYCARQLYGNSFFDYWGQGTLV

TVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCDKTHTCPPC

PAPELLGRPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGKGGSAGSAGSAGSGGSEVQLQESGPEL

EMPGASVKISCKASGSSFTGFSMNWVKQSNGKSLEWIGNIDTYYGGTTYNQKFKGKATLTV

DKSSSTAYMQLKSLTSEDSAVYYCARSAYYGSTFAYWQGTLVTVSA<u>GGGGSGGGGSGGGGS</u>

DIQMTQSPASLSASVGETVTITCRASENIYSYLAWYQQKQGKSPQLLVYNAKTLIEGVPSR

FSGSGSGTQFSLKINSLQPEDFGSYFCQHHFGTPFTFGSGTELEIK

Underlined region is glycine-rich linker polypeptide. Bold region is fusion linker polypeptide.

Nucleotide (SEQ ID NO: 32):
GAAGTTCAACTGGTTGAGAGTGGCGGTGGCTTAGTTCAACCGGGCGGTAGTTTA

CGCCTGAGTTGTGCAGCCAGCGGTTTCGCCTTCAACTATTATGACATGTTTTGGGTGCGCC

```
AGGCACCGGGTAAAGGCCTGGAGTGGGTGGCCTATATCAAACCGGGCGGTGGCAACACCTA

TTACGCCGATAGCGTGAAAGGTCGCTTTACCATCAGCGCAGATACCAGCAAGAATACCGCC

TACCTGCAGATGAATAGCCTGCGTGCCGAAGACACCGCCGTTTATTATTGCGCCCGCCAGC

TGTACGGCAATAGCTTTTTCGATTACTGGGGCCAGGGCACCCTGGTTACCGTTAGCAGCGC

TAGCACCAAGGGTCCGAGCGTGTTTCCTCTGGCACCTAGCAGTAAAAGCACCAGTGGTGGT

ACAGCAGCCCTGGGTTGCCTGGTGAAGGATTACTTTCCGGAGCCGGTGACCGTTAGTTGGA

ATAGCGGCGCCCTGACCAGTGGCGTTCATACATTTCCGGCCGTGCTGCAGAGTAGTGGCCT

GTACAGCCTGAGTAGCGTTGTTACCGTTCCGAGCAGCAGCCTGGGCACCCAGACCTATATT

TGCAATGTTAACCATAAACCGAGCAACACAAAAGTTGATAAAAAAGTTGAACCGAAGAGCT

GTGACAAAACCCATACATGTGACAAAACACACACCTGCCCGCCTTGTCCGGCACCTGAGCT

GCTGGGTCGCCCGAGCGTTTTTCTGTTTCCTCCGAAACCGAAAGACACCCTGATGATCAGC

CGCACACCTGAGGTGACCTGTGTTGTGGTGGATGTGAGCCACGAAGATCCTGAAGTTAAGT

TTAACTGGTATGTGGATGGCGTGGAGGTGCATAATGCCAAGACAAAGCCGCGTGAAGAGCA

GTACAACAGCACCTATCGTGTTGTTAGTGTGCTGACCGTTCTGCACCAAGATTGGCTGAAC

GGCAAGGAGTATAAATGCAAGGTTAGCAATAAAGCCCTGCCGGCCCCGATCGAGAAGACCA

TCAGCAAAGCCAAAGGTCAGCCGCGTGAGCCTCAGGTGTATACACTGCCGCCTAGCCGTGA

GGAGATGACCAAGAATCAGGTTAGCCTGACCTGTCTGGTGAAAGGCTTTTACCCGAGCGAT

ATCGCCGTTGAGTGGGAAAGCAATGGTCAGCCTGAGAACAACTACAAGACCACCCCGCCTG

TTTTAGACAGTGATGGTAGCTTTTTCTTATACAGCAAACTGACCGTTGATAAGAGCCGCTG

GCAGCAGGGCAATGTGTTTAGCTGCAGTGTTATGCATGAGGCCCTGCATAACCACTATACC

CAGAAGAGTCTGAGCCTGAGTCCTGGCAAAGGTGGATCCGCCGGTAGCGCAGGCAGCGCAG

GTAGTGGTGGTAGCGAAGTTCAGCTGCAGGAAAGTGGCCCGGAACTGGAAATGCCGGGCGC

CAGCGTGAAAATCAGTTGCAAAGCCAGCGGTAGCAGCTTCACAGGCTTCAGCATGAACTGG

GTGAAGCAGAGCAACGGTAAGAGCCTGGAGTGGATCGGCAACATTGACACCTACTATGGCG

GCACCACCTACAACCAGAAGTTCAAAGGCAAGGCCACCCTGACCGTGGATAAAAGCAGCAG

CACAGCCTACATGCAGCTGAAAAGCCTGACCAGCGAAGATAGCGCCGTGTATTACTGCGCC

CGTAGCGCCTATTACGGCAGCACCTTTGCATACTGGCAGGGTACCCTGGTGACCGTGAGCG

CAGGTGGTGGTGGTAGTGGTGGTGGTGGTAGCGGTGGTGGCGGTAGTGACATTCAAATGAC

CCAGAGCCCTGCAAGCCTGAGCGCCAGTGTTGGCGAAACCGTGACCATTACATGCCGCGCC

AGCGAAAACATCTATAGTTACCTGGCCTGGTACCAGCAGAAACAGGGCAAAAGCCCGCAAC

TGCTGGTGTATAACGCCAAAACCCTGATTGAGGGCGTGCCGAGTCGCTTCAGCGGTAGCGG

TAGCGGTACACAGTTCAGTCTGAAAATCAACAGCCTGCAGCCGGAAGACTTCGGCAGCTAC

TTTTGCCAGCACCACTTTGGCACCCCGTTTACATTTGGCAGCGGCACCGAGCTGGAAATTA

AATAA

Combined (SEQ ID NO: 31 and 32):
gaagttcaactggttgagagtggcggtggcttagttcaaccgggcggtagtttacgcctg
 E   V   Q   L   V   E   S   G   G   G   L   V   Q   P   G   G   S   L   R   L agttgtgcagccagcggtttcgccttcaactattatgacatgttttgggtgcgccaggca
 S   C   A   A   S   G   F   A   F   N   Y   Y   D   M   F   W   V   R   Q   A ccgggtaaaggcctggagtgggtggcctatatcaaaccgggcggtggcaacacctattac
 P   G   K   G   L   E   W   V   A   Y   I   K   P   G   G   G   N   T   Y   Y gccgatagcgtgaaaggtcgctttaccatcagcgcagataccagcaagaataccgcctac
 A   D   S   V   K   G   R   F   T   I   S   A   D   T   S   K   N   T   A   Y
```

-continued

```
ctgcagatgaatagcctgcgtgccgaagacaccgccgtttattattgcgcccgccagctg
L  Q  M  N  S  L  R  A  E  D  T  A  V  Y  Y  C  A  R  Q  L tacggcaatagcttttcgattactggggccagggcaccctggttaccgttagcagcgct
Y  G  N  S  F  F  D  Y  W  G  Q  G  T  L  V  T  V  S  S  A agcaccaagggtccgagcgtgtttcctctggcacctagcagtaaaagcaccagtggtggt
S  T  K  G  P  S  V  F  P  L  A  P  S  S  K  S  T  S  G  G acagcagccctgggttgcctggtgaaggattactttccggagccggtgaccgttagttgg
T  A  A  L  G  C  L  V  K  D  Y  F  P  E  P  V  T  V  S  W aatagcggcgccctgaccagtggcgttcatacatttccggccgtgctgcagagtagtggc
N  S  G  A  L  T  S  G  V  H  T  F  P  A  V  L  Q  S  S  G ctgtacagcctgagtagcgttgttaccgttccgagcagcagcctgggcacccagacctat
L  Y  S  L  S  S  V  V  T  V  P  S  S  S  L  G  T  Q  T  Y atttgcaatgttaaccataaaccgagcaacacaaaagttgataaaaaagttgaaccgaag
I  C  N  V  N  H  K  P  S  N  T  K  V  D  K  K  V  E  P  K agctgtgacaaaacccatacatgtgacaaaacacacacctgcccgccttgtccggcacct
S  C  D  K  T  H  T  C  D  K  T  H  T  C  P  P  C  P  A  P gagctgctgggtcgcccgagcgttttctgtttcctccgaaaccgaaagacaccctgatg
E  L  L  G  R  P  S  V  F  L  F  P  P  K  P  K  D  T  L  M atcagccgcacacctgaggtgacctgtgttgtggtggatgtgagccacgaagatcctgaa
I  S  R  T  P  E  V  T  C  V  V  V  D  V  S  H  E  D  P  E gttaagtttaactggtatgtggatggcgtggaggtgcataatgccaagacaaagccgcgt
V  K  F  N  W  Y  V  D  G  V  E  V  H  N  A  K  T  K  P  R gaagagcagtacaacagcacctatcgtgttgttagtgtgctgaccgttctgcaccaagat
E  E  Q  Y  N  S  T  Y  R  V  V  S  V  L  T  V  L  H  Q  D tggctgaacggcaaggagtatataaatgcaaggttagcaataaagcccctgccggccccgatc
W  L  N  G  K  E  Y  K  C  K  V  S  N  K  A  L  P  A  P  I gagaagaccatcagcaaagccaaaggtcagccgcgtgagcctcaggtgtatacactgccg
E  K  T  I  S  K  A  K  G  Q  P  R  E  P  Q  V  Y  T  L  P cctagccgtgaggagatgaccaagaatcaggttagcctgacctgtctggtgaaaggcttt
P  S  R  E  E  M  T  K  N  Q  V  S  L  T  C  L  V  K  G  F tacccgagcgatatcgccgttgagtggaaagcaatggtcagcctgagaacaactacaag
Y  P  S  D  I  A  V  E  W  E  S  N  G  Q  P  E  N  N  Y  K accacccgcctgttttagacagtgatggtagctttttcttatacagcaaactgaccgtt
T  T  P  P  V  L  D  S  D  G  S  F  F  L  Y  S  K  L  T  V gataagagccgctggcagcagggcaatgtgtttagctgcagtgttatgcatgaggccctg
D  K  S  R  W  Q  Q  G  N  V  F  S  C  S  V  M  H  E  A  L cataaccactatacccagaagagtctgagcctgagtcctggcaaaggtggatccgccggt
H  N  H  Y  T  Q  K  S  L  S  L  S  P  G  K  G  G  S  A  G agcgcaggcagcgcaggtagtggtggtagcgaagttcagctgcaggaaagtggcccggaa
S  A  G  S  A  G  S  G  G  S  E  V  Q  L  Q  E  S  G  P  E ctggaaatgccgggcgccagcgtgaaaatcagttgcaaagccagcggtagcagcttcaca
L  E  M  P  G  A  S  V  K  I  S  C  K  A  S  G  S  S  F  T ggcttcagcatgaactgggtgaagcagagcaacggtaagagcctggagtggatcggcaac
G  F  S  M  N  W  V  K  Q  S  N  G  K  S  L  E  W  I  G  N attgacacctactatggcggcaccacctacaaccagaagttcaaaggcaaggccaccctg
I  D  T  Y  Y  G  G  T  T  Y  N  Q  K  F  K  G  K  A  T  L accgtggataaaagcagcagcacagcctacatgcagctgaaaagcctgaccagcgaagat
T  V  D  K  S  S  S  T  A  Y  M  Q  L  K  S  L  T  S  E  D agcgccgtgtattactgcgcccgtagcgcctattacggcagcacctttgcatactggcag
S  A  V  Y  Y  C  A  R  S  A  Y  Y  G  S  T  F  A  Y  W  Q ggtaccctggtgaccgtgagcgcaggtggtggtggtagtggtggtggtggtagcggtggt
G  T  L  V  T  V  S  A  G  G  G  G  S  G  G  G  G  S  G  G ggcggtagtgacattcaaatgacccagagccctgcaagcctgagcgccagtgttggcgaa
G  G  S  D  I  Q  M  T  Q  S  P  A  S  L  S  A  S  V  G  E
```

-continued

```
accgtgaccattacatgccgcgccagcgaaaacatctatagttacctggcctggtaccag
 T  V  T  I  T  C  R  A  S  E  N  I  Y  S  Y  L  A  W  Y  Q cagaaacagggcaaaagcccgcaactgctggtgtataacgccaaaaccctgattgagggc
 Q  K  Q  G  K  S  P  Q  L  L  V  Y  N  A  K  T  L  I  E  G gtgccgagtcgcttcagcggtagcggtagcggtacacagttcagtctgaaaatcaacagc
 V  P  S  R  F  S  G  S  G  S  G  T  Q  F  S  L  K  I  N  S ctgcagccggaagacttcggcagctactttttgccagcaccactttggcaccccgtttaca
 L  Q  P  E  D  F  G  S  Y  F  C  Q  H  H  F  G  T  P  F  T tttggcagcggcaccgagctggaaattaaataa
 F  G  S  G  T  E  L  E  I  K  -

F4-4G7 LC C' Fusion Sequence - Amino Acid (SEQ ID NO: 33):
DIQMTQSPSSLSASVGDRVTITCKASQDVTTAVAWYQQKPGKAPKLLIYWASTR

HTGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGPELEMPGASVKISCKASGSSFTGFSMNWVKQSNGKSLEWIGNIDTYYGGTTYNQKFKG

KATLTVDKSSSTAYMQLKSLTSEDSAVYYCARSAYYGSTFAYWQGTLVTVSAGGGGSGGGG

SGGGGSDIQMTQSPASLSASVGETVTITCRASENIYSYLAWYQQKGKSPQLLVYNAKTLI

EGVPSRFSGSGSGTQFSLKINSLQPEDFGSYFCQHHFGTPFTFGSGTELEIK
```

Underlined region is glycine-rich linker polypeptide. Bold region is fusion linker polypeptide.

```
Nucleotide (SEQ ID NO: 34):
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTATCAGCAGA

AACCGGGTAAGGCCCCGAAGCTGCTGATCTATTGGGCCAGTACCCGCCACACCGGTGTTCC

TAGTCGCTTCAGTGGCAGTGGCAGCGGCACAGATTTCACCCTGACCATCAGCAGCCTGCAA

CCGGAAGATTTTGCCACCTACTACTGCCAGCAGCACTATAGCACCCCGCTGACCTTTGGCC

AGGGCACCAAGGTTGAGATTAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCCG

GTAGCGCAGGCAGCGCAGGTAGTGGTGGTAGCGAAGTTCAGCTGCAGGAAAGTGGCCCGGA

ACTGGAAATGCCGGGCGCCAGCGTGAAAATCAGTTGCAAAGCCAGCGGTAGCAGCTTCACA

GGCTTCAGCATGAACTGGGTGAAGCAGAGCAACGGTAAGAGCCTGGAGTGGATCGGCAACA

TTGACACCTACTATGGCGGCACCACCTACAACCAGAAGTTCAAAGGCAAGGCCACCCTGAC

CGTGGATAAAAGCAGCAGCACAGCCTACATGCAGCTGAAAAGCCTGACCAGCGAAGATAGC

GCCGTGTATTACTGCGCCCGTAGCGCCTATTACGGCAGCACCTTTGCATACTGGCAGGGTA

CCCTGGTGACCGTGAGCGCAGGTGGTGGTGGTAGTGGTGGTGGTGGTAGCGGTGGTGGCGG

TAGTGACATTCAAATGACCCAGAGCCCTGCAAGCCTGAGCGCCAGTGTTGGCGAAACCGTG

ACCATTACATGCCGCGCCAGCGAAAACATCTATAGTTACCTGGCCTGGTACCAGCAGAAAC

AGGGCAAAAGCCCGCAACTGCTGGTGTATAACGCCAAAACCCTGATTGAGGGCGTGCCGAG
```

TCGCTTCAGCGGTAGCGGTAGCGGTACACAGTTCAGTCTGAAAATCAACAGCCTGCAGCCG

GAAGACTTCGGCAGCTACTTTTGCCAGCACCACTTTGGCACCCCGTTTACATTTGGCAGCG

GCACCGAGCTGGAAATTAAATAA

Combined (SEQ ID NO: 33 and 34):
```
gacattcagatgacccaaagtccgagcagcctgagtgccagtgttggtgatcgcgtgaca
 D   I   Q   M   T   Q   S   P   S   S   L   S   A   S   V   G   D   R   V   T atcacatgcaaggccagtcaggacgtgaccaccgcagtggcctggtatcagcagaaaccg
 I   T   C   K   A   S   Q   D   V   T   T   A   V   A   W   Y   Q   Q   K   P ggtaaggccccgaagctgctgatctattgggccagtacccgccacaccggtgttcctagt
 G   K   A   P   K   L   L   I   Y   W   A   S   T   R   H   T   G   V   P   S cgcttcagtggcagtggcagcggcacagatttcaccctgaccatcagcagcctgcaaccg
 R   F   S   G   S   G   S   G   T   D   F   T   L   T   I   S   S   L   Q   P gaagatttttgccacctactactgccagcagcactatagcaccccgctgacctttggccag
 E   D   F   A   T   Y   Y   C   Q   Q   H   Y   S   T   P   L   T   F   G   Q ggcaccaaggttgagattaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S gccggtagcgcaggcagcgcaggtagtggtggtagcgaagttcagctgcaggaaagtggc
 A   G   S   A   G   S   A   G   S   G   G   S   E   V   Q   L   Q   E   S   G ccggaactggaaatgccgggcgccagcgtgaaaatcagttgcaaagccagcggtagcagc
 P   E   L   E   M   P   G   A   S   V   K   I   S   C   K   A   S   G   S   S ttcacaggcttcagcatgaactgggtgaagcagagcaacggtaagagcctggagtggatc
 F   T   G   F   S   M   N   W   V   K   Q   S   N   G   K   S   L   E   W   I ggcaacattgacacctactatggcggcaccacctacaaccagaagttcaaaggcaaggcc
 G   N   I   D   T   Y   Y   G   G   T   T   Y   N   Q   K   F   K   G   K   A accctgaccgtggataaaagcagcagcacagcctacatgcagctgaaaagcctgaccagc
 T   L   T   V   D   K   S   S   S   T   A   Y   M   Q   L   K   S   L   T   S gaagatagcgccgtgtattactgcgcccgtagcgcctattacggcagcacctttgcatac
 E   D   S   A   V   Y   Y   C   A   R   S   A   Y   Y   G   S   T   F   A   Y tggcagggtacccttggtgaccgtgagcgcaggtggtggtggtagtggtggtggtggtagc
 W   Q   G   T   L   V   T   V   S   A   G   G   G   S   G   G   G   G   S ggtggtggcggtagtgacattcaaatgacccagagccctgcaagcctgagcgccagtgtt
 G   G   G   G   S   D   I   Q   M   T   Q   S   P   A   S   L   S   A   S   V ggcgaaaccgtgaccattacatgccgcgccagcgaaaacatctatagttacctggcctgg
 G   E   T   V   T   I   T   C   R   A   S   E   N   I   Y   S   Y   L   A   W taccagcagaaacagggcaaaagcccgcaactgctggtgtataacgccaaaaccctgatt
 Y   Q   Q   K   Q   G   K   S   P   Q   L   L   V   Y   N   A   K   T   L   I gagggcgtgccgagtcgcttcagcggtagcggtagcggtacacagttcagtctgaaaatc
 E   G   V   P   S   R   F   S   G   S   G   S   G   T   Q   F   S   L   K   I aacagcctgcagccggaagacttcggcagctactttttgccagcaccactttggcaccccg
 N   S   L   Q   P   E   D   F   G   S   Y   F   C   Q   H   H   F   G   T   P tttacatttggcagcggcaccgagctggaaattaaataa
 F   T   F   G   S   G   T   E   L   E   I   K   -
```

```
F4-4G7 LC C' Fusion Sequence - Amino Acid (SEQ ID NO: 35):
DIQMTQSPSSLSASVGDRVTITCKASQDVTTAVAWYQQKPGKAPKLLIYWASTR

HTGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGPELEMPGASVKISCKASGSSFTGFSMNWVKQSNGKSLEWIGNIDTYYGGTTYNQKFKG

KATLTVDKSSSTAYMQLKSLTSEDSAVYYCARSAYYGSTFAYWQGTLVTVSAGGGGSGGGG

SGGGGSDIQMTQSPASLSASVGETVTITCRASENIYSYLAWYQQKQGKSPQLLVYNAKTLI

EGVPSRFSGSGSGTQFSLKINSLQPEDFGSYFCQHHFGTPFTFGSGTELEIK
```

Underlined region is glycine-rich linker polypeptide. Bold region is fusion linker polypeptide.

```
Nucleotide (SEQ ID NO: 36):
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTATCAGCAGA

AACCGGGTAAGGCCCCCGAAGCTGCTGATCTATTGGGCCAGTACCCGCCACACCGGTGTTCC

TAGTCGCTTCAGTGGCAGTGGCAGCGGCACAGATTTCACCCTGACCATCAGCAGCCTGCAA

CCGGAAGATTTTGCCACCTACTACTGCCAGCAGCACTATAGCACCCCGCTGACCTTTGGCC

AGGGCACCAAGGTTGAGATTAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCCG

GTAGCGCAGGCAGCGCAGGTAGTGGTGGTAGCGAAGTTCAGCTGCAGGAAAGTGGCCCGGA

ACTGGAAATGCCGGGCGCCAGCGTGAAAATCAGTTGCAAAGCCAGCGGTAGCAGCTTCACA

GGCTTCAGCATGAACTGGGTGAAGCAGAGCAACGGTAAGAGCCTGGAGTGGATCGGCAACA

TTGACACCTACTATGGCGGCACCACCTACAACCAGAAGTTCAAAGGCAAGGCCACCCTGAC

CGTGGATAAAAGCAGCAGCACAGCCTACATGCAGCTGAAAAGCCTGACCAGCGAAGATAGC

GCCGTGTATTACTGCGCCCGTAGCGCCTATTACGGCAGCACCTTTGCATACTGGCAGGGTA

CCCTGGTGACCGTGAGCGCAGGTGGTGGTGGTAGTGGTGGTGGTGGTAGCGGTGGTGGCGG

TAGTGACATTCAAATGACCCAGAGCCCTGCAAGCCTGAGCGCCAGTGTTGGCGAAACCGTG

ACCATTACATGCCGCGCCAGCGAAAACATCTATAGTTACCTGGCCTGGTACCAGCAGAAAC

AGGGCAAAAGCCCGCAACTGCTGGTGTATAACGCCAAAACCCTGATTGAGGGCGTGCCGAG

TCGCTTCAGCGGTAGCGGTAGCGGTACACAGTTCAGTCTGAAAATCAACAGCCTGCAGCCG

GAAGACTTCGGCAGCTACTTTTGCCAGCACCACTTTGGCACCCCGTTTACATTTGGCAGCG

GCACCGAGCTGGAAATTAAATAA
```

```
Combined (SEQ ID NO: 35 and 36):
gacattcagatgacccaaagtccgagcagcctgagtgccagtgttggtgatcgcgtgaca
 D  I  Q  M  T  Q  S  P  S  S  L  S  A  S  V  G  D  R  V  T atcacatgcaaggccagtcaggacgtgaccaccgcagtggcctggtatcagcagaaaccg
 I  T  C  K  A  S  Q  D  V  T  T  A  V  A  W  Y  Q  Q  K  P
```

```
ggtaaggccccgaagctgctgatctattgggccagtacccgccacaccggtgttcctagt
 G   K   A   P   K   L   L   I   Y   W   A   S   T   R   H   T   G   V   P   S cgcttcagtggcagtggcagcggcacagatttcaccctgaccatcagcagcctgcaaccg
 R   F   S   G   S   G   S   G   T   D   F   T   L   T   I   S   S   L   Q   P gaagattttgccacctactactgccagcagcactatagcaccccgctgacctttggccag
 E   D   F   A   T   Y   Y   C   Q   Q   H   Y   S   T   P   L   T   F   G   Q ggcaccaaggttgagattaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S gccggtagcgcaggcagcgcaggtagtggtggtagcgaagttcagctgcaggaaagtggc
 A   G   S   A   G   S   A   G   S   G   G   S   E   V   Q   L   Q   E   S   G ccggaactggaaatgccgggcgccagcgtgaaaatcagttgcaaagccagcggtagcagc
 P   E   L   E   M   P   G   A   S   V   K   I   S   C   K   A   S   G   S   S ttcacaggcttcagcatgaactgggtgaagcagagcaacggtaagagcctggagtggatc
 F   T   G   F   S   M   N   W   V   K   Q   S   N   G   K   S   L   E   W   I ggcaacattgacacctactatggcggcaccacctacaaccagaagttcaaaggcaaggcc
 G   N   I   D   T   Y   Y   G   G   T   T   Y   N   Q   K   F   K   G   K   A accctgaccgtggataaaagcagcagcacagcctacatgcagctgaaaagcctgaccagc
 T   L   T   V   D   K   S   S   S   T   A   Y   M   Q   L   K   S   L   T   S gaagatagcgccgtgtattactgcgcccgtagcgcctattacggcagcacctttgcatac
 E   D   S   A   V   Y   Y   C   A   R   S   A   Y   Y   G   S   T   F   A   Y tggcagggtaccctggtgaccgtgagcgcaggtggtggtggtagtggtggtggtggtagc
 W   Q   G   T   L   V   T   V   S   A   G   G   G   G   S   G   G   G   G   S ggtggtggcggtagtgacattcaaatgacccagagccctgcaagcctgagcgccagtgtt
 G   G   G   G   S   D   I   Q   M   T   Q   S   P   A   S   L   S   A   S   V ggcgaaaccgtgaccattacatgcgcgcgccagcgaaaaacatctatagttacctggcctgg
 G   E   T   V   T   I   T   C   R   A   S   E   N   I   Y   S   Y   L   A   W taccagcagaaacagggcaaaagcccgcaactgctggtgtataacgccaaaaccctgatt
 Y   Q   Q   K   Q   G   K   S   P   Q   L   L   V   Y   N   A   K   T   L   I gagggcgtgccgagtcgcttcagcggtagcggtagcggtacacagttcagtctgaaaatc
 E   G   V   P   S   R   F   S   G   S   G   S   G   T   Q   F   S   L   K   I aacagcctgcagccggaagacttcggcagctactttgccagcaccactttggcaccccg
 N   S   L   Q   P   E   D   F   G   S   Y   F   C   Q   H   H   F   G   T   P tttacatttggcagcggcaccgagctggaaattaaataa
 F   T   F   G   S   G   T   E   L   E   I   K   -
```

E10-4G7 LC C' Fusion Sequence - Amino Acid (SEQ ID NO: 37):
DIQMTQSPSSLSASVGDRVTITCKASQDVTTAVAWYQQKPGKAPKLLIYWASRL

HNGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGPELEMPGASVKISCKASGSSFTGFSMNWVKQSNGKSLEWIGNIDTYYGGTTYNQKFKG

KATLTVDKSSSTAYMQLKSLTSEDSAVYYCARSAYYGSTFAYWQGTLVTVSAGGGGSGGGG

-continued

<u>SGGGGS</u>DIQMTQSPASLSASVGETVTITCRASENIYSYLAWYQQKQGKSPQLLVYNAKTLI
EGVPSRFSGSGSGTQFSLKINSLQPEDFGSYFCQHHFGTPFTFGSGTELEIK

Underlined region is glycine-rich linker polypeptide. Bold region is fusion linker polypeptide.

```
Nucleotide (SEQ ID NO: 38):
GATATCCAGATGACCCAGTCCCCGAGCTCCCTGTCCGCCTCTGTGGGCGATAGG

GTCACCATCACCTGCCGGGCGAGCCAGGATGTGACCACCGCTGTAGCCTGGTATCAACAGA

AACCAGGAAAAGCTCCGAAGCTTCTGATTTACTGGGCGAGCCGTCTTCATAATGGCGTGCC

GAGCCGCTTTAGCGGCAGCGGCTCCGGGACGGATTTCACTCTGACCATCAGCAGTCTGCAG

CCGGAAGACTTCGCAACTTATTACTGTCAGCAACATTATAGCACCCCGCTGACGTTCGGAC

AGGGTACCAAGGTGGAGATCAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCCG

GTAGCGCAGGCAGCGCAGGTAGTGGTGGTAGCGAAGTTCAGCTGCAGGAAAGTGGCCCGGA

ACTGGAAATGCCGGGCGCCAGCGTGAAAATCAGTTGCAAAGCCAGCGGTAGCAGCTTCACA

GGCTTCAGCATGAACTGGGTGAAGCAGAGCAACGGTAAGAGCCTGGAGTGGATCGGCAACA

TTGACACCTACTATGGCGGCACCACCTACAACCAGAAGTTCAAAGGCAAGGCCACCCTGAC

CGTGGATAAAAGCAGCAGCACAGCCTACATGCAGCTGAAAAGCCTGACCAGCGAAGATAGC

GCCGTGTATTACTGCGCCCGTAGCGCCTATTACGGCAGCACCTTTGCATACTGGCAGGGTA

CCCTGGTGACCGTGAGCGCAGGTGGTGGTGGTAGTGGTGGTGGTGGTAGCGGTGGTGGCGG

TAGTGACATTCAAATGACCCAGAGCCCTGCAAGCCTGAGCGCCAGTGTTGGCGAAACCGTG

ACCATTACATGCCGCGCCAGCGAAAACATCTATAGTTACCTGGCCTGGTACCAGCAGAAAC

AGGGCAAAAGCCCGCAACTGCTGGTGTATAACGCCAAAACCCTGATTGAGGGCGTGCCGAG

TCGCTTCAGCGGTAGCGGTAGCGGTACACAGTTCAGTCTGAAAATCAACAGCCTGCAGCCG

GAAGACTTCGGCAGCTACTTTTGCCAGCACCACTTTGGCACCCCGTTTACATTTGGCAGCG

GCACCGAGCTGGAAATTAAATAA

Combined (SEQ ID NO: 37 and 38):
gatatccagatgacccagtccccgagctccctgtccgcctctgtgggcgatagggtcacc
 D   I   Q   M   T   Q   S   P   S   S   L   S   A   S   V   G   D   R   V   T atcacctgccgggcgagccaggatgtgaccaccgctgtagcctggtatcaacagaaacca
 I   T   C   R   A   S   Q   D   V   T   T   A   V   A   W   Y   Q   Q   K   P ggaaaagctccgaagcttctgatttactgggcgagccgtcttcataatggcgtgccgagc
 G   K   A   P   K   L   L   I   Y   W   A   S   R   L   H   N   G   V   P   S cgctttagcggcagcggctccgggacggatttcactctgaccatcagcagtctgcagccg
 R   F   S   G   S   G   S   G   T   D   F   T   L   T   I   S   S   L   Q   P gaagacttcgcaacttattactgtcagcaacattatagcaccccgctgacgttcggacag
 E   D   F   A   T   Y   Y   C   Q   Q   H   Y   S   T   P   L   T   F   G   Q ggtaccaaggtggagatcaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y
```

```
cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S gccggtagcgcaggcagcgcaggtagtggtggtagcgaagttcagctgcaggaaagtggc
 A   G   S   A   G   S   A   G   S   G   G   S   E   V   Q   L   Q   E   S   G ccggaactggaaatgccgggcgccagcgtgaaaatcagttgcaaagccagcggtagcagc
 P   E   L   E   M   P   G   A   S   V   K   I   S   C   K   A   S   G   S   S ttcacaggcttcagcatgaactgggtgaagcagagcaacggtaagagcctggagtggatc
 F   T   G   F   S   M   N   W   V   K   Q   S   N   G   K   S   L   E   W   I ggcaacattgacacctactatggcggcaccacctacaaccagaagttcaaaggcaaggcc
 G   N   I   D   T   Y   Y   G   G   T   T   Y   N   Q   K   F   K   G   K   A accctgaccgtggataaaagcagcagcacagcctacatgcagctgaaaagcctgaccagc
 T   L   T   V   D   K   S   S   S   T   A   Y   M   Q   L   K   S   L   T   S gaagatagcgccgtgtattactgcgcccgtagcgcctattacggcagcacctttgcatac
 E   D   S   A   V   Y   Y   C   A   R   S   A   Y   Y   G   S   T   F   A   Y tggcagggtaccctggtgaccgtgagcgcaggtggtggtggtagtggtggtggtggtagc
 W   Q   G   T   L   V   T   V   S   A   G   G   G   G   S   G   G   G   G   S ggtggtggcggtagtgacattcaaatgacccagagccctgcaagcctgagcgccagtgtt
 G   G   G   G   S   D   I   Q   M   T   Q   S   P   A   S   L   S   A   S   V ggcgaaaccgtgaccattacatgccgcgccagcgaaaacatctatagttacctggcctgg
 G   E   T   V   T   I   T   C   R   A   S   E   N   I   Y   S   Y   L   A   W taccagcagaaacagggcaaaagcccgcaactgctggtgtataacgccaaaaccctgatt
 Y   Q   Q   K   Q   G   K   S   P   Q   L   L   V   Y   N   A   K   T   L   I gagggcgtgccgagtcgcttcagcggtagcggtagcggtacacagttcagtctgaaaatc
 E   G   V   P   S   R   F   S   G   S   G   S   G   T   Q   F   S   L   K   I aacagcctgcagccggaagacttcggcagctacttttgccagcaccactttggcaccccg
 N   S   L   Q   P   E   D   F   G   S   Y   F   C   Q   H   H   F   G   T   P tttacatttggcagcggcaccgagctggaaattaaataa
 F   T   F   G   S   G   T   E   L   E   I   K   -
```

In an embodiment of any of the antibodies and/or scFv described herein (of the compositions described herein), the antibody and/or scFv is a neutralizing antibody/scFv with respect to the relevant *Ebola* virus.

In an embodiment, the antibody or scFv binds the relevant *Ebola* virus glycoprotein pre-fusion core, which is a heterohexamer of three copies of the GP1 and 3 copies of the GP2.

Exemplary Dual-Variable Domain (DVD) Bispecifics Sequences: the following exemplary DVD amino acid sequences (LC and HC) are provided, for the compositions of the invention as relating to the embodiments of antibodies E10, F4, KZ52, and 13C6 with non-limiting exemplary nucleotide sequences (in view of the degeneracy of the genetic code). The DVD constructs are dual-specific, tetravalent immunoglobulin G (IgG)-like molecules, termed dual-variable-domain immunoglobulin. In an embodiment, the sequences of the DVD except for the first and second linker amino acid sequences (such as the CDRs, the CH regions, the hinge regions, the CL region, sequences) are based on human IgG sequences).

E10-KZ52 HC DVD Fusion sequence - Amino Acid (SEQ ID NO: 43):

EVQLLESGGGLVKPGGSLRLSCAASGFTLINYRMNWVRQAPGKGLEWV

SSISSSSSYIHYADSVKGRFTISRDNAENSLYLQMNSLRAEDTAVYYCV

REGPRATGYSMADVFDIWGQGTMVTVSSASTKGPEVQLVESGGGLVQ

PGGSLRLSCAASGFAFNYYDIHWVRQAPGKGLEWVAYINPGGGNTYYA

DSVKGRFTISADTSKNTAYLQMNSLRAEDTAVYYCARQLYGNSFMDYW

GQGTLVTVSS

Underlined bold region is amino acid linker sequence.

Nucleotide (SEQ ID NO: 44):
GAAGTGCAGCTGCTGGAAAGCGGCGGTGGCCTGGTGAAACCGGGTG

GTAGTCTGCGCCTGAGTTGCGCCGCCAGCGGTTTTACCCTGATCAACTACCGCA

```
TGAACTGGGTGCGTCAGGCCCCGGGCAAAGGTCTGGAGTGGGTTAGTAGCATC

AGCAGTAGCAGCAGCTACATCCATTACGCCGACAGCGTGAAAGGCCGTTTCAC

CATCAGTCGCGATAACGCCGAGAATAGCCTGTACCTGCAGATGAACAGCCTGC

GTGCAGAAGATACCGCCGTGTATTACTGCGTGCGCGAAGGTCCGCGTGCAACC

GGTTATAGCATGGCCGATGTGTTCGATATTTGGGGCCAGGGTACCATGGTGACC

GTGAGCAGTGCCAGCACCAAAGGTCCGGAAGTTCAGCTGGTGGAAAGCGGTGG

TGGTCTGGTTCAGCCGGGTGGTAGCTTACGTCTGAGCTGCGCAGCCAGCGGCTT

TGCCTTCAATTATTATGATATTCATTGGGTTCGCCAAGCCCCGGGCAAGGGCCT

GGAATGGGTGGCATATATCAATCCGGGTGGCGGCAACACCTATTATGCCGATA

GCGTGAAGGGTCGCTTTACCATCAGCGCCGATACCAGCAAGAACACCGCCTATC

TGCAGATGAATAGCTTACGTGCTGAAGATACAGCCGTTTACTACTGTGCCCGCC

AGCTGTATGGCAACAGCTTCATGGATTATTGGGGCCAAGGCACCCTGGTGACCG

TTAGCAGC

Combined (SEQ ID NOS: 43 and 44):
gaagtgcagctgctggaaagcggcggtggcctggtgaaaccgggtggtagtctgcgcctg
E   V   Q   L   L   E   S   G   G   G   L   V   K   P   G   G   S   L   R   L agttgcgccgccagcggttttacccctgatcaactaccgcatgaactgggtgcgtcaggcc
S   C   A   A   S   G   F   T   L   I   N   Y   R   M   N   W   V   R   Q   A ccgggcaaaggtctggagtgggttagtagcatcagcagtagcagcagctacatccattac
P   G   K   G   L   E   W   V   S   S   I   S   S   S   S   S   Y   I   H   Y gccgacagcgtgaaaggccgtttcaccatcagtcgcgataacgccgagaatagcctgtac
A   D   S   V   K   G   R   F   T   I   S   R   D   N   A   E   N   S   L   Y ctgcagatgaacagcctgcgtgcagaagataccgccgtgtattactgcgtgcgcgaaggt
L   Q   M   N   S   L   R   A   E   D   T   A   V   Y   Y   C   V   R   E   G ccgcgtgcaaccggttatagcatggccgatgtgttcgatatttggggccagggtaccatg
P   R   A   T   G   Y   S   M   A   D   V   F   D   I   W   G   Q   G   T   M gtgaccgtgagcagtgccagcaccaaaggtccggaagttcagctggtggaaagcggtggt
V   T   V   S   S   A   S   T   K   G   P   E   V   Q   L   V   E   S   G   G ggtctggttcagccgggtggtagcttacgtctgagctgcgcagccagcggctttgccttc
G   L   V   Q   P   G   G   S   L   R   L   S   C   A   A   S   G   F   A   F aattattatgatattcattgggttcgccaagccccgggcaagggcctggaatgggtggca
N   Y   Y   D   I   H   W   V   R   Q   A   P   G   K   G   L   E   W   V   A tatatcaatccgggtggcggcaacacctattatgccgatagcgtgaagggtcgctttacc
Y   I   N   P   G   G   G   N   T   Y   Y   A   D   S   V   K   G   R   F   T atcagcgccgataccagcaagaacaccgcctatctgcagatgaatagcttacgtgctgaa
I   S   A   D   T   S   K   N   T   A   Y   L   Q   M   N   S   L   R   A   E gatacagccgtttactactgtgcccgccagctgtatggcaacagcttcatggattattgg
D   T   A   V   Y   Y   C   A   R   Q   L   Y   G   N   S   F   M   D   Y   W ggccaaggcaccctggtgaccgttagcagc
G   Q   G   T   L   V   T   V   S   S E10-KZ52 LC DVD Fusion sequence - Amino Acid (SEQ ID NO: 45):
ELVMTQSPDSLAVSLGERATINCKSSQSVLYSSNNKSYLAWYQQKPGQPPKLLIYW

ASTRESGVPDRFSGSGSGTDFTLTISSLQAEDVAVYYCQQYYSAPLTFGGGTKVEIK

TVAAPDIQMTQSPSSLSASVGDRVTITCRASQDVTTAVAWYQQKPGKAPKLLIYW

ASRLHNGVPSRFSGSGSGTDFTLTISSLQPEDFATYYCQQHYSTPLTFGQGTKVEIK
```

Underlined bold region is amino acid linker sequence.

```
Nucleotide (SEQ ID NO: 46):
GAACTGGTGATGACCCAGAGCCCGGATAGCCTGGCAGTTAGTCTGGG

CGAACGCGCCACCATTAACTGCAAAAGCAGCCAGAGCGTGCTGTATAGCAGCA

ATAATAAAAGCTATCTGGCATGGTACCAGCAGAAACCGGGTCAGCCGCCGAAG

CTGCTGATCTACTGGGCAAGCACCCGTGAAAGTGGTGTTCCGGATCGCTTTAGC

GGCAGCGGCAGCGGTACAGATTTCACCCTGACCATTAGCAGCCTGCAGGCCGA

AGATGTGGCAGTGTATTACTGCCAGCAGTACTATAGCGCACCGCTGACCTTTGG

TGGCGGCACCAAAGTGGAAATTAAGACCGTGGCCGCACCGGATATTCAGATGA

CCCAAAGCCCGAGCAGCCTGAGTGCAAGCGTGGGTGATCGTGTGACAATTACC

TGCCGCGCAAGCCAGGATGTGACCACCGCCGTGGCATGGTATCAACAGAAACC

GGGCAAAGCCCCGAAACTGCTGATTTATTGGGCCAGCCGCCTGCATAATGGCGT

TCCGAGCCGCTTCAGCGGTAGCGGTAGCGGTACCGACTTTACCCTGACCATTAG

CAGTCTGCAGCCGGAGGATTTTGCCACCTACTACTGTCAGCAGCACTATAGCAC

CCCTCTGACCTTTGGCCAGGGCACCAAGGTGGAAATCAAA

Combined (SEQ ID NO: 45 and 46):
gaactggtgatgacccagagcccggatagcctggcagttagtctgggcgaacgcgccacc
 E   L   V   M   T   Q   S   P   D   S   L   A   V   S   L   G   E   R   A   T attaactgcaaaagcagccagagcgtgctgtatagcagcaataataaaagctatctggca
 I   N   C   K   S   S   Q   S   V   L   Y   S   S   N   N   K   S   Y   L   A tggtaccagcagaaaccgggtcagccgccgaagctgctgatctactgggcaagcacccgt
 W   Y   Q   Q   K   P   G   Q   P   P   K   L   L   I   Y   W   A   S   T   R gaaagtggtgttccggatcgctttagcggcagcggcagcggtacagatttcaccctgacc
 E   S   G   V   P   D   R   F   S   G   S   G   S   G   T   D   F   T   L   T attagcagcctgcaggccgaagatgtggcagtgtattactgccagcagtactatagcgca
 I   S   S   L   Q   A   E   D   V   A   V   Y   Y   C   Q   Q   Y   Y   S   A ccgctgacctttggtggcggcaccaaagtggaaattaagaccgtggccgcaccggatatt
 P   L   T   F   G   G   G   T   K   V   E   I   K   T   V   A   A   P   D   I cagatgacccaaagcccgagcagcctgagtgcaagcgtgggtgatcgtgtgacaattacc
 Q   M   T   Q   S   P   S   S   L   S   A   S   V   G   D   R   V   T   I   T tgccgcgcaagccaggatgtgaccaccgccgtggcatggtatcaacagaaaccgggcaaa
 C   R   A   S   Q   D   V   T   T   A   V   A   W   Y   Q   Q   K   P   G   K gccccgaaactgctgatttattgggccagccgcctgcataatggcgttccgagccgcttc
 A   P   K   L   L   I   Y   W   A   S   R   L   H   N   G   V   P   S   R   F agcggtagcggtagcggtaccgactttaccctgaccattagcagtctgcagccggaggat
 S   G   S   G   S   G   T   D   F   T   L   T   I   S   S   L   Q   P   E   D tttgccacctactactgtcagcagcactatagcacccctctgacctttggccagggcacc
 F   A   T   Y   Y   C   Q   Q   H   Y   S   T   P   L   T   F   G   Q   G   T aaggtggaaatcaaa
 K   V   E   I   K F4-KZ52 HC DVD Fusion sequence - Amino Acid (SEQ ID NO: 47):
EVQLLESGGGLVKPGGSLRLSCAASGFTLINYRMNWVRQAPGKGLEWV

SSISSSSSYIHYADSVKGRFTISRDNAENSLYLQMNSLRAEDTAVYYCVREGPRATG

YSMADVFDIWGQGTMVTVSSASTKGPEVQLVESGGGLVQPGGSLRLSCAASGFAF

NYYDMFWVRQAPGKGLEWVAYIKPGGGNTYYADSVKGRFTISADTSKNTAYLQM

NSLRAEDTAVYYCARQLYGNSFFDYWGQGTLVTVSS
```

Underlined bold region is amino acid linker sequence.

```
Nucleotide (SEQ ID NO: 48):
GAGGTGCAGCTGCTGGAGAGCGGTGGTGGTCTGGTGAAACCGGGCG

GTAGCTTACGCCTGAGTTGCGCCGCAAGCGGTTTTACCCTGATCAACTACCGCA

TGAACTGGGTTCGTCAGGCCCCGGGCAAGGGTCTGGAATGGGTGAGCAGCATT

AGCAGCAGCAGCAGCTACATCCACTACGCCGATAGCGTGAAAGGTCGCTTCAC

CATCAGCCGCGACAATGCCGAAAACAGCCTGTATCTGCAGATGAACAGCTTAC

GCGCCGAAGATACCGCCGTGTACTATTGCGTTCGTGAGGGTCCGCGTGCAACCG

GCTATAGCATGGCCGACGTGTTCGATATCTGGGGTCAGGGCACCATGGTGACCG

TTAGCAGCGCCAGCACCAAAGGTCCGGAAGTGCAACTGGTGGAAAGTGGCGGT

GGTCTGGTGCAGCCGGGTGGTAGTCTGCGCCTGAGCTGTGCCGCAAGCGGCTTT

GCCTTTAATTATTATGATATGTTTTGGGTGCGCCAGGCACCGGGCAAAGGTCTG

GAGTGGGTGGCCTACATTAAGCCGGGCGGTGGCAATACCTATTATGCCGACAG

CGTGAAGGGCCGCTTTACCATCAGCGCCGACACCAGCAAAAACACCGCCTACC

TGCAAATGAATAGCTTACGTGCTGAAGACACCGCAGTTTATTATTGCGCCCGCC

AGCTGTATGGCAATAGCTTCTTCGACTATTGGGGCCAAGGCACCCTGGTGACAG

TTAGCAGC

Combined (SEQ ID NO: 47 and 48):
gaggtgcagctgctggagagcggtggtggtctggtgaaaccgggcggtagcttacgcctg
 E   V   Q   L   L   E   S   G   G   G   L   V   K   P   G   G   S   L   R   L agttgcgccgcaagcggttttaccctgatcaactaccgcatgaactgggttcgtcaggcc
 S   C   A   A   S   G   F   T   L   I   N   Y   R   M   N   W   V   R   Q   A ccgggcaagggtctggaatgggtgagcagcattagcagcagcagcagctacatccactac
 P   G   K   G   L   E   W   V   S   S   I   S   S   S   S   S   Y   I   H   Y gccgatagcgtgaaaggtcgcttcaccatcagccgcgacaatgccgaaaacagcctgtat
 A   D   S   V   K   G   R   F   T   I   S   R   D   N   A   E   N   S   L   Y ctgcagatgaacagcttacgcgccgaagataccgccgtgtactattgcgttcgtgagggt
 L   Q   M   N   S   L   R   A   E   D   T   A   V   Y   Y   C   V   R   E   G ccgcgtgcaaccggctatagcatggccgacgtgttcgatatctggggtcagggcaccatg
 P   R   A   T   G   Y   S   M   A   D   V   F   D   I   W   G   Q   G   T   M gtgaccgttagcagcgccagcaccaaaggtccggaagtgcaactggtggaaagtggcggt
 V   T   V   S   S   A   S   T   K   G   P   E   V   Q   L   V   E   S   G   G ggtctggtgcagccgggtggtagtctgcgcctgagctgtgccgcaagcggctttgccttt
 G   L   V   Q   P   G   G   S   L   R   L   S   C   A   A   S   G   F   A   F aattattatgatatgttttgggtgcgccaggcaccgggcaaaggtctggagtgggtggcc
 N   Y   Y   D   M   F   W   V   R   Q   A   P   G   K   G   L   E   W   V   A tacattaagccgggcggtggcaatacctattatgccgacagcgtgaagggccgctttacc
 Y   I   K   P   G   G   N   T   Y   Y   A   D   S   V   K   G   R   F   T atcagcgccgacaccagcaaaaacaccgcctacctgcaaatgaatagcttacgtgctgaa
 I   S   A   D   T   S   K   N   T   A   Y   L   Q   M   N   S   L   R   A   E gacaccgcagtttattattgcgcccgccagctgtatggcaatagcttcttcgactattgg
 D   T   A   V   Y   Y   C   A   R   Q   L   Y   G   N   S   F   F   F   D   Y   W ggccaaggcaccctggtgacagttagcagc
 G   Q   G   T   L   V   T   V   S   S F4-KZ52 LC DVD Fusion sequence - Amino Acid (SEQ ID NO: 49):
ELVMTQSPDSLAVSLGERATINCKSSQSVLYSSNNKSYLAWYQQKPGQP

PKLLIYWASTRESGVPDRFSGSGSGTDFTLTISSLQAEDVAVYYCQQYYSAPLTFGG

GTKVEIKTVAAPDIQMTQSPSSLSASVGDRVTITCKASQDVTTAVAWYQQKPGKAP
```

-continued

KLLIYWASTRHTGVPSRFSGSGSGTDFTLTISSLQPEDFATYYCQQHYSTPLTFGQGT

KVEIK

Underlined bold region is amino acid linker sequence.

Nucleotide (SEQ ID NO: 50):
GAACTGGTGATGACCCAGAGCCCGGATAGTCTGGCAGTTAGCCTGGG

CGAACGCGCCACCATTAACTGCAAAAGCAGCCAGAGCGTGCTGTACAGCAGCA

ACAACAAGAGCTACCTGGCCTGGTATCAGCAGAAACCGGGTCAGCCTCCGAAA

CTGCTGATTTACTGGGCAAGCACCCGTGAAAGTGGCGTGCCGGATCGCTTTAGC

GGCAGCGGTAGCGGTACCGATTTCACCCTGACAATCAGCAGCCTGCAGGCCGA

AGATGTTGCCGTGTACTACTGCCAGCAGTACTACAGCGCCCCGTTAACCTTCGG

CGGTGGCACCAAAGTGGAGATTAAAACCGTGGCCGCCCCGGATATTCAGATGA

CCCAAAGCCCGAGTAGCCTGAGCGCAAGCGTGGGTGATCGCGTGACCATTACC

TGCAAAGCCAGCCAGGACGTGACCACCGCAGTTGCCTGGTACCAGCAGAAGCC

GGGCAAAGCACCGAAGCTGCTGATTTATTGGGCAAGCACCCGCCATACCGGTG

TGCCTAGCCGTTTCAGCGGTAGTGGCAGTGGCACCGACTTTACCCTGACCATCA

GCAGTCTGCAGCCGGAAGACTTCGCCACCTACTATTGCCAACAGCACTACAGCA

CCCCGCTGACCTTTGGCCAGGGCACCAAGGTGGAAATTAAG

Combined (SEQ ID NO: 49 and 50):
gaactggtgatgacccagagcccggatagtctggcagttagcctgggcgaacgcgccacc
 E  L  V  M  T  Q  S  P  D  S  L  A  V  S  L  G  E  R  A  T attaactgcaaaagcagccagagcgtgctgtacagcagcaacaacaagagctacctggcc
 I  N  C  K  S  S  Q  S  V  L  Y  S  S  N  N  K  S  Y  L  A tggtatcagcagaaaccgggtcagcctccgaaactgctgatttactgggcaagcacccgt
 W  Y  Q  Q  K  P  G  Q  P  P  K  L  L  I  Y  W  A  S  T  R gaaagtggcgtgccggatcgctttagcggcagcggtagcggtaccgatttcaccctgaca
 E  S  G  V  P  D  R  F  S  G  S  G  S  G  T  D  F  T  L  T atcagcagcctgcaggccgaagatgttgccgtgtactactgccagcagtactacagcgcc
 I  S  S  L  Q  A  E  D  V  A  V  Y  Y  C  Q  Q  Y  Y  S  A ccgttaaccttcggcggtggcaccaaagtggagattaaaaccgtggccgccccggatatt
 P  L  T  F  G  G  G  T  K  V  E  I  K  T  V  A  A  P  D  I cagatgacccaaagcccgagtagcctgagcgcaagcgtgggtgatcgcgtgaccattacc
 Q  M  T  Q  S  P  S  S  L  S  A  S  V  G  D  R  V  T  I  T tgcaaagccagccaggacgtgaccaccgcagttgcctggtaccagcagaagccgggcaaa
 C  K  A  S  Q  D  V  T  T  A  V  A  W  Y  Q  Q  K  P  G  K gcaccgaagctgctgatttattgggcaagcacccgccataccggtgtgcctagccgtttc
 A  P  K  L  L  I  Y  W  A  S  T  R  H  T  G  V  P  S  R  F agcggtagtggcagtggcaccgactttaccctgaccatcagcagtctgcagccggaagac
 S  G  S  G  S  G  T  D  F  T  L  T  I  S  S  L  Q  P  E  D ttcgccacctactattgccaacagcactacagcaccccgctgacctttggccagggcacc
 F  A  T  Y  Y  C  Q  Q  H  Y  S  T  P  L  T  F  G  Q  G  T aaggtggaaattaag
 K  V  E  I  K E10-13C6 HC DVD Fusion sequence - Amino Acid (SEQ ID NO: 51):
MGRLTSSFLLLIVPAYVLSQLTLKESGPGILKPSQTLSLTCSLSGFSLSTSG

VGVGWFRQPSGKGLEWLALIWWDDDKYYNPSLKSQLSISKDFSRNQVFLKISNVDI

ADTATYYCARRDPFGYDNAMGYWGQGTSVTVSSASTKGPEVQLVESGGGLVQPG

GSLRLSCAASGFAFNYYDIHWVRQAPGKGLEWVAYINPGGGNTYYADSVKGRFTI

SADTSKNTAYLQMNSLRAEDTAVYYCARQLYGNSFMDYWGQGTLVTVSS

Underlined bold region is amino acid linker sequence.

```
Nucleotide (SEQ ID NO: 52):
ATGGGTCGCCTGACCAGTAGCTTTCTGCTGCTGATTGTGCCTGCCTAT

GTGTTAAGCCAGCTGACCCTGAAGGAGAGCGGCCCGGGTATTCTGAAACCTAG

CCAGACCCTGAGCCTGACCTGCAGCCTGAGCGGTTTTAGCCTGAGTACCAGCGG

TGTGGGCGTTGGTTGGTTCCGCCAGCCGAGCGGTAAAGGTCTGGAATGGCTGGC

CCTGATTTGGTGGGATGATGATAAATACTACAACCCGAGCCTGAAAAGCCAGCT

GAGCATTAGCAAAGATTTTAGCCGCAATCAGGTTTTCCTGAAAATCAGCAACGT

GGACATTGCCGACACCGCCACCTACTATTGCGCCCGCCGCGACCCGTTTGGCTA

TGATAACGCCATGGGCTACTGGGGCCAGGGTACCAGCGTTACCGTTAGCAGCG

CCAGCACCAAAGGCCCGGAAGTGCAGCTGGTTGAAAGCGGTGGTGGTCTGGTT

CAGCCGGGTGGTAGTCTGCGTCTGAGTTGCGCCGCCAGCGGCTTTGCCTTCAAT

TATTATGATATCCATTGGGTTCGCCAGGCACCGGGTAAGGGCCTGGAATGGGTG

GCATACATTAATCCGGGTGGCGGTAACACCTACTATGCCGACAGCGTGAAAGG

TCGCTTCACCATCAGCGCCGATACCAGCAAGAACACCGCCTATCTGCAGATGAA

CAGCCTGCGTGCCGAAGATACCGCCGTGTATTATTGTGCCCGCCAGCTGTATGG

CAACAGCTTCATGGATTATTGGGGCCAAGGCACCCTGGTTACCGTTAGCAGC
```

```
Combined (SEQ ID NOS: 51 and 52):
atgggtcgcctgaccagtagctttctgctgctgattgtgcctgcctatgtgttaagccag
 M   G   R   L   T   S   S   F   L   L   L   I   V   P   A   Y   V   L   S   Q ctgaccctgaaggagagcggcccgggtattctgaaacctagccagaccctgagcctgacc
 L   T   L   K   E   S   G   P   G   I   L   K   P   S   Q   T   L   S   L   T tgcagcctgagcggttttagcctgagtaccagcggtgtgggcgttggttggttccgccag
 C   S   L   S   G   F   S   L   S   T   S   G   V   G   V   G   W   F   R   Q ccgagcggtaaaggtctggaatggctggccctgatttggtgggatgatgataaatactac
 P   S   G   K   G   L   E   W   L   A   L   I   W   W   D   D   D   K   Y   Y aacccgagcctgaaaagccagctgagcattagcaaagattttagccgcaatcaggttttc
 N   P   S   L   K   S   Q   L   S   I   S   K   D   F   S   R   N   Q   V   F ctgaaaatcagcaacgtggacattgccgacaccgccacctactattgcgcccgccgcgac
 L   K   I   S   N   V   D   I   A   D   T   A   T   Y   Y   C   A   R   R   D ccgtttggctatgataacgccatgggctactggggccagggtaccagcgttaccgttagc
 P   F   G   Y   D   N   A   M   G   Y   W   G   Q   G   T   S   V   T   V   S agcgccagcaccaaaggcccggaagtgcagctggttgaaagcggtggtggtctggttcag
 S   A   S   T   K   G   P   E   V   Q   L   V   E   S   G   G   G   L   V   Q ccgggtggtagtctgcgtctgagttgcgccgccagcggctttgccttcaattattatgat
 P   G   G   S   L   R   L   S   C   A   A   S   G   F   A   F   N   Y   Y   D atccattgggttcgccaggcaccgggtaagggcctggaatgggtggcatacattaatccg
 I   H   W   V   R   Q   A   P   G   K   G   L   E   W   V   A   Y   I   N   P ggtggcggtaacacctactatgccgacagcgtgaaaggtcgcttcaccatcagcgccgat
 G   G   G   N   T   Y   Y   A   D   S   V   K   G   R   F   T   I   S   A   D accagcaagaacaccgcctatctgcagatgaacagcctgcgtgccgaagataccgccgtg
 T   S   K   N   T   A   Y   L   Q   M   N   S   L   R   A   E   D   T   A   V tattattgtgcccgccagctgtatggcaacagcttcatggattattggggccaaggcacc
 Y   Y   C   A   R   Q   L   Y   G   N   S   F   M   D   Y   W   G   Q   G   T
```

```
ctggttaccgttagcagc
 L   V   T   V   S   S

E10-13C6 LC DVD Fusion sequence - Amino Acid (SEQ ID NO: 53):
MGIKMKSQTQAFVFAFLWLSGVDGDIVMTQSQKFMSTSVGDRVSLTCK

ASQNVGTAVAWYQQKPGQSPKLLIYSASNRYTGVPDRFTGSGSGTDFTLTISNMQS

EDLADYFCQQYSSYPLTFGAGTKLELRRTVAAPDIQMTQSPSSLSASVGDRVTITCR

ASQDVTTAVAWYQQKPGKAPKLLIYWASRLHNGVPSRFSGSGSGTDFTLTISSLQP

EDFATYYCQQHYSTPLTFGQGTKVEIK
```

Underlined bold region is amino acid linker sequence.

```
Nucleotide (SEQ ID NO: 54):
ATGGGCATCAAAATGAAGAGCCAGACCCAGGCCTTTGTGTTTGCCTT

TCTGTGGCTGAGTGGCGTGGATGGCGATATCGTGATGACCCAGAGCCAAAAGTT

CATGAGCACCAGCGTGGGCGATCGCGTGAGCCTGACCTGCAAAGCCAGCCAGA

ACGTGGGCACCGCAGTGGCATGGTACCAGCAGAAACCGGGCCAGAGCCCGAAA

CTGCTGATCTACAGCGCAAGCAATCGCTATACCGGTGTTCCGGATCGCTTTACA

GGCAGCGGCAGCGGCACCGACTTTACCCTGACCATTAGCAACATGCAGAGCGA

AGACCTGGCCGACTATTTTTGCCAGCAGTACAGCAGCTATCCGCTGACCTTTGG

CGCCGGCACCAAATTAGAACTGCGCCGTACCGTTGCCGCCCCGGATATTCAGAT

GACCCAAAGCCCGAGTAGCCTGAGCGCAAGCGTGGGCGACCGTGTGACCATTA

CCTGTCGCGCCAGCCAGGACGTTACCACCGCAGTTGCCTGGTATCAGCAAAAAC

CGGGCAAAGCCCCGAAGCTGCTGATCTATTGGGCAAGTCGTCTGCATAACGGC

GTTCCGAGCCGCTTTAGCGGCAGTGGTAGCGGCACCGATTTCACCCTGACCATC

AGCAGCCTGCAGCCGGAGGATTTTGCCACCTACTACTGTCAGCAGCACTACAGC

ACACCGCTGACCTTCGGCCAGGGCACCAAGGTGGAAATTAAA

Combined (SEQ ID NOS: 53 and 54):
atgggcatcaaaatgaagagccagacccaggcctttgtgtttgcctttctgtggctgagt
 M   G   I   K   M   K   S   Q   T   Q   A   F   V   F   A   F   L   W   L   S ggcgtggatggcgatatcgtgatgacccagagccaaaagttcatgagcaccagcgtgggc
 G   V   D   G   D   I   V   M   T   Q   S   Q   K   F   M   S   T   S   V   G gatcgcgtgagcctgacctgcaaagccagccagaacgtgggcaccgcagtggcatggtac
 D   R   V   S   L   T   C   K   A   S   Q   N   V   G   T   A   V   A   W   Y cagcagaaaccgggccagagcccgaaactgctgatctacagcgcaagcaatcgctatacc
 Q   Q   K   P   G   Q   S   P   K   L   L   I   Y   S   A   S   N   R   Y   T ggtgttccggatcgctttacaggcagcggcagcggcaccgactttacccctgaccattagc
 G   V   P   D   R   F   T   G   S   G   S   G   T   D   F   T   L   T   I   S aacatgcagagcgaagacctggccgactattttttgccagcagtacagcagctatccgctg
 N   M   Q   S   E   D   L   A   D   Y   F   C   Q   Q   Y   S   S   Y   P   L acctttggcgccggcaccaaattagaactgcgccgtaccgttgccgccccggatattcag
 T   F   G   A   G   T   K   L   E   L   R   R   T   V   A   A   P   D   I   Q atgacccaaagcccgagtagcctgagcgcaagcgtgggcgaccgtgtgaccattacctgt
 M   T   Q   S   P   S   S   L   S   A   S   V   G   D   R   V   T   I   T   C cgcgccagccaggacgttaccaccgcagttgcctggtatcagcaaaaaccgggcaaagcc
 R   A   S   Q   D   V   T   T   A   V   A   W   Y   Q   Q   K   P   G   K   A ccgaagctgctgatctattgggcaagtcgtctgcataacggcgttccgagccgctttagc
 P   K   L   L   I   Y   W   A   S   R   L   H   N   G   V   P   S   R   F   S ggcagtggtagcggcaccgatttcaccctgaccatcagcagcctgcagccggaggatttt
 G   S   G   S   G   T   D   F   T   L   T   I   S   S   L   Q   P   E   D   F
```

-continued

```
gccacctactactgtcagcagcactacagcacaccgctgaccttcggccagggcaccaag
 A  T  Y  Y  C  Q  Q  H  Y  S  T  P  L  T  F  G  Q  G  T  K gtggaaattaaa
 V  E  I  K
```

```
F4-13C6 HC DVD Fusion sequence - Amino Acid (SEQ ID NO: 55):
MGRLTSSFLLLIVPAYVLSQLTLKESGPGILKPSQTLSLTCSLSGFSLSTSG

VGVGWFRQPSGKGLEWLALIWWDDDKYYNPSLKSQLSISKDFSRNQVFLKISNVDI

ADTATYYCARRDPFGYDNAMGYWGQGTSVTVSSASTKGPEVQLVESGGGLVQPG

GSLRLSCAASGFAFNYYDMFWVRQAPGKGLEWVAYIKPGGGNTYYADSVKGRFTI

SADTSKNTAYLQMNSLRAEDTAVYYCARQLYGNSFFDYWGQGTLVTVSS
```

Underlined bold region is amino acid linker sequence.

```
Nucleotide (SEQ ID NO: 56):
ATGGGTCGCCTGACCAGTAGCTTTCTGCTGCTGATTGTGCCTGCCTAT

GTGTTAAGCCAGCTGACCCTGAAGGAGAGCGGCCCGGGTATTCTGAAACCTAG

CCAGACCCTGAGCCTGACCTGCAGCCTGAGCGGTTTTAGCCTGAGTACCAGCGG

TGTGGGCGTTGGTTGGTTCCGCCAGCCGAGCGGTAAAGGTCTGGAATGGCTGGC

CCTGATTTGGTGGGATGATGATAAATACTACAACCCGAGCCTGAAAAGCCAGCT

GAGCATTAGCAAAGATTTTAGCCGCAATCAGGTTTTCCTGAAAATCAGCAACGT

GGACATTGCCGACACCGCCACCTACTATTGCGCCCGCCGCGACCCGTTTGGCTA

TGATAACGCCATGGGCTACTGGGGCCAGGGTACCAGCGTTACCGTTAGCAGCG

CCAGCACCAAAGGCCCGGAAGTGCAGCTGGTTGAAAGCGGTGGTGGTCTGGTT

CAGCCGGGTGGTAGTCTGCGTCTGAGTTGCGCCGCCAGCGGCTTTGCCTTCAAT

TATTATGATATGTTTTGGGTTCGCCAGGCACCGGGTAAGGGCCTGGAATGGGTG

GCATACATTAAACCGGGTGGCGGTAACACCTACTATGCCGACAGCGTGAAAGG

TCGCTTCACCATCAGCGCCGATACCAGCAAGAACACCGCCTATCTGCAGATGAA

CAGCCTGCGTGCCGAAGATACCGCCGTGTATTATTGTGCCCGCCAGCTGTATGG

CAACAGCTTCTTTGATTATTGGGGCCAAGGCACCCTGGTTACCGTTAGCAGC
```

```
Combined (SEQ ID NOS: 55 and 56):
atgggtcgcctgaccagtagctttctgctgctgattgtgcctgcctatgtgttaagccag
 M  G  R  L  T  S  S  F  L  L  L  I  V  P  A  Y  V  L  S  Q ctgaccctgaaggagagcggcccgggtattctgaaacctagccagaccctgagcctgacc
 L  T  L  K  E  S  G  P  G  I  L  K  P  S  Q  T  L  S  L  T tgcagcctgagcggttttagcctgagtaccagcggtgtgggcgttggttggttccgccag
 C  S  L  S  G  F  S  L  S  T  S  G  V  G  V  G  W  F  R  Q ccgagcggtaaaggtctggaatggctggccctgatttggtgggatgatgataaatactac
 P  S  G  K  G  L  E  W  L  A  L  I  W  W  D  D  D  K  Y  Y aacccgagcctgaaaagccagctgagcattagcaaagattttagccgcaatcaggttttc
 N  P  S  L  K  S  Q  L  S  I  S  K  D  F  S  R  N  Q  V  F ctgaaaatcagcaacgtggacattgccgacaccgccacctactattgcgcccgccgcgac
 L  K  I  S  N  V  D  I  A  D  T  A  T  Y  Y  C  A  R  R  D ccgtttggctatgataacgccatgggctactggggccagggtaccagcgttaccgttagc
 P  F  G  Y  D  N  A  M  G  Y  W  G  Q  G  T  S  V  T  V  S agcgccagcaccaaaggcccggaagtgcagctggttgaaagcggtggtggtctggttcag
 S  A  S  T  K  G  P  E  V  Q  L  V  E  S  G  G  G  L  V  Q ccgggtggtagtctgcgtctgagttgcgccgccagcggctttgccttcaattattatgat
 P  G  G  S  L  R  L  S  C  A  A  S  G  F  A  F  N  Y  Y  D
```

```
-continued
atgttttgggttcgccaggcaccgggtaagggcctggaatgggtggcatacattaaaccg
 M  F  W  V  R  Q  A  P  G  K  G  L  E  W  V  A  Y  I  K  P ggtggcggtaacacctactatgccgacagcgtgaaaggtcgcttcaccatcagcgccgat
 G  G  G  N  T  Y  Y  A  D  S  V  K  G  R  F  T  I  S  A  D accagcaagaacaccgcctatctgcagatgaacagcctgcgtgccgaagataccgccgtg
 T  S  K  N  T  A  Y  L  Q  M  N  S  L  R  A  E  D  T  A  V tattattgtgcccgccagctgtatggcaacagcttctttgattattggggccaaggcacc
 Y  Y  C  A  R  Q  L  Y  G  N  S  F  F  D  Y  W  G  Q  G  T ctggttaccgttagcagc
 L  V  T  V  S  S F4-13C6 LC DVD Fusion sequence - Amino Acid (SEQ ID NO: 57):
MGIKMKSQTQAFVFAFLWLSGVDGDIVMTQSQKFMSTSVGDRVSLTCK

ASQNVGTAVAWYQQKPGQSPKLLIYSASNRYTGVPDRFTGSGSGTDFTLTISNMQS

EDLADYFCQQYSSYPLTFGAGTKLELRRTVAAPDIQMTQSPSSLSASVGDRVTITCK

ASQDVTTAVAWYQQKPGKAPKLLIYWASTRHTGVPSRFSGSGSGTDFTLTISSLQP

EDFATYYCQQHYSTPLTFGQGTKVEIK
```

Underlined bold region is amino acid linker sequence.

```
Nucleotide (SEQ ID NO: 58):
ATGGGCATCAAAATGAAGAGCCAGACCCAGGCCTTTGTGTTTGCCTT

TCTGTGGCTGAGTGGCGTGGATGGCGATATCGTGATGACCCAGAGCCAAAAGTT

CATGAGCACCAGCGTGGGCGATCGCGTGAGCCTGACCTGCAAAGCCAGCCAGA

ACGTGGGCACCGCAGTGGCATGGTACCAGCAGAAACCGGGCCAGAGCCCGAAA

CTGCTGATCTACAGCGCAAGCAATCGCTATACCGGTGTTCCGGATCGCTTTACA

GGCAGCGGCAGCGGCACCGACTTTACCCTGACCATTAGCAACATGCAGAGCGA

AGACCTGGCCGACTATTTTTGCCAGCAGTACAGCAGCTATCCGCTGACCTTTGG

CGCCGGCACCAAATTAGAACTGCGCCGTACCGTTGCCGCCCCGGATATTCAGAT

GACCCAAAGCCCGAGTAGCCTGAGCGCAAGCGTGGGCGACCGTGTGACCATTA

CCTGTAAAGCCAGCCAGGACGTTACCACCGCAGTTGCCTGGTATCAGCAAAAA

CCGGGCAAAGCCCCGAAGCTGCTGATCTATTGGGCAAGTACCCGTCATACCGGC

GTTCCGAGCCGCTTTAGCGGCAGTGGTAGCGGCACCGATTTCACCCTGACCATC

AGCAGCCTGCAGCCGGAGGATTTTGCCACCTACTACTGTCAGCAGCACTACAGC

ACACCGCTGACCTTCGGCCAGGGCACCAAGGTGGAAATTAAA
Combined (SEQ ID NO: 57 and 58):
atgggcatcaaaatgaagagccagacccaggcctttgtgtttgcctttctgtggctgagt
 M  G  I  K  M  K  S  Q  T  Q  A  F  V  F  A  F  L  W  L  S ggcgtggatggcgatatcgtgatgacccagagccaaaagttcatgagcaccagcgtgggc
 G  V  D  G  D  I  V  M  T  Q  S  Q  K  F  M  S  T  S  V  G gatcgcgtgagcctgacctgcaaagccagccagaacgtgggcaccgcagtggcatggtac
 D  R  V  S  L  T  C  K  A  S  Q  N  V  G  T  A  V  A  W  Y cagcagaaaccgggccagagcccgaaactgctgatctacagcgcaagcaatcgctatacc
 Q  Q  K  P  G  Q  S  P  K  L  L  I  Y  S  A  S  N  R  Y  T ggtgttccggatcgctttacaggcagcggcagcggcaccgactttaccctgaccattagc
 G  V  P  D  R  F  T  G  S  G  S  G  T  D  F  T  L  T  I  S aacatgcagagcgaagacctggccgactattttgccagcagtacagcagctatccgctg
 N  M  Q  S  E  D  L  A  D  Y  F  C  Q  Q  Y  S  S  Y  P  L acctttggcgccggcaccaaattagaactgcgccgtaccgttgccgccccggatattcag
 T  F  G  A  G  T  K  L  E  L  R  R  T  V  A  A  P  D  I  Q
```

```
                      -continued
atgacccaaagcccgagtagcctgagcgcaagcgtgggcgaccgtgtgaccattacctgt
 M   T   Q   S   P   S   S   L   S   A   S   V   G   D   R   V   T   I   T   C aaagccagccaggacgttaccaccgcagttgcctggtatcagcaaaaaccgggcaaagcc
 K   A   S   Q   D   V   T   T   A   V   A   W   Y   Q   Q   K   P   G   K   A ccgaagctgctgatctattgggcaagtacccgtcataccggcgttccgagccgctttagc
 P   K   L   L   I   Y   W   A   S   T   R   H   T   G   V   P   S   R   F   S ggcagtggtagcggcaccgatttcaccctgaccatcagcagcctgcagccggaggatttt
 G   S   G   S   G   T   D   F   T   L   T   I   S   S   L   Q   P   E   D   F gccacctactactgtcagcagcactacagcacaccgctgaccttcggccagggcaccaag
 A   T   Y   Y   C   Q   Q   H   Y   S   T   P   L   T   F   G   Q   G   T   K gtggaaattaaa
 V   E   I   K
```

In an embodiment of any of the antibodies and/or scFv described herein (of the compositions described herein), the antibody and/or scFv is a neutralizing antibody/scFv with respect to the relevant *Ebola* virus.

In an embodiment, the antibody or scFv binds the relevant *Ebola* virus glycoprotein pre-fusion core, which is a heterohexamer of three copies of the GP1 and 3 copies of the GP2.

In an embodiment, the antibody comprises an Fc region having a sequence identical to a human Fc region.

In an embodiment, the Fc region of the antibody is glycosylated.

A "humanized" antibody as used herein, unless otherwise indicated, is a chimeric antibody that contains minimal sequence (CDRs) derived from non-human immunoglobulin (e.g. such as a mouse immunoglobulin). In one embodiment, a humanized antibody is an antibody having a sequence of a human immunoglobulin (recipient antibody) in which CDR residues of a hypervariable region (HVR) of the recipient are replaced by CDR residues from a non-human species (donor antibody) such as a mouse having the desired specificity. In some instances, FR residues of the human immunoglobulin variable domain are replaced by corresponding non-human residues, for example by a back-mutation. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. Other techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. The framework regions of the antibodies of the invention having a sequence identical to a human framework region may include amino acid residues not encoded by human germline sequences (e.g., mutations introduced by random or site-specific mutagenesis). In an embodiment, the isolated antibody or antigen-binding antibody fragment comprises a variable domain framework sequence having a sequence identical to a human variable domain framework sequence FR1, FR2, FR3 or FR4. In an embodiment, the isolated antibody or antigen-binding antibody fragment comprises a variable domain framework sequence having a sequence identical to at least two of human variable domain framework sequences FR1, FR2, FR3 or FR4. In an embodiment, the isolated antibody or antigen-binding antibody fragment comprises a variable domain framework sequence having a sequence identical to at least three of human variable domain framework sequences FR1, FR2, FR3 or FR4. In an embodiment, the isolated antibody or antigen-binding antibody fragment comprises a variable domain framework sequence having a sequence identical to all four of human variable domain framework sequences FR1, FR2, FR3 and FR4.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

In an embodiment, the antibodies of the invention described herein comprise a human Fc region or a variant human Fc region. A variant human Fc region comprises an amino acid sequence which differs from that of a native sequence Fc region by virtue of at least one amino acid modification, yet retains at least one effector function of the native sequence human Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

In an embodiment, the scFv is a variable domain light chain (VL) and a variable domain heavy chain (VH) which are linked N—C or C—N, respectively, via a peptide linker. In an embodiment the linker of the scFv is 5-30 amino acids in length. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988), each of which are hereby incorporated by reference in their entirety.

In an embodiment, the antibody and or scFv(s) of the composition of the invention do not recognize an *Ebola* GP1 mucin-like domain. In an embodiment, the antibody and or scFv(s) of the composition of the invention do not recognize an *Ebola* GP1 variable glycan cap.

For trispecific constructs, which target three different Filovirus strains and/or species, an IgG directed at the prefusion glycoprotein core for one strain is fused two different scFvs (each directed at a prefusion glycoprotein core for two other strains, respectively). The scFvs are fused to the IgG at two different positions, with the two scFv having specificity for the different viruses. In a non-limiting example, an SUDV-specific IgG with EBOV-specific scFv as light chain N-terminal fusion and a MARV-specific scFv as a heavy chain C-terminal fusion.

The phrase "and/or" as used herein, with option A and/or option B for example, encompasses the embodiments of (i) option A, (ii) option B, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

*Ebola* virus pathogenesis and cell entry: The infectious agents *Ebola* virus and *Marburg* virus (MARV) are the two major species of the Filoviridae family of enveloped negative-sense RNA viruses (1-4). Based on nucleotide sequence and outbreak location, isolates of *Ebola* virus are classified into five species: *Zaire* (EBOV), *Tai Forest* (TAFV), *Sudan* (SUDV), *Reston* (RESTV), and *Bundibugyo* (BDBV). There are two MARV variants (*Marburg* and *Ravn*). Severe human disease and deaths (30-90% case fatality rates in large outbreaks) are associated with EBOV, SUDV, BDBV, and MARV (2). Although the ecology of these agents remains incompletely understood, several species of African fruit bats appear to be reservoirs for *Ebola* virus and MARV (5). EBOV and SUDV are the most pathogenic among the ebolaviruses, and both have been associated with recurring outbreaks (6). Among the 13 documented EBOV outbreaks and the six SUDV outbreaks from 1976-2012, the average human case fatality rates are 70% and 52%, respectively. Together, EBOV and SUDV account for over 95% of *Ebola* virus-related deaths (6); these statistics do not include the ongoing EBOV outbreak in West Africa that is of unprecedented scope and geographic distribution. Therefore, a therapeutic agent that is effective against both EBOV and SUDV would greatly reduce the threat of an *Ebola* virus pandemic.

All human outbreaks occur as a result of direct contact with infected wildlife, with subsequent person-to-person transmission, mostly through the mucosa or contaminated needles. Uncontrolled viral replication is central to filovirus-induced disease, both because it is cytopathic and because it induces dysregulation of the host immune system (2, 7, 8). Therefore, antiviral therapies that reduce viral load are expected to increase patient survival, in part, by allowing time to mount an effective immune response. While many cell types can be infected with filovirus in vitro and in vivo, antigen-presenting cells (macrophages and dendritic cells) appear to be early and sustained targets of infection in vivo. Infected macrophages are unable to stimulate a robust immune response, and cause a "cytokine storm" that is proposed to be the primary cause of the blood clotting abnormalities and vascular leakage characteristic of filovirus hemorrhagic fever (9). Damage to other tissues (e.g., liver, kidneys, vascular endothelia) is thought to contribute to the above and to late-stage multi-organ failure. Death typically occurs 8-15 days after infection (10). Because of their high mortality rate, rapid proliferation, and potential for aerosolization, *Ebola* virus and *Marburg* virus are classified as Category A biodefense pathogens. There are currently no FDA-approved treatments for these infections.

The filovirus genome is a ~19 kb single-strand negative-sense RNA genome that encodes seven genes arranged in a linear fashion (1-4). In mature viral particles and infected cells, the genome is intimately associated with four viral proteins: the nucleocapsid protein NP, the polymerase L, the polymerase accessory protein VP35, and the transcriptional activator protein VP30. This nucleocapsid structure is in turn encapsidated in a viral matrix, comprising proteins VP40 and VP24. The host-derived viral membrane bilayer surrounds, and is peripherally associated with, the matrix. Embedded in the viral membrane are trimers of the viral glycoprotein, GP, which mediates the first step in infection: delivery of the viral nucleocapsid "payload" into the cytoplasm of the host cell. GP is the target of virus-directed antibodies that neutralize extracellular filovirus particles (4, 11-14).

Figures 1A, 1B:
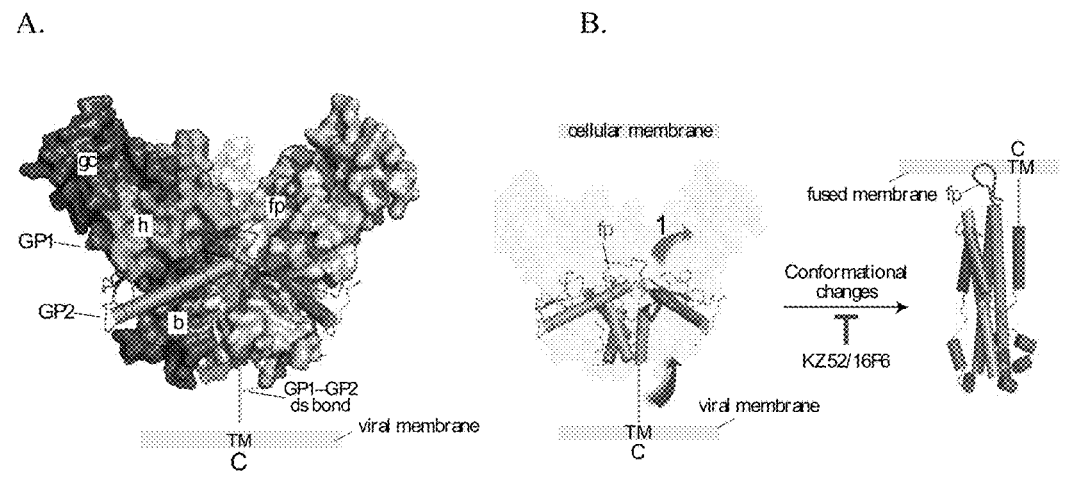

The mature filovirus GP spike is a trimer of three disulfide-linked GP1-GP2 heterodimers, generated by endoproteolytic cleavage of the GP0 precursor polypeptide by furin during virus assembly (4, 13-15). GP1 mediates viral adhesion to host cells and regulates the activity of the transmembrane subunit GP2, which mediates fusion of viral and cellular membranes during cell entry. The prefusion GP1-GP2 spike has a "chalice-and-bowl" morphology—the three GP2 subunits form the chalice within which the bowl, comprised of the three GP1 subunits, rests (FIG. 1A) (13-15). This trimeric assembly is stabilized mainly by GP1-GP2 and GP2-GP2 contacts. The GP1 subunit is organized into three subdomains. The base ('b', light blue) interacts extensively with GP2 and clamps it in its prefusion conformation.

The head ('h', green) contains a putative receptor-binding sequence. Together with GP2, the base and head subdomains of GP1 form the conserved structural core of the GP1-GP2 spike. In contrast to the GP1-GP2 core, the most external subdomains of GP1—the glycan cap ('gc', dark blue) and the mucin-like domain (not shown)—are extensively glycosylated and display a high degree of sequence variation among filovirus isolates. Therefore, antibodies with broadly cross-neutralizing activity must recognize the conserved GP1-GP2 core and not the variable glycan cap or mucin-like domain. In response to a fusion trigger within host cell endosomes, GP2 disengages from GP1 and undergoes a series of large-scale conformational changes that drive coalescence of viral and cellular membrane bilayers (FIG. 1B) (4, 16-19). The result of viral membrane fusion is cytoplasmic release of the viral nucleocapsid. KZ52 and 16F6 likely function by inhibiting these fusion-associated conformational changes (4, 13, 14).

Figure 2:
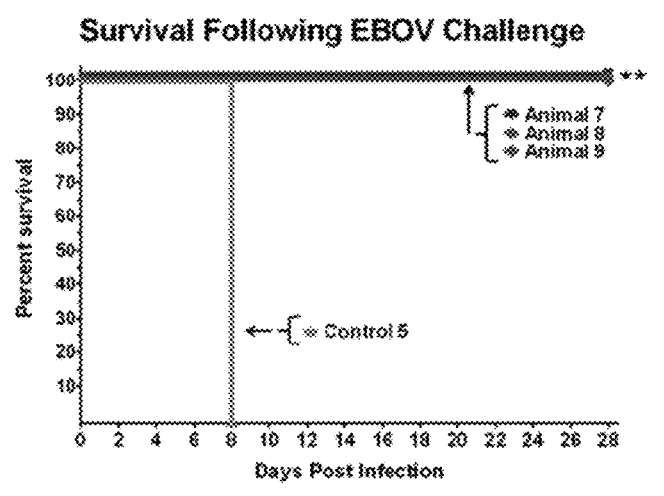

Immunotherapy is a tractable approach to filovirus treatment pre- and post-exposure. Until recently, it has been unclear if passive immunotherapy would be effective for treatment or prophylaxis of filovirus infection (20). However, recent studies using non-human primate (NHP) models have provided convincing evidence that immunotherapy can and should be pursued (21, 22). Dr. Dye's laboratory reported that rhesus macaques can be protected up to 48 hours post-exposure from EBOV or MARV infection by passive transfer of fractionated EBOV- or MARV-specific IgG isolated from convalescent animals (same species) (21). In this study, two of the three NHPs that were challenged with EBOV, and then administered serum IgG, had no clinical signs of illness; the third developed mild, delayed signs of the disease but fully recovered (FIG. 2). The control animal died eight days post exposure, as is typical for untreated infection. Similar results were obtained with MARV-challenged animals, suggesting that filovirus infection in general can be treated with antibodies. This protection required only three total administrations of the serum IgG (48 hours post exposure, then again at four and eight days). Therefore, antibody-based filovirus therapy is feasible, protective, and can be administered post-exposure. In 2012, three groups (Kobinger, Zeitlin/Olinger and Takada/Feldmann) independently reported that cocktails of mAbs could protect NHPs against EBOV challenge (22-24). The Kobinger study involved a cocktail of three GP-specific murine monoclonal antibodies (mAbs) that were administered at intervals of 3 days beginning 24 or 48 hours post-exposure. Initiation of the treatment at 24 hours conferred complete survival (4/4 macaques) and initiation of treatment 48 hours post-exposure conferred partial protection (2/4 macaques fully recovered) (22). The Olinger/Zeitlin study demonstrated that a cocktail of three mouse/human chimeric mAbs (known as 'MB-003') produced in whole plant cells provided full protection when administered 1 hour post-exposure, and partial protection when administered 24 or 48 hours post-exposure (23). The Takada/Feldmann study demonstrated that a combination of two human-mouse chimeric mAbs could partially protect NHPs against EBOV challenge (24). Three NHPs were administered a cocktail of the two mAbs 24 hours preceding challenge with EBOV, then again 24- and 48-hours post-exposure. One of the three animals survived, one had delayed onset of hemorrhagic fever and was ultimately euthanized, and the other was similar to the control. It was concluded that the protection could be improved if serum half-life of the mAbs were optimized, or if the mAbs were used in combination with other mAbs or therapies. Enhanced neutralization potency would also likely improve protection. More recent studies have shown that an optimized cocktail of three monoclonal antibodies (ZMapp) can provide protection in non-human primates up to six days post-exposure.

There is a gap in treatment of filovirus infection. Only a handful of animal challenge studies have been performed with mAb therapies, in part because few mAbs that target GP (the primary neutralization target) exist. Most antibodies elicited in natural infection react preferentially with a secreted, dimeric version of the glycoprotein known as sGP and do not neutralize the fusion-relevant GP spike (4, 25, 26). Wilson et al. first demonstrated that GP-specific neutralizing antibodies (nAbs) could protect mice from EBOV challenge (27). However, three of five protective antibodies recognize highly variable sequences within the GP1 mucin-like domain, rendering them unlikely candidates for development of cross-neutralizing mAbs. Antibodies KZ52 and 16F6 are among the few well-characterized nAbs and both bind to the GP prefusion core (13, 14). KZ52 was identified by phage-based panning of a B-cell antibody library isolated from a human survivor of EBOV infection (28). Initial experiments in rodent protection studies were promising, but KZ52 failed to protect in macaques when administered on days −1 and +4 at 50 mg/kg (12, 20). 16F6, a mouse mAb, was identified recently by Dr. Dye's group by vaccination with vector-based vaccine expressing SUDV GP (14).

mAb 16F6 is much more potent than is KZ52 against the corresponding virus species, but its murine scaffold limits therapeutic utility at this point. Fully humanized 16F6 variants have been developed (U.S. patent application Ser. No. 14/291,608, filed May 30, 2014, hereby incorporated by reference). Head-to-head comparison in neutralization assays using a vesicular stomatitis virus pseudotyped with GP (VSV-GP) with KZ52 (against EBOV GP, GPEBOV) and 16F6 (against SUDV GP, GPSUDV) indicates that 16F6 can reduce infectivity by ∼100-fold more than KZ52 at high antibody concentrations (FIG. 3). Both KZ52 and 16F6 are narrowly strain specific (KZ52 for EBOV and 16F6 for SUDV), and therefore have limited potential as immunotherapeutics because they cannot cross-neutralize (13, 14).

Several candidate therapies and vaccines are under exploration for Filovirus infection (27-33). Multiple promising vaccine candidates are able to protect NHPs from lethal challenge, including adenovirus-vectored, VSV-vectored, and virus-like particle-based vaccines (29-32). While any safe and effective EBOV vaccine will be useful for populations or workers that are at high risk for exposure, it is unlikely that vaccination against EBOV will be practical on a general population level. Therefore, there is still a need for an EBOV therapy that can be used to treat acute exposure or infection. Other biologics are under evaluation, including an antisense therapy undergoing clinical trials, and a promising RNAi therapy (33, 34). However, the use of nucleic acids as therapeutic agents in general is in its infancy and therefore there is a high barrier to FDA approval for such biologics. Furthermore, these therapeutic nucleic acids are strain-specific. Some small molecules against EBOV or host targets are also being explored, but studies are largely limited to early proof-of-concept stage (35-37).

Based on favorable expression and stability profiles, Bis-mAbs scKZ52-F4 LCN, scKZ52-F4 HCC, scKZ52-E10 LCN, and scKZ52-E10 HCC were chosen for additional analysis. These four Bis-mAbs showed dose-dependent neutralization of both VSV-GP pseudotyped viruses, although the $IC_{50}$ values were in general higher for VSV-$GP_{SUDV}$ than VSV-$GP_{EBOV}$ for the "LCN" constructs (FIG. 9A). For both "HCC" constructs the relative $IC_{50}$ values for the two pseudotyped viruses were approximately the same. In all cases, the highest levels (≥95%) of neutralization were achieved at 100 nM Bis-mAb concentration against both pseudotyped viruses. The four Bis-mAbs were also tested for their capacity to neutralize authentic EBOV (Kikwit-1995) and SUDV (Boniface-2000) under BioSafety Level 4 (BSL4) conditions using a plaque reduction neutralization test (PRNT) (FIG. 9B). For all Bis-mAbs, potent neutralization of both EBOV and SUDV were observed in both assays, with low- or sub-nanomolar $IC_{50}$ values in the PRNT assay for both viruses.

In Vivo Efficacy. To explore the protective potential of a single cross-binding monoclonal antibody reagent, scKZ52-F4 LCN and scKZ52-F4 HCC were evaluated for their ability to confer protection of mice in two separate mouse models with post-exposure dosing (FIG. 10). For EBOV, a well-established mouse challenge model was employed with mouse-adapted (ma) EBOV (Mayinga) and WT C57BL/6 mice (40). For SUDV, this laboratory has previously reported a model for pathogenicity that utilizes type I interferon α/β receptor knockout mice infected at 4 weeks old with human lethal SUDV (Boniface) (41, 39). For maEBOV, a single Bis-mAb dose (200 μg) was provided 24 hours post-challenge and for SUDV, two doses (500 μg each) were provided at one and four days post-exposure. The SUDV model, which involves immunocompromised mice infected at 4 weeks of age, provides a more stringent requirement for protection, and thus higher antibody doses are required than that used for the maEBOV model. Monospecific mAbs Z.6D8 (EBOV) and F4 (SUDV) were included as controls as they have previously shown excellent protection against their respective viruses (41).

Both Bis-mAb treatments resulted in high (>70%) protection in both models, with scKZ52-F4 HCC conferring 100% protection against both viruses. As expected, Z.6D8 as a treatment was not protective against SUDV but was 100% protective against EBOV. SUDV monospecific mAb F4 provided 100% protection against SUDV, as we have previously reported (41) and afforded partial (30%) protection against maEBOV. However, the level of protection for F4 against maEBOV is not statistically distinguishable from a PBS control group, in which all mice succumbed to disease by day 7 (p=0.13). Murine 16F6 afforded no protection against maEBOV in a group size of n=5 challenge experiment. The 100% protection from maEBOV observed for scKZ52-F4 HCC was statistically distinguishable from both PBS and F4 controls in this experiment, whereas 70% protection of scKZ52-F4 LCN was distinguishable only from the PBS. These results indicate that both scKZ52-F4 HCC and scKZ52-F4 LCN provide statistically significant protection relative to a PBS control group. For SUDV, both Bis-mAbs and F4 were significantly protective relative to the Z.6D8 negative control treatment group.

Aggregate weight loss was observed in the Bis-mAb- and F4-treated group during the course of the SUDV challenge, a phenomenon we have previously reported for post-exposure dosing of protective SUDV mAbs (41,39). However, the surviving Bis-mAb or mAb-treated population continued to gain weight (on average) after day 8. For maEBOV, mean weight loss was observed during the initial infection period for scKZ52-F4 LCN- and F4-treated mice, as some mice became sick, but this trend was not observed with either Z.6D8 or scKZ52-F4 HCC mice. All mice from the Z.6D8- and scKZ52-F4 HCC-treated groups survived the infection.

Figures 10A, 10B, 10C, 10D:
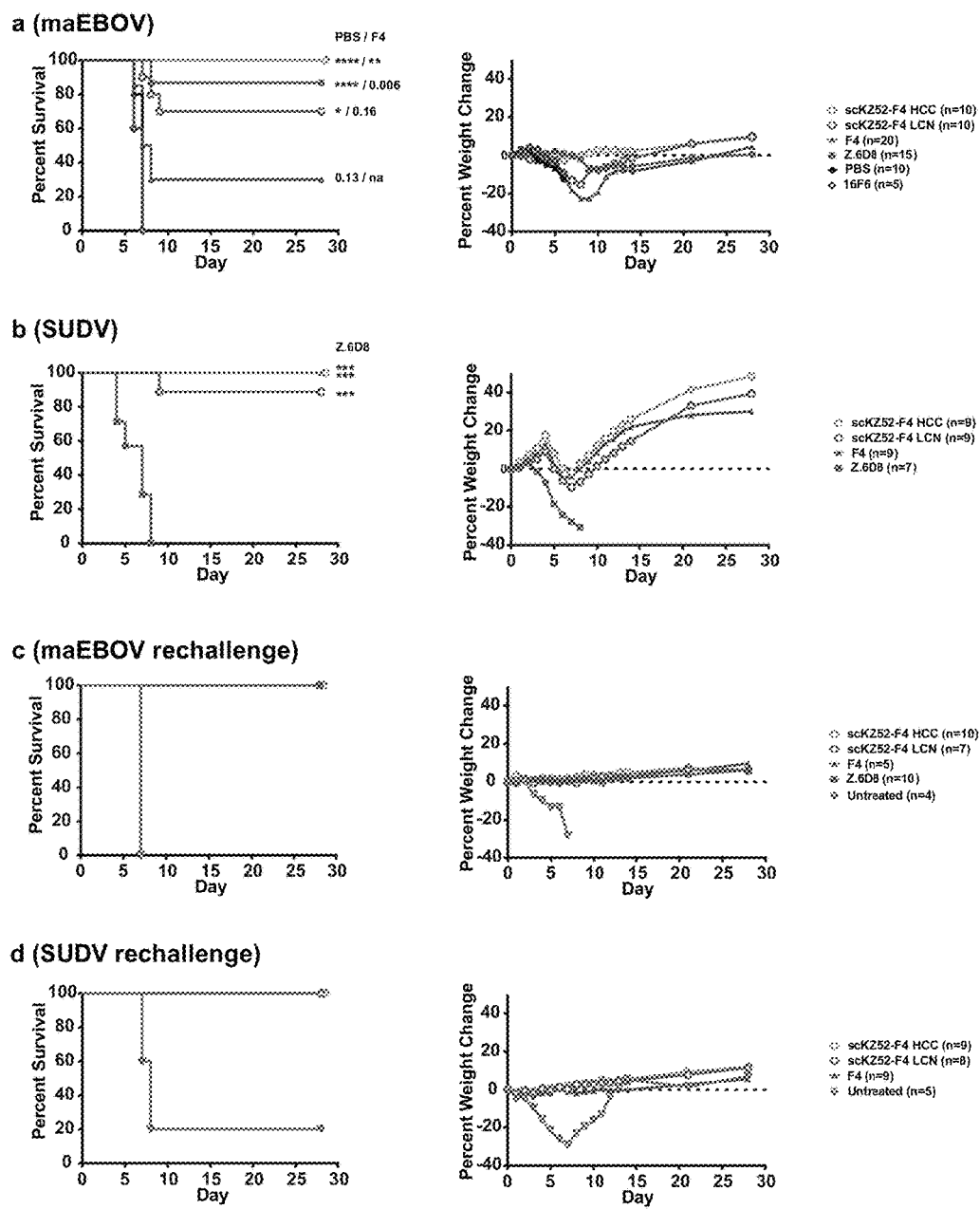

To examine the capacity for memory immunity in Bis-mAb and mAb-treated mice, the surviving cohort of both EBOV and SUDV challenges were subjected to rechallenge (with the same isolate of virus) without mAb treatment 35 days after the initial challenge (FIGS. 10C and 10D). For both EBOV and SUDV, Bis-mAb or mAb treated mice were completely protected against viral rechallenge with no observable aggregate weightloss, indicating memory immunity had been established. In both cases, an untreated negative control group was also included to confirm lethality of the virus.

Materials and Methods

Bispecific construct cloning using pMAZ-IgH and pMAZ-IgL vectors from Mazor et al. (38):

Constructs: KZ52 scFv was linked via a flexible peptide linker to either full length E10 or F4 IgG at the N- or C-terminus of the heavy chain (HC) and light chain (LC) (total of 8 constructs) were ordered from Genewiz, South Plainfield, N.J. The nucleotide sequence was optimized for *E. coli*. The constructs were re-suspended in MilliQ™ water to a final concentration of 100 ng/μL.

Cloning: KZ52-E10 and KZ52-F4 N-terminal HC fusions: pMAZ-IgH and the constructs were digested using BssHII and NheI in a final volume of 50 μL for 3 hours. Digests were purified using the Qiagen Gel Extraction Kit. The antibody inserts were ligated into the digested IgH vector using the Quick Ligase kit from NEB. The ligation product was then transformed into Top10 cells and plated onto LB/Carb plates. Sequences were verified via Sanger Sequencing by Genewiz.

KZ52-E10 and KZ52-F4 N-terminal LC fusions: pMAZ-IgL and the constructs were digested using BssHII and BsiWI in a final volume of 50 μL for 3 hours. Subsequent steps were performed as above.

KZ52-F4 C-terminal HC and LC fusions: pMAZ-IgH, pMAZ-IgL and the constructs were digested with BssHII and XbaI ina final volume of 50 μL for 3 hours. Subsequent steps were performed as above.

KZ52-E10 C-terminal HC and LC fusions: A BamHI restriction site was engineered into the flexible peptide linker for the KZ52-F4 C-terminal HC and LC fusions. To produce KZ52-E10 C-terminal HC and LC fusions, the F4-KZ52 C-terminal HC and LC (in pMAZ vectors) were digested with BssHII and BamHI in a final volume of 50 μL for 3 hours. Subsequent steps were performed as above.

After sequences were verified, all 8 constructs were maxiprepped using the Macherey-Nagel maxiprep kit. Additionally, the wildtype (WT) E10 and F4 IgH and IgL DNA was also maxiprepped.

Transfections: Transfections were carried out at the AECOM protein production facility using HEK293F cells in 600 mL cultures as follows:

For each bispecific construct, the WT E10 or F4 IgH or IgL was paired with the corresponding bispecific DNA (example: E10-KZ52 N-terminal HC-IgH is paired with the E10 IgL WT). Both plasmids were co-transfected into 293F cells at a final amount of 201 μg using 1.2 mg of PEI transfection reagent in 50 mL PBS. Cells were incubated for 6 days at 37° C., 5% $CO_2$, and 110 rpm.

Antibody purification: Cells were spun down at 4000 rpm, 4° C., for 15 minutes. The supernatant was brought to a pH of 8.0 using diluted NaOH. Protein A agarose beads (ThermoScientific) were washed in 10 mL Gentle Antibody Binding Buffer (ThermoScientific). Washed beads were then incubated with antibody containing supernatants for approximately 2 hours at 4° C. The flow through was collected. Beads were washed 2 times with 10 mL of Gentle Antibody Binding Buffer. Antibodies were eluted 5 times using 2.5 mL of Gentle Antibody Elution Buffer (Thermo- Scientific). Elutions were subsequently desalted into 150 mM HEPES/200 mM NaCl using PD-10 Desalting Columns (GE Healthcare). For verification of purity, SDS-PAGE (10-15%) were run and stained with Coomassie Blue dye.

Results

Multi-specific antibody-based structures are disclosed herein, including the exemplified bispecific antibodies (Bis-mAbs) comprising a genetic fusion of a single chain Fv (scFv) and an IgG, each harboring two separate specificities. In one embodiment, EBOV/SUDV Bis-mAbs were created by fusing the scFv of EBOV-specific mAb KZ52 and the IgG of SUDV specific mAbs E10 or F4. Several formats for the fusion are available, with the scFv as an N-terminal fusion to the IgG heavy chain (N' heavy chain or HCN'), the IgG light chain (N' light chain or LCN'); or as a C-terminal fusion to the IgG heavy and light chains (C' heavy chain or HCC', and C' light chain or LCC') (see FIG. 4). KZ52 (EBOV-specific) is a human antibody, and E10 and F4 (SUDV-specific) are fully humanized versions of the mouse antibody 16F6 recently reported. All together, a total of eight Bis-mAbs were produced, and could be purified from HEK293F cells in varying yield and stability (see FIG. 5). The binding of all eight for the envelope glycoprotein (GP) from EBOV or SUDV was demonstrated (see FIGS. 5 and 7).

Finally, in a pseudotyped virus infection model, where vesicular stomatitis virus displaying the EBOV or SUDV GP was used as the infecting virus, it was found that all eight Bis-mAbs could neutralize GP-mediated cell entry for both EBOV and SUDV GP at 133 nM (see FIG. 8). Testing of the bispecific antibody compositions under BSL4 conditions is performed against authentic pathogens.

REFERENCES

1. Kuhn, J. H., Becker, S., Ebihara, H., Geisbert, T. W., Johnson, K. M., Kawaoka, Y., Lipkin, W. I., Negredo, A. I., Netesov, S. V., Nichol, S. T., Palacios, G., Peters, C. J., Tenorio, A., Volchkov, V. E., and Jahrling, P. B. (2010) Proposal for a revised taxonomy of the family Filoviridae: classification, names of taxa and viruses, and virus abbreviations. Arch. Virol. 155, 2083-2103.
2. Feldmann, H., and Gesibert, T. W. (2011) *Ebola* haemorrhagic fever. Lancet 9768, 849-862.
3. Miller, E. H., and Chandran, K. (2012) Filovirus entry into cells—new insights. Curr. Opin. Virol. 2, 206-214.
4. Lee, J. E., and Saphire, E. O. (2009) Neutralizing *ebolavirus*: structural insights into the envelope glycoprotein and antibodies targeted against it. Curr. Opin. Struct. Biol. 19, 408-417.
5. Leroy, E. M., Kumulungui, B., Pourrut, X., Rouquet, P., Hassanin, A., Yaba, P., Delicat, A., Paweska, J. T., Gonzalez, J. P., and Swanepoel, R. (2005) Fruit bats as reservoirs of *Ebola* virus. Nature 438, 575-576.
6. http://www.cdc.gov/ncidod/dvrd/spb/mnpages/dispages/ebola.htm
7. Bradfute, S. B., Warfield, K. L., and Bavari, S. (2008) Functional CD8+ T cell responses in lethal *Ebola* virus infection. J. Immunol. 180, 4058-4066.
8. Zampieri, C. A., Sullivan, N. J., and Nabel, G. J. (2007) Immunopathology of highly virulent pathogens: insights from *Ebola* virus. Nat. Immunol. 8, 1159-1164.
9. Geisbert, T. W., Hensley, L. E., Larsen, T., Young, H. A., Reed, D. S., Geisbert, J. B., Scott, D. P., Kagan, E., Jahrling, P. B., and Davis, K. J. (2003) Pathogenesis of *Ebola* hemorrhagic fever in cynomolgus macaques: evidence that dendritic cells are early and sustained targets of infection. Am. J. Pathol. 163, 2347-2370.
10. Hensley, L. E., Jones, S. M., Feldmann, H., Jahrling, P. B., and Geisbert, T. W. (2005) *Ebola* and *Marburg* viruses: pathogenesis and development of countermeasures. Curr. Mol. Med. 5, 761-772.
11. Wilson, J. A., and Hart, M. K. (2001) Protection from *Ebola* virus mediated by cytotoxic T lymphocytes specific for the viral nucleoprotein. J. Virol. 75, 2660-2664.
12. Parren, P. W., Geisbert, T. W., Maruyama, T., Jahrling, P. B., and Burton, D. R. (2002) Pre- and postexposure prophylaxis of *Ebola* virus infection in an animal model by passive transfer of a neutralizing human antibody. J. Virol. 76, 6408-6412.
13. Lee, J. E., Fusco, M. L., Hessell, A. J., Oswald, W. B., Burton, D. R., and Saphire, E. O. (2008) Structure of the *Ebola* virus glycoprotein bound to an antibody from a human survivor. Nature 454, 177-182.
14. Dias, J. M., Kuehne, A. I., Abelson, D. M., Bale, S., Wong, A. C., Halfmann, P., Muhammad, M. A., Fusco, M. L., Zak, S. E., Kang, E., Kawaoka, Y., Chandran, K., Dye, J. M., and Saphire, E. O. (2011) A shared structural solution for neutralizing ebolaviruses. Nat. Struct. Mol. Biol. 18, 1424-1427.
15. Lee, J. E., and Saphire, E. O. (2009) *Ebolavirus* glycoprotein structure and mechanism of entry. Future Virol. 4, 621-635.
16. Weissenhorn, W., Carfi, A., Lee, K.-H., Skehel, J. J., and Wiley, D. C. (1998) Crystal structure of the *Ebola* virus membrane fusion subunit, GP2, from the envelope glycoprotein ectodomain. Mol. Cell 2, 605-616.
17. Malashkevich, V. N., Schneider, B. J., McNally, M. L., Milhollen, M. A., Pang, J. X., and Kim, P. S. (1999) Core structure of the envelope glycoprotein GP2 from *Ebola* virus at 1.9-Å resolution. Proc. Natl. Acad. Sci. USA 96, 2662-2667.
18. Koellhoffer, J. F., Malashkevich, V. N., Harrison, J. S., Toro, R., Bhosle, R. C., Chandran, K., Almo, S. C., Lai, J. R. (2012) Crystal structure of the *Marburg* virus GP2 core domain in its postfusion conformation. Biochemistry 51, 7665-7675.
19. Harrison, J. S., Koellhoffer, J. F., Chandran, K., and Lai, J. R. (2012) *Marburg* virus glycoprotein GP2: pH-dependent stability of the ectodomain α-helical bundle. Biochemistry 51, 2515-2525.
20. Oswald, W. B., Geisbert, T. W., Davis, K. J., Geisbert, J. B., Sullivan, N. J., Jahrling, P. B., Parren, P. W., and Burton, D. R. (2007) Neutralizing antibody fails to impact the course of *Ebola* virus infection in monkeys. PLoS Pathog. 3, e9.
21. Dye, J. M., Herbert, A. S., Kuehne, A. I., Barth, J. F., Muhammad, M. A., Zak, S. E., Ortiz, R. A., Prugar, L. I., and Pratt, W. D. (2012) Postexposure antibody prophylaxis protects nonhuman primates from filovirus disease. Proc. Natl. Acad. Sci. USA 109, 5034-5039.
22. Wong, G., Richardson, J. S., Pillet, S., Patel, A., Qiu, X., Alimonti, J., Hogan, J., Zhang, Y., Takada, A., Feldmann, H., Kobinger, G. P. (2012) Immune parameters correlate with protection against ebola virus infection in rodents and nonhuman primates. Sci. Transl. Med. 4, 158ra146.
23. Olinger, G. G. Jr., Pettitt, J., Kim, D., Working, C., Bohorov, O., Bratcher, B., Hiatt, E., Hume, S. D., Johnson, A. K., Morton, J., Pauly, M., Whaley, K. J., Lear, C. M., Biggins, J. E., Scully, C., Hensley, L., Zeitlin, L. (2012) Delayed treatment of *Ebola* virus infection with plant-derived monoclonal antibodies provides protection in rhesus macaques. Proc. Natl. Acad. Sci. USA 109, 18030-18035.
24. Marzi, A., Yoshida, R., Miyamoto, H., Ishijim, M., Suzuki, Y., Higuchi, M., Matsuyama, Y., Igarashi, M., Nakayama, E., Kuroda, M., Saijo, M., Feldmann, F., Brining, D., Feldmann, H., and Takada A. (2012) Protective efficacy of neutralizing monoclonal antibodies in a nonhuman primate model of Ebola hemorrhagic fever. PLoS One 7, e36192.
25. Wilson, J. A., Bosio, C. M., and Hart, M. K. (2001) Ebola virus: the search for vaccines and treatments. Cell Mol. Life Sci. 58, 1826-1841.
26. Sullivan, N. J., Martin, J. E., Graham, B. S., and Nabel, G. J. (2009) Correlates of protective immunity for Ebola vaccines: implications for regulatory approval by the animal rule. Nat. Rev. Microbiol. 7, 393-400.
27. Wilson, J. A., Hevey, M., Bakken, R., Guest, S., Bray, M., Schmaljohn, A. L., and Hart, M. K. (2000) Epitopes involved in antibody-mediated protection from Ebola virus. Science 287, 1664-1666.
28. Maruyama, T., Rodriguez, L. L., Jahrling, P. B., Sanchez, A., Khan, A. S., Nichol, S. T., Peters, C. J., Parren, P. W., and Burton, D. R. (1999) Ebola virus can be effectively neutralized by antibody produced in natural human infection. J. Virol. 73, 6024-6030.
29. Shurtleff, A. C., Warren, T. K., and Bavari, S. (2011) Non-human primates as models for the discovery and development of ebolavirus therapeutics. Expert Opin. Drug Discov. 6, 233-250.
30. Warfield, K. L., and Aman, M. J. (2011) Advances in virus-like particle vaccines for filoviruses. J. Infect. Dis. 204 Suppl 3, S1053-1059.
31. Fausther-Bovendo, H., Mulangu, S., and Sullivan, N. J. (2012) Ebolavirus vaccines for humans and apes. Curr. Opin. Virol. [Epub ahead of print] (May 3, PMID: 22560007)
32. Hoenen, T., Grosth, A., and Feldmann, H. (2012) Current ebola vaccines. Expert Opin. Biol. Ther. [Epub ahead of print] (May 5, PMID: 22559078)
33. Warren, T. K., Warfield, K. L., Wells, J., Swenson, D. L., Donner, K. S., Van Tongeren, S. A., Garza, N. L., Dong, L., Mourich, D. V., Crumley, S., Nichols, D. K., Iversen, P. L., and Bavari, S. (2010) Advanced antisense therapies for postexposure protection against lethal filovirus infections. Nat. Med. 16, 991-994.
34. Geisbert, T. W., Lee, A. C., Robbins, M., Geisbert, J. B., Honko, A. N., Sood, V., Johnson, J. C., de Jong, S., Tavakoli, I., Judge, A., Hensley, L. E., and Maclachlan, I. (2010) Postexposure protection of non-human primates against a lethal Ebola virus challenge with RNA interference: a proof-of-concept study. Lancet 375, 1896-1905.
35. Panchal, R. G., Reid, S. P., Tran, J. P., Bergeron, A. A., Wells, J., Kota, K. P., Aman, J., and Bavari, S. (2012) Identification of an antioxidant small-molecule with broad-spectrum antiviral activity. Antiviral Res. 93, 23-29.
36. Cote, M., Misasi, J., Ren, T., Bruchez, A., Lee, K., Filone, C. M., Hensley, L., Li, Q., Ory, D., Chandran, K., and Cunningham, J. (2011) Small molecule inhibitors reveal Niemann-Pick C1 is essential for Ebola virus infection. Nature 477, 344-348.
37. Basu, A., Li, B., Mills, D. M., Panchal, R. G., Cardinale, S. C., Butler, M. M., Peet, N. P., Majgier-Baranowska, H., Williams, J. D., Patel, I., Moir, D. T., Bavari, S., Ray, R., Farzan, M. R., Rong, L., and Bowlin, T. L. (2011) Identification of a small-molecule entry inhibitor for filoviruses. J. Virol. 85, 3106-3119.
38. Mazor, Y., Barnea, I., Keydar, I., and Benhar, I. (2007) Antibody internalization studied using a novel IgG binding toxin fusion. Journal of Immunological Methods, 321, (1), 41-59.
39. Brannan, J. M. et al. Interferon alpha/beta Receptor-Deficient Mice as a Model for Ebola Virus Disease. The Journal of infectious diseases 212 Suppl 2, S282-294, doi:10.1093/infdis/jiv215 (2015).
40. Bray, M., Davis, K., Geisbert, T., Schmaljohn, C. & Huggins, J. A mouse model for evaluation of prophylaxis and therapy of Ebola hemorrhagic fever. The Journal of infectious diseases 178, 651-661 (1998).
41. Chen, G. et al. Synthetic Antibodies with a Human Framework That Protect Mice from Lethal Sudan Ebolavirus Challenge. ACS Chemical Biology 9, 2263-2273, doi:10.1021/cb5006454 (2014).

What is claimed is:

1. A composition comprising (1) a first single chain variable fragment (scFv) comprising at least one complementarity-determining region (CDR) directed to a membrane glycoprotein pre-fusion core of a first species of filovirus, which first scFv is covalently joined to (2) a first polypeptide of an immunoglobulin G (IgG) comprising at least one CDR directed to a membrane glycoprotein pre-fusion core of a second species of filovirus, wherein the first species of filovirus and second species of filovirus are different species, wherein the first scFv comprises (i) SEQ ID NOS: 9 and 11, or (ii) SEQ ID NOS: 13 and 15, and wherein the IgG comprises (i) SEQ ID NOS: 13 and 15, or SEQ ID NOS: 9 and 11, respectively.

2. The composition of claim 1, wherein the first scFv is covalently joined at its N terminal to a C terminal of a first polypeptide of the IgG.

3. The composition of claim 2, wherein the first polypeptide of the IgG is a heavy chain.

4. The composition of claim 2, wherein the first polypeptide of the IgG is a light chain.

5. The composition of claim 1, wherein the first scFv is covalently joined at its C terminus to an N terminus of a first polypeptide of the IgG.

6. The composition of claim 5, wherein the first polypeptide of the IgG is a heavy chain.

7. The composition of claim 5, wherein the first polypeptide of the IgG is a light chain.

8. The composition of claim 1, wherein the scFv is covalently joined to the first polypeptide via a polypeptide linker.

9. The composition of claim 8, wherein the polypeptide linker comprises the sequence GGSAGSAGSAGSGGS (SEQ ID NO:17).

10. The composition of claim 1, wherein a $V_H$ sequence of the first scFv has a sequence identical to $V_H$ sequence of a human or a humanized antibody directed to the membrane glycoprotein pre-fusion core of the first species of filovirus.

11. The composition of claim 1, wherein a $V_L$ sequence of the first scFv has a sequence identical to $V_L$ sequence of a human or a humanized antibody directed to the membrane glycoprotein pre-fusion core of the first species of filovirus.

12. The composition of claim 1, wherein the $V_H$ sequence of the scFv is joined to the $V_L$ sequence of the first scFv by a polypeptide linker.

13. The composition of claim 12, wherein the polypeptide linker is majority glycine residues.

14. The composition of claim 13, wherein the polypeptide linker is

GGGGSGGGGSGGGGS. (SEQ ID NO: 18)

15. The composition of claim 1, wherein the composition comprises a second scFv, wherein the second scFv is covalently joined to a second polypeptide of the IgG.

* * * * *